United States Patent [19]

Ohashi et al.

[11] Patent Number: 5,468,852
[45] Date of Patent: Nov. 21, 1995

[54] OLIGONUCLEOTIDES FOR DETECTING BACTERIA

[75] Inventors: Tetsuo Ohashi, Kyoto; Jun Tada, Muko; Shigeru Fukushima, Otsu; Hiroko Ozaki, Kyoto; Naoyuki Nishimura; Yoshinari Shirasaki, both of Kyoto; Koichi Yamagata, Osaka, all of Japan

[73] Assignee: Shimadzu Corporation, Kyoto, Japan

[21] Appl. No.: 932,379

[22] Filed: Aug. 19, 1992

[30] Foreign Application Priority Data

Feb. 18, 1992 [JP] Japan ..................................... 4-030755
Mar. 24, 1992 [JP] Japan ..................................... 4-066082

[51] Int. Cl.⁶ .................................................. C07H 21/04
[52] U.S. Cl. .................. 536/24.33; 536/23.7; 536/24.32
[58] Field of Search ................... 435/6, 252.1; 536/23.7, 536/24.32, 24.33

[56] References Cited

FOREIGN PATENT DOCUMENTS 4020299 1/1992 Japan .............................. C07H 21/00

OTHER PUBLICATIONS

Nishibuchi et al., Infect. Immun 57(9): 2691–2697, 1989.
Nishibuchi et al. Mol Microbiol 4(1) 87–100, 1990.

Primary Examiner—Margaret Parr
Assistant Examiner—Scott W. Houtteman
Attorney, Agent, or Firm—Birch, Stewart, Kolasch & Birch

[57] ABSTRACT

Oligonucleotides (SEQ ID NOs 1–8) selectively hybridizable with a specific gene of *Vibro parahaemolyticus*, oligonucleotides (SEQ ID NOs 9–13) selectively hybridizable with the LT gene of toxigenic *Escherichia coil*, oligonucleotides (SEQ ID NOs 14–21) selectively hybrizable with the STh or STp gene of toxigenic *Escherichia coil*, oligonucleotides (SEQ ID NOs 22–47) selectively hybridizable with the entA, B, C, or D gene of *Staphylococcus aureus*, or oligonucleotides (SEQ ID NOs 48–53) selectively hybridizable with the entE gene of *Staplyloccus aureus* are prepared and used as primers for gene amplification to thereby selectively detect only respective microorganisms causing food poisoning.

3 Claims, No Drawings

OLIGONUCLEOTIDES FOR DETECTING BACTERIA

BACKGROUND OF THE INVENTION

This invention relates to means for detecting *Vibrio parahaemolyticus,* thermolable enterotoxin (LT)-producing strains of *Escherichia coli,* human thermostable enterotoxin (hereinafter, STh)- and/or porcine thermostable enterotoxin (hereinafter STp)- producing toxigenic strains of *Escherichia coli,* and *Staphylococcus aureus* in clinical examination, in particular testing in case of food poisoning, or in food inspection.

When the material to be tested is patient's vomit, feces, food, or wipe, a series of operations, namely enrichment culture, isolation culture and differential culture, are required for final identification of the pathogen or contaminant as *Vibrio parahaemolyticus,* if present. The time periods required for the respective culture steps are 10–16 hours for enrichment culture, 18–24 hours for isolation culture, and 18–24 hours for differential culture, the total time being as long as 2–4 days. Tests to be included in differential culture include growth test in agar medium supplemented with NaCl, gram staining, oxydase test and so forth. They involve complicated and troublesome procedures and are time-consuming and expensive.

For detecting the pathogenic factor of *Vibrio parahaemolyticus,* the so-called reverse passive hemagglutination reaction is available which uses a specific immune globulin obtained from an antiserum to thermostable (thermostable) direct hemolysin (TDH) produced by *Vibrio parahaemolyticus.* However, this reaction needs 20–24 hours until a result is obtained.

As mentioned above, the prior art methods invariably need a very complicated procedure and a long period of time until identification as *Vibrio parahaemolyticus,* hence not suited for use in clinical laboratory testing, among others, which demands speediness.

Recently, the DNA probe or hybridization techniques, which use olgonucleotides, have been attempted. However, these techniques, which comprises hybridization with oligonucleotide label-modified probes on a membrane or some other support, followed by detection, can scarcely have a satisfactory detection sensitivity and selectivity.

Moreover, strains of *Vibrio parahaemolyticus* that have a novel pathogenic factor, namely TDH-related hemolysin (TRH), which is different from those so far reported, has been discovered recently and, further, it has become clear that the gene coding for TRH includes two types, namely trh1 and trh2, which differ in base sequence from each other. However, any method has been established as yet for directly testing for *Vibrio parahaemolyticus* strains having this new pathogenic factor.

For identifying a pathogen or contaminant as a toxigenic strain of *Escherichia coli,* enrichment culture, isolation culture, pure culture and confirmation culture are required and are to be followed further by serological testing, enterotoxin production test and other biochemical tests. Each culture step requires 18–24 hours and the total time, inclusive of the time for subsequent tests, amounts to as long as a week or so.

For detecting thermolabile enterotoxin (hereinafter, LT), kits for detecting enterotoxin which utilize the reverse passive latex agglutination reaction are commercially available. However, since, immunologically, cholera enterotoxin (hereinafter, CT) and LT have common antigenicity, it is difficult to detect in distinction from each other.

Moreover, the samples should be pure cultures already roughly estimated with respect to their identification. The steps preceding and including this rough estimation step require complicated procedures and a long period of time. In addition, the time for working with said kits alone amounts to 20–24 hours.

As mentioned above, the prior art methods for detecting toxinogenic strains of *Escherichia coli* invariably need very complicated procedures and are time-consuming, hence are not suited for use in clinical laboratory testing, among others, which demands speediness.

Recently, the DNA probe or hybridization techniques, which use olgonucleotides, have been attempted. However, these techniques, which comprises hybridization with oligonucleotide label-modified probes on a membrane or some other support, followed by detection, can scarcely have a satisfactory detection sensitivity and selectivity.

For detecting and identifying STh- or STp-producing toxigenic strains of *Escherichia coli,* it is necessary to perform enrichment culture, isolation culture, pure culture and confirmation culture. Furthermore, a pathogen or contaminant can be identified as a thermostable enterotoxin-producing strain of *Escherichia coli* only after serologic, biochemical, and enterotoxin production tests.

However, 18–24 hours is required for each culture step, and the total time, inclusive of the time for the subsequent tests, amounts to at least one week.

The suckling mouse technique is the only testing method for the production of thermostable enterotoxin. For this method, mice 2–3 days after birth must be prepared and the procedure is complicated and requires skill. Moreover, three or more mice should be subjected to the test to obtain the mean value. For these and other reasons, said method is unsatisfactory in reproducibility and reliability.

Recently, the DNA probe or hybridization techniques, which use olgonucleotides, have been attempted. However, these techniques, which comprises hybridization with oligonucleotide label-modified probes on a membrane or some other support, followed by detection, can scarcely have a satisfactory detection sensitivity and selectivity.

The materials to be tested in case of food poisoning include patients' vomits, feces, the same foods as taken by patients and/or wipes used in patients' environment. For the detection and identification of *Staphylococcus aureus* in these materials, it is necessary to first perform enrichment culture, isolation culture, pure culture and confirmation culture.

However, 18–24 hours is required for each culture step, and the total time, including the time necessary for the subsequent tests, is very long, amounting to about 4 days.

Biochemical tests to be carried out following confirmation culture include, among others tests for aerobic growth, VP reactivity, nitrite reduction, Tween 80 hydrolysis, hyaluronidase activity, sugar degradation and so forth. These tests require complicated procedures and are time-consuming and expensive.

In the case of *Staphylococcus aureus,* testing of isolates for enterotoxin production is regarded as the most reliable method of identifying pathogenic bacteria causative of food poisoning and diarrhea. However, even when commercially available simple reagent kits are used, 18–20 hours is required until results can be obtained. This means lack of speediness. A simple reagent kit for enterotoxin E (see) is not commercially available.

Recently, the DNA probe or hybridization techniques, which use olgonucleotides, have been attempted. However, these techniques, which comprises hybridization with oligonucleotide label-modified probes on a membrane or some other support, followed by detection, can scarcely have a satisfactory detection sensitivity and selectivity.

OBJECTS OF THE INVENTION

It is an object of the invention to provide a simple, speedy and highly sensitive method useful in testing for microorganisms causative of food poisoning, which method comprises detecting a *Vibrio parahaemolyticus*-derived specific gene by the gene amplification technique using oligonucleotides as primers in the nucleic acid synthesis reaction.

Another object of the invention is to provide a simple, speedy and highly sensitive method useful in testing for microorganisms causative of food poisoning, which method comprises detecting a toxigenic *Escherichia coli*-derived nucleic acid by the gene amplification technique using oligonucleotides as primers in the nucleic acid synthesis reaction.

A further object of the invention is to provide a simple, speedy and highly sensitive method useful in testing for causative microorganisms in case of food poisoning or diarrhea, which method comprises detecting the toxigenic *Escherichia coli*-derived STh or STp gene by the gene amplification technique using oligonucleotides as primers in the nucleic acid synthesis reaction.

A still further object of the invention is to provide a simple, speedy and highly sensitive method useful in testing for causative microorganisms in case of food poisoning or diarrhea, which method comprises detecting the *Staphylococcus aureus*-derived entA, B, C, D and E genes (enterotoxin A, B, C, D and E gene) by the gene amplification technique using oligonucleotides as primers in the nucleic acid synthesis reaction.

SUMMARY OF THE INVENTION

In accordance with a first aspect of the invention, oligonucleotides capable of selectively hybridizing with a specific gene of *Vibrio parahaemolyticus* are prepared and used as primers in gene amplification to thereby selectively detect *Vibrio parahaemolyticus* alone, which causes food poisoning symptoms.

In accordance with a second aspect of the invention, oligonucleotides capable of selectively hybridizing with a toxigenic *Escherichia coli*-derived nucleic acid are prepared and used as primers in gene amplification to thereby selectively detect toxigenic *Escherichia coli* alone, which causes food poisoning symptoms.

In accordance with a third aspect of the invention, oligonucleotides capable of selectively hybridizing with the STh and/or STp gene of toxigenic *Escherichia coli* are prepared and used as primers in gene amplification to thereby selectively detect STh- or STp-producing toxigenic *Escherichia coli* alone from among pathogenic *Escherichia coli* strains causing food poisoning symptoms.

In accordance with a fourth aspect of the invention, oligonucleotides capable of selectively hybridizing the entA, B, C, D and E geenes of *Staphyloccocus aureus* are prepared and used as primers in gene amplification to thereby selectively detect entA, B, C, D and E-producing *Staphylococcus aureus* alone from among *Staphylococcus aureus* strains causing food poisoning symptoms.

DETAILED DESCRIPTION OF THE INVENTION

The oligonucleotides to be used as primers in accordance with the first aspect of the invention, when intended for detecting the type 1 and type 2 thermostable hemolysin-related hemolysin genes (trh1 and trh2 genes), are chemically synthesized oligonucleotides having the sequences (5') a-GGCTCAAAATGGTTAAGCG (3') ... (a)

(5') d-CATTTCCGCTCTCATATGC (3') ... (b)

or the corresponding complementary sequences.

When intended for detecting the thermostable hemolysin gene (tdh gene), they are chemically synthesized oligonucleotides having the sequences (5') d-CCATCTGTCCCTTTTCCTGC (3') ... (c)

(5') d-CCAAATACATTTTACTTGG (3') ... (d)

(5') d-GGTACTAAATGGCTGACATC (3') ... (e)

(5') d-CCACTACCACTCTCATATGC (3') ... (f)

or the corresponding complementary sequences.

Further, when intended for detecting the thermostable hemolysin-related hemolysin gene type 1 (trh1 gene) of *Vibrio parahaemolyticus*, they are chemically synthesized oligonucleotides having the sequences or the corresponding complementary sequences.

The gene amplification can be effected by the polymerase chain reaction method developed by Saiki et al. [hereinafter, PCR method for short; Science, 230, 1350 (1985)]. This method comprises preparing two oligonucleotides, one recognizing and hybridizing with the + chain and the other recognizing and hybridizing with the − chain at both ends of a specific nucleotide sequence region to be detected (in the present case, the trh gene or tdh gene, or trh1 gene of *Vibrio parahaemolyticus*), causing them to function as primers for the template-dependent nucleotide polymerization reaction against the sample nucleic acid in the single stranded form as a result of heat denaturation, separating the resulting double-stranded nucleic acid into single strands, and again allowing the same reaction to proceed. By repeating this serial procedure, the number of copies of the region between the two primers is increased so that said region can be detected.

The sample to be tested may be a laboratory test sample such as feces, urine, blood or tissue homogenate, or a food sample.

For testing such sample by the PCR, pretreatment is necessary by which the nucleic acid components are released from microbial cells occurring in the sample.

Since, however, the PCR can proceed if several to scores of molecules of the nucleic acid hybridizable with the primers are present, short-period treatment of the laboratory sample with a lytic enzyme, a surfactant, an alkali or the like can give a sample solution containing the nucleic acid in a sufficient amount to enable the OCR to proceed.

The oligonucleotides to be used as primers in the practice of the invention are nucleotide fragments having a length of 10 bases or more, desirably 15 bases or more, from the viewpoints of selectivity, detection sensitivity and reproducibility. They may be chemically synthesized ones or natural ones. The primers need not be particularly labeled for detection purposes.

The primer-specified amplification region of the nucleotide sequence of a particular gene of *Vibrio parahaemolyticus* may comprise 50 bases to 2,000 bases, desirably 100 bases to 1,000 bases.

In carrying out the template-dependent nucleotide polymerization reaction, a thermostable DNA polymerase is used. This enzyme may be of any origin provided that it can retain its activity at temperatures of 90°–95° C. The heat denaturation is carried out at 90°–95° C., the annealing for primer hybridization at 37°–65° C., and the polymerization reaction at 50°–75° C., and these constitute one cycle of PCR. Amplification is effected by repeating 20 to 42 PCR cycles.

For detection, the reaction mixture after completion of the PCR is subjected, as such, to agarose gel electrophoresis, whereby the presence or absence of the amplified nucleotide fragment and, if present, the length thereof can be confirmed. Based on the results, judgment can be made as to whether the nucleotide having the sequence to be recognized by the primers is present in the sample or not. This judgment directly serves as a judgment as to whether *Vibrio parahaemolyticus* carrying the trh gene or the like is present or not. Other electrophoretic techniques and chromatographic techniques are also effective in detecting the amplified nucleotide fragment.

The oligonucleotides to be used in accordance with the second aspect of the invention are chemically synthesized oligonucleotides the target of which is a nucleotide sequence coding for the heat-labile toxin (LT) that is produced by toxigenic *Escherichia coli* occurring in the sample. They are complementary to said nucleotide sequence and have the following sequences (5') d-CCCAGATGAAATAAAACGT-(3') . . . (a)

(5') d-CCTGAGATATATTGTGCTC-(3') . . . (b)

(5') d-ACAAACCGGCTTTGTCAGATAT-(3') . . . (c)

(5') d-GTTATATATGTCAACCTCTGAC-(3') . . . (d)

(5') d-ACCGGTATTACAGAAATCTGA-(3') . . . (e)

or the corresponding complementary sequences.

The gene amplification is carried out based on the PCR method mentioned above.

The samples to be used and the method of pretreatment thereof may be the same as mentioned above.

The oligonucleotides to be used as primers in accordance with the second aspect of the invention each may have the same length as mentioned above with respect to the first aspect of the invention. They may be chemically synthesized ones or natural ones. The primers need not be particularly labeled for detection purposes.

The primer-specified amplification region in the nucleotide sequence of a specific gene of toxigenic *Escherichia coli* may be 50 to 2,000 bases, desirably 100 to 1,000 bases, in length, as mentioned above.

The template-dependent nucleotide polymerization reaction is carried out in the same manner as in the first aspect of the invention.

The detection can be made in the same manner as in the first aspect of the invention to thereby judge as to whether LT-producing *Escherichia coli* is present or not. Other electrophoretic techniques, chromatographic techniques and DNA probing techniques are also efficient in detecting the amplified nucleotide fragment.

The oligonucleotides to be used in accordance with the third aspect of the invention are chemically synthesized oligonucleotides supplementary to a nucleotide sequence coding for the STh gene and STp gene, when said nucleotide sequence is the target. Said synthetic nucleotides have the sequences (5') d-TGTAATTTTCTCTTTTGAAGACTC-(3') . . . (a: SEQ ID NO: 1)

(5') d-ATTACAACACAGTTCACAGCAG-(3') . . . (b: SEQ ID NO: 2)

or the corresponding complementary sequences.

When a nucleotide sequence coding for the STh gene is the target, the above-mentioned oligonucleotides are chemically synthesized oligonucleotides complementary to said nucleotide sequence and have the sequence (5') d-CCTCAGGATGCTAAACCAG-(3') . . . (c: SEQ ID NO: 3)

(5') d-AGGATGCTAAACCAGTAGAG-(3') . . . (d: SEQ ID NO: 4)

(5') d-AATTCACAGCAGTAATTGCTAC-(3') . . . (e: SEQ ID NO: 5)

or the corresponding complementary sequences.

Furthermore, when a nucleotide sequence coding for the STp gene is the target, they are chemically synthesized oligonucleotides complementary to said nucleotide sequence and have the sequences (5') d-TCTTTCCCCTCTTTTAGTCAG-(3') (f: SEQ ID NO: 6)

(5') d-GTCAACTGAATCACTTGACTC-(3') (g: SEQ ID NO: 7)

(5') d-TCACAGCAGTAAAATGTGTTG-(3') (h: SEQ ID NO: 8)

or the corresponding complementary sequences.

The gene amplification is effected based on the PCR method mentioned above.

The samples to be tested and the method of pretreatment thereof may be the same as those mentioned above with respect to the first aspect of the invention.

The oligonucleotides to be used as primers in accordance with the third aspect of the invention may have the same length as mentioned above with respect to the first aspect of the invention. Thus, they are nucleotide fragments having a length of 10 or more bases, desirably 15 or more bases, and may be chemically synthesized ones or natural ones.

The primers need not be labeled for particular detection purposes. The primer-specified amplification range in the nucleotide sequence for the STh or STp gene of toxigenic *Escherichia coli* may be the same in length as mentioned above and thus may cover 50 bases to 2,000 bases, desirably 100 bases to 1,000 bases.

The template-dependent nucleotide polymerization reaction is carried out in the same manner as mentioned above with respect to the first aspect of the invention.

The detection is conducted in the same manner as mentioned above with respect to the first aspect of the invention, whereby judgement can be made as to whether pathogenic *Escherichia coli* carrying the STh or STp gene is present or not. Other electrophoretic techniques and chromatographic techniques are also effective in detecting the amplified nucleotide fragment.

It is also possible to selectively detect the target nucleotide sequence on a membrane or some other support by allowing an oligonucleotide having one of the above sequences (a) to (h) to function as a probe. In this case, said oligonucleotide is preferably modified with a label.

The oligonucleotides to be used as primers in accordance with the fourth aspect of the invention, when a nucleotide sequence coding for the entA gene is the target, are chemically synthesized oligonucleotides complementary to said nucleotide sequence and have the sequences (5') d-GTCTGAATTGCAGGGAACAG-(3') . . . (a)

(5') d-CTTTTTTACAGATCATTCGTG-(3') . . . (b)

(5') d-TAGATTTTGATTCAAAGGATATTG-(3') . . . (c)

(5') d-CTTATTCGTTTTAACCGTTTCC-(3') . . . (d)

(5') d-AACACGATTAATCCCCTCTG-(3') . . . (e)

(5') d-TCGTAATTAACCGAAGGTTCTG-3') . . . (f)

or the corresponding complementary sequences.

When a nucleotide sequence coding for the entB gene is the target, they are chemically synthesized oligonucleotides complementary to said nucleotide sequence and have the sequences (5') d-AAATCTATAGATCAATTTCTATAC-(3') . . . (g)

(5') d-AATTATGATAATGTTCGAGTCG-(3') . . . (h)

(5') d-TTCGCATCAAACTGACAAACG-(3') . . . (i)

(5') d-CATCTTCAAATACCCGAACAG-(3') . . . (j)

(5') d-CCAAATAGTGACGAGTTAGG-(3') . . . (k)

(5') d-TCATACCAAAAGCTATTCTCAT-3') . . . (l)

or the corresponding complementary sequences.

Further, when a nucleotide sequence coding for the entC gene is the target, they are chemically synthesized oligonucleotides complementary to said nucleotide sequence and have the sequences (5') d-TCTGTAGATAAATTTTTGGCA-(3') . . . (m)

(5') d-AAAATTATGACAAAGTGAAAACAG-(3') . . . (n)

(5') d-ATGGATCAAATTACTATGTAAAC-(3') . . . (o)

(5') d-GTAGGTAAAGTTACAGGTGG-(3') . . . (p)

(5') d-TATAAGTACATTTTGTAAGTTCC-(3') . . . (q)

(5') d-CATACCAAAAAGTATTGCCGTT-(3') . . . (r)

or the corresponding complementary sequences.

When a nucleotide sequence coding for the entD gene is the target, they are chemically synthesized oligonucleotides complementary to said nucleotide sequence and have the sequences (5') d-AAAATCTGAATTAAGTAGTACCG-(3') . . . (s)

(5') d-ATAGGAGAAAATAAAAGTACAGG-(3') . . . (t)

(5') d-CTTCAATTCAAAAGAAATGGC-(3') . . . (u)

(5') d-TTGTACATATGGAGGTGTCAC-(3') . . . (v)

(5') d-TTTTAGATTTGAAATGTTGAGCC-(3') . . . (w)

(5') d-TGACACCTCCATATGTACAAG-(3') . . . (x)

(5') d-ATTATACAATTTTAAATCCTTTTGC-(3') . . . (y)

(5') d-CTGTATTTTTCCTCCGAGAGT-(3') . . . (z)

or the corresponding complementary sequences.

When a nucleotide sequence coding for the entE gene is the target, they are chemically synthesized oligonucleotides complementary to said nucleotide sequence and have the sequences (5) d-AAAAGTCTGAATTACAAAGAAATG-(3') . . . (a:SEQ ID NO;48), (5)d-GGTTTTTTCACAGGTCATCCA-(3') . . . (b:SEQ ID NO;49), (5) d-GAACAGTTACTTCTTTTTTGCTT-(3') . . . (c:SEQ ID NO;50), (5) d-CTGTCTGAGTTATATAAACCAA-(3') . . . (d:SEQ ID NO;51), (5) d-GCACCTTACCGCCAAAGCTG-(3') . . . (e:SEQ ID NO;52), (5)d-AAACAAATCATAACTTACCGTG-(3') . . . (f:SEQ ID NO;53), or the corresponding complementary sequences.

The gene amplification is carried out based on the PCR method mentioned above.

The samples to be tested and the method of pretreatment thereof may be the same as those mentioned above with respect to the first aspect of the invention.

The oligonucleotides to be used as primers in accordance with the fourth aspect of the invention may have the same length as mentioned above with respect to the first aspect of the invention. They may be chemically synthesized ones or natural ones.

The primers need not be particularly labeled for detection purposes. The primer-specified amplification range in the nucleotide sequence for the entA, B, C, D, or E gene of *Staphylococcus aureus* may cover 50 to 2,000 bases, desirably 100 to 1,000 bases, as in the cases mentioned above.

The template-dependent nucleotide polymerization reaction is carried out in the same manner as mentioned above with respect to the first aspect of the invention.

The detection is performed in the same manner as in the first aspect of the invention, whereby judgment can be made as to whether *Staphylococcus aureus* having the entA, B, C, D, or E gene is pressent or not. Other electrophoretic techniques and chromatographic techniques are also effective in detecting the amplified oligonucleotide fragment.

It is also possible to selectively detect the target oligonucleotide on a membrane or some other support by allowing an oligonucleotide having one of the sequences (a) to (z) (SEQ ID NOs 22–47) and (a) to (f) (SEQ ID NOs 48–53) given above as a probe. In this case, said oligonucleotide is preferably modified with label.

As mentioned above, the present invention makes it possible to detect *Vibrio parahaemolyticus*, toxinogenic *Escherichia coli*, or *Staphylococcus aureus* in a simple and speedy manner and with high sensitivity by detecting a *Vibrio parahaemolyticus*-derived specific gene, the toxinogenic *Escherichia coli*-derived LT gene, a toxinogenic *Escherichia coli*-derived specific gene or a specific gene of *Staphylococcus aureus* by the gene amplification technique using certain oligonucleotides as primers in the nucleic acid synthesis reaction.

EXAMPLE 1

Detection of the trh gene of *Vibrio parahaemolyticus*

EXPERIMENT 1

SAMPLE PREPARATION

A total of 326 strains of *Vibrio parahaemolyticus* and other Vibrio species as specified in Tables 1 to 15 under the columns "Strain" and "Strain No." were used. Each was inoculated into an appropriate enrichment medium and incubated overnight at 37° C. under aerobic conditions. Cells were recovered from the medium (1.5 ml) by centrifugation. They were washed once with 10 mM Tris-hydrochloride buffer (pH 7.5) and then subjected to lysis by suspending them in 0.5 ml of a 1 mg/ml lysozyme solution in the same buffer at 37° C. for 10 minutes. A phenol-chloroform mixture (mixing ratio 1:1) saturated with the above-mentioned buffer was added to the lysate solution, followed by thorough stirring. After centrifugation, the upper layer was recovered and subjected to ethanol treatment for precipitating nucleic acid components. The precipitate was dissolved in 1 ml of the above-mentioned buffer and the solution was used as a sample.

PRIMER SYNTHESIS

Based on the base sequence of the trh gene of *Vibrio parahaemolyticus* [Nishibuchi, M. et al.: Infect. Immun., 57, 2691–2697 (1989) and Kishishita et al.: Japan. J. Bacteriol., 45, 340 (1990)], the sequences specifically shown in claim 1 were selected and oligonucleotides identical in sequence therewith were chemically synthesized. The chemical synthesis was carried out by the β-cyanoethylphosphamidite method using a Cyclone Plus DNA synthesizer (Milligen/BioResearch). The oligonucleotides synthesized were purified by high-performance liquid chromatography using a C18 reversed phase column.

PCR

A reaction mixture (30 µl) was prepared by adding, to 3 µl of the sample solution mentioned above, 17.55 µl of sterile distilled water, 3 µl of 10× reaction buffer, 4,8 µl of dNTP solution, 0.75 µl of primer (a), 0.75 µl of primer (b) and 0.15 µl of thermostable DNA polymerase. Mineral oil (50 µl; Sigma) was layered on said reaction mixture placed in a container. The solutions used in preparing the reaction mixture were as shown below.

10× Reaction buffer: 500 mM KCl, 100 mM Tris-HCl (pH 8.3), 15 mM $MgCl_2$, 0.1% (w/v) gelatin.

dNTP solution: containing dATP, dCTP, dGTP and dTTP each at a final concentration of 1.25 mM.

Primer (a) and primer (b): Each was an aqueous solution of each product chemically synthesized and purified as mentioned above (concentration 5 ODU/ml).

Thermostable DNA polymerase: Taq DNA polymerase (5 units/ml; Perkin Elmer Cetus)

The reaction conditions were as follows.

Heat denaturation: 94° C., 1 minute.
Annealing: 55° C., 1 minute.
Polymerization reaction: 72° C., 1 minute.

The time require for each cycle covering the process from heat denaturation, through annealing, to polymerization reaction was 5.7 minutes. This cycle was repeated 35 times (total time required about 3 hours). For carrying out these operations, the above reaction conditions were programmed into a DNA Thermal Cycler apparatus (Perkin Elmer Cetus).

DETECTION

For detecting the amplified nucleotide fragment in the reaction mixture, agarose gel electrophoresis was performed in the following manner.

The agarose gel used had a gel concentration of 2% (w/v) and contained ethidium bromide (0.5 µl/ml). The electrophoresis was conducted at a constant voltage of 100 V for 30 minutes. The procedure and other conditions were as described in Maniatis et al.: Molecular Cloning (1982). In addition to the reaction mixture, molecular weight markers were simultaneously electrophoresed and, based on the comparison of relative mobilities, the length of the nucleotide fragment was estimated.

RESULTS

As mentioned hereinabove, the base sequence of the trh gene of *Vibrio parahaemolyticus* has already been determined and two types differing in base sequence, namely trh1 and trh2 have been reported. Therefore, the size of the nucleotide amplified by the PCR using the oligonucleotides, namely primers, of the present invention can be estimated. Thus, with primers (a) and (b), the nucleotide amplified is expected to be 251 bases long. When the size of the nucleotide amplified was in agreement with such estimated value, then it was judged that each primer contributed to correct amplification of the target region in the trh gene. The results obtained with 264 strains of *Vibrio parahaemolyticus* and 98 strains of other Vibrio species are shown in Table 1.

As can be seen from Table 1, the primers could correctly detect both the trh1 and trh2 genes of *Vibrio parahaemolyticus*.

EXPERIMENT 2

To ascertain whether the results obtained in Experiment 1 were selective for *Vibrio parahaemolyticus* strains having the trh1 or trh2 gene, diarrhea-causing microorganisms other than *Vibrio haemolyticus* but generally included as targets in clinical laboratory testing were further tested for comparison.

The method was the same as shown in Experiment 1 except that the strains listed in Tables 16 and 17 under Nos. 12, 13, 19 and 20 were cultured overnight at 37° C. under anaerobic conditions for preparing samples submissible to the PCR method. A total of 39 strains listed in Table 16 and 17 were cultured for preparing samples. The human placenta-derived DNA was diluted to a concentration of 1 µg/ml and subjected to PCR in the same manner. The results thus obtained are shown in Tables 16 and 17. Some microorganisms gave amplified nucleotide fragments, which were presumably byproducts of the PCR. All of said fragments differed in size from the nucleotide fragment anticipated from the sequence of the trh1 or trh2 gene. If these diarrhea-causing microorganisms had the same trh gene as that of *Vibrio parahaemolyticus,* the same 251-base-long nucleotide fragment as found in Experiment 1 would have been detected. It is therefore clear that the amplified nucleotides detected for some diarrhea-causing microorganisms were not the products resulting from recognition of the trh gene of *Vibrio parahaemolyticus* but that trh gene-carrying strains of *Vibrio parahaemolyticus* and other Vibrio species can be readily detected in distinction from other diarrhea-causing microorganisms. The agarose gel electrophoresis employed in the experiment described herein, when conducted under the conditions mentioned above, can distinguish nucleotides of 100 base pairs or less in size from each other when they differ by 5 to 10 base pairs, and uncleotides of 100 to 500 base pairs in size from each other when they differ by 10 to 20 base pairs. When the precision of nucleotide size determination is improved by using an acrylamide gel, for instance, the reliability in the selective detection will presumably be increased further.

EXAMPLE 2

Detection of the tdh gene of *Vibrio parahaemolyticus*

EXPERIMENT 1

SAMPLE PREPARATION

Samples were prepared in the same manner as in Example 1.

PRIMER SYNTHESIS

Based on the base sequence of the rdh gene of *Vibrio parahaemolyticus* [Nishibuchi, M. and kaper, J. B.: Mol. Microbiol., 4, 87–99 (1990)], the sequences shown in claim 2 were selected, and oligonucleotides having the same sequences as those were chemically synthesized. The chemical synthesis and purification of the oligonucleotides synthesized were carried out in the same manner as in Example 1.

PCR

The same procedure as used in Example 1 was followed except that the following primer combinations were used.

| Primer (1) | Primer (2) |
|---|---|
| (c) | (d) |
| (e) | (d) |
| (e) | (f) |

DETECTION

The same procedure as used in Example 1 was followed.

RESULTS

As mentioned above, the base sequence of the tdh gene of *Vibrio parahaemolyticus* has already been determined. Therefore, the size of the uncleotide amplified by the PCR using the oligonucleotides, or primers, of the present invention can be estimated. Thus, when primers (c) and (d), (e) and (d), or (e) and (f) are used, the oligonucleotide amplified is expected to be 373, 199, or 251 bases long, respectively. When the size of the amplified uncleotide was in agreement with such estimated value, it was judged that each primer contributed to correct amplification of the target region in the tdh gene. The results thus obtained with 264 strains of *Vibrio parahaemolyticus* and 98 strains of other Vibrio species are shown in Tables 1–15. As can be seen from Tables 1–15, the three primer combinations each could correctly detect tdh gene-containing strains alone among the strains of *Vibrio parahaemolyticus* and Vibrio species tested.

EXPERIMENT 2

To ascertain whether the results obtained in Experiment 1 were selective for tdh gene-carrying strains of *Vibrio parahaemolyticus* and Vibrio species, diarrhea-causing microorganisms other than *Vibrio parahaemolyticus* but generally included as targets in clinical laboratory testing were tested for comparison in the same manner as in Example 1.

The results obtained are shown in Tables 16 and 17. In some microorganisms, amplified nucleotide fragments, which were presumably byproducts of the PCR, were detected.

However, they all differed in size from the nucleotide fragment anticipated from the sequence of the tdh gene. If these diarrhea-causing microorganisms had the same tdh gene as that of *Vibrio parahaemolyticus*, a nucleotide fragment identical in size as that detected in Experiment 1, namely 373, 199 or 251 bases long, would have been detected. It is therefore evident that the amplified nucleotides observed for said certain diarrhea-causing microorganisms were not the products resulting from recognition of the tdh gene of *Vibrio parahaemolyticus* but that those stains of *Vibrio parahaemolyticus* and Vibrio species that have the tdh gene can be readily detected in distinction from other diarrhea-causing microorganisms.

EXAMPLE 3

Detection of the trh1 gene of *Vibrio parahaemolyticus*

EXPERIMENT 1

Sample preparation, primer synthesis, PCR and detection were carried out in the same manner as in Example 1 except that the primers (g) and (h) defined in claim 3 were used.

When the primers (g) an (h) of the invention are used, it is expected that a nucleotide 211 bases long be amplified. When the size of the nucleotide amplified was in agreement with said estimated value, it was judged that each primer contributed to correct amplification of the target region in the trh1 gene. The results obtained with 264 strains of *Vibrio parahaemolyticus* and 98 strains of Vibrio species are shown in Tables 1–15. As can be seen in Tables 1–15, the primer combination could correctly detect only those strains having the trh1 gene among the strains of *Vibrio parahaemolyticus* and Vibrio species.

EXPERIMENT 2

To ascertain whether the results obtained in Experiment 1 were selective for the trh1 gene-containing strains of *Vibrio parahaemolyticus* and Vibrio species, diarrhea-causing microorganisms other than *Vibrio parahaemolyticus* but generally involved as targets in clinical laboratory testing were tested for comparison by the same method as used in Example 1.

The results obtained are shown in Tables 16 and 17. With some microorganisms, amplified nucleotide fragments, which were presumably byproducts of the PCR, were detected.

However, none of them was identical in size with the nucleotide fragment anticipated from the sequence of the trh1 gene. If these diarrhea-causing microorganisms had the same trh1 gene as that of *Vibrio parahaemolyticus*, the same, 211-base-long nucleotide fragment as detected in Experiment 1 would have been detected. Therefore, it is evident that the amplified nucleotides found in said certain diarrhea-causing microorganisms were by no means the products of recognition of the trh1 gene of *Vibrio parahaemolyticus* but that trh1 gene-containing strains of *Vibrio parahaemolyticus* can be readily detected in distinction from other diarrhea-causing microorganisms.

TABLES 1–17

Notes to the above Tables:
(1) in column "trh": strain having the type 1 trh gene.
(2) in column "trh": strain having the type 2 trh gene.
(−) in column "trh": strain having no trh gene.
(+) in column "tdh": strain having the tdh gene.
(−) in column "tdh": strain having no tdh gene.
(O) in column "Primer combination": The amplified nucleotide had the same size as the expected value.
(●) in column "Primer combination": The amplified nucleotide, though detected, had a size different from the expected value.
(−) in column "Primer combination": No amplified nucleotide was detected.

The strains shown in Tables 1–15 were obtained from: Department of Microbiology, Faculty of Medicine, Kyoto University.

The strains shown in Tables 16 an 17 were obtained from: ATCC (American Type Culture collection), JCM (Japanese Collection of Microorganisms, RIKEN Institute of Physical and Chemical Research), and IFO (Institute for Fermentation, Osaka).

EXAMPLE 4

Detection of the LT gene of toxigenic *Escherichia coli*

EXPERIMENT 1

SAMPLE PREPARATION

For screening toxigenic strains of *Escherichia coli*, 492 clinical isolates from patients with diarrhea, shown in Tables 18–30, were used. These strains were gifts from the Department of Microbiology (chief: Prof. Y. Takeda), Faculty of Medicine, Kyoto University. Each strain was inoculated into an appropriate medium and cultured overnight at 37° C. Under aerobic conditions. Cells were recovered from the medium (1.5 ml) by centrifugation, washed once with 10 mM Tris-hydrochloride (pH 7.5) and then subjected to lysis by suspending them in 0.5 ml of a 1 mg/ml lysozyme solution in the same buffer at 37° C. for 10 minutes. A phenol-chloroform mixture (mixing ratio 1:1) saturated with the above-mentioned buffer was added to the lysate solution, followed by thorough stirring. After centrifugation, the upper layer was recovered and subjected to ethanol treatment for precipitating nucleic acid components. The precipitate was dissolved in 1 ml of the above-mentioned buffer and the solution was used as a sample.

PRIMER SYNTHESIS

Based on the base sequence of the LT gene of heat-labile enterotoxin-producing *Escherichia coli* [Yamamoto, T., T. Tamura and T. Yokota (1984): Primary structure of heat-labile enterotoxin produced by *Escherichia coli* pathogenic for humans. J. Biol. Chem., 259: 5037–5044 and Yamamoto, T., T. Gojobori and T. Yokota (1987): Evolutionary origin of pathogenic determinants in enterotoxigenic *Escherichia coli* and *Vibrio cholerae* O1. J. Bacteriol., 169: 1352–1357], the sequences (a), (b), (c), (d) and (e) shown in claim 5 were selected, and oligonucleotides having the same sequences as those selected were chemically synthesized. The chemical synthesis was carried out by the β-cyanoethylphosphamidite method using a Cylcone Plus DNA synthesizer (Milligen/BioResearch). The oligonucleotides synthesized were purified by high-performance liquid chromatography using a C18 reversed phase column.

PCR

A reaction mixture (30 µl) was prepared by adding, to 3 µl of the sample solution mentioned above, 16.05 of sterile water, 3 µl of 10× reaction buffer, 4.8 µl of dNTP solution, 1.5 µl of primer (1), 1.5 µl of primer (2), and 0.15 µl of thermostable DNA polymerase. Mineral oil (50 µl; Sigma) was layered on said reaction mixture placed in a container. The solutions used in preparing the reaction mixture and the combination of primers (1) and (2) were as shown below.

10× Reaction buffer: 500 mM KCl, 100 mM Tris-HCl (pH 8.3), 15 mM $MgCl_2$, 0.1% (w/v) gelatin.

dNTP solution: containing dATP, dCTP, dGTP and dTTP each at a concentration of 1.25 mM.

Primers (1) and (2): Each was an aqueous solution of each product chemically synthesized and purified as mentioned above (concentration 5 ODU/ml).

Primer combination: The following three combinations of the chemically synthesized and purified products mentioned above were used.

| Primer (1) | Primer (2) |
|---|---|
| (a) | (b) |
| (c) | (d) |
| (e) | (d) |

Thermostable DNA polymerase: Taq DNA polymerase (5 units/ml; Perkin Elmer Cetus).

The reaction conditions were the same as in Example 1.

DETECTION

For detecting the amplified nucleotide fragment in the reaction mixture, agarose gel electrophoresis was performed under the same conditions as used in Example 1 except that the agarose gel had a gel concentration of 3% (w/v).

RESULTS

As mentioned above, the base sequence of the LT gene has already been determined. Therefore, the size of the nucleotide amplified by the PCR using the oligonucleotides, or primers, of the invention can be estimated. Thus, the primer combination (a)+(b), (c)+(d) and (e)+(d) are expected to give amplified nucleotides of 589, 550 and 264 bases in size, respectively. When the size of the amplified nucleotide was in agreement with the estimated value, it was judged that each primer contributed to correct amplification of the target region in the LT gene. The results of testing of 492 clinical isolates of *Escherichia coli* for nucleotide amplification by the above method are shown in Tables 18–30. In Tables 18–30, the symbol + in the column "primer" means that the size of the amplified nucleotide agreed with the estimated value while the symbol − means that no amplified nucleotide was detected at all.

As shown in the tables, the PCR conducted with each primer combination resulted in nucleotide amplification only in the strains having the LT gene (those marked with +, 2+ or w in the LT gene column in Tables 18–30). Furthermore, each amplified nucleotide had the same nucleotide size as estimated. It is therefore evident that the oligonucleotides, namely primers, of the invention could contribute to correct amplification of the target region in the LT gene of toxigenic *Escherichia coli*.

EXPERIMENT 2

TO ascertain whether the results obtained in Experiment 1 were selective for LT-producing strains of *Escherichia coli*, microorganisms other than *Escherichia coli* but generally included as targets in clinical laboratory testing were also tested for comparison.

The method used was the same as shown in Example 1 except that, for *Clostridium perfringens*, *Campylobacter jejuni*, *Campylobacter coli*, *Bacteroides flagilis*, *Bacteroides vulgatus* and *Lactobacillus acidophilus*, samples applicable to the PCR method were prepared by overnight culture at 37° C. under anaerobic conditions. As shown in Tables 31 and 32, 50 microbial strains were cultured for preparing samples. Further, a 1 µg/ml solution of human placenta DNA was prepared and also subjected to PCR.

The results obtained are shown in Tables 31 and 32. None of the three primer combinations used caused amplification of DNA of various bacteria other than pathogenic *Escherichia coli*. It is therefore declarable that the oligonucleotides, namely primers, of the invention react selectively with heat-labile enterotoxin-producing *Escherichia coli* alone.

On the other hand, it is clear that, in accordance with the invention, no cross reaction occurs with CT-producing *Vibrio cholerae* (in Table 32, *V. cholerae* 01 ctx+). Immunologically, CT and LT have common antigenicity, as mentioned above, and any immunological means cannot distinguish them from each other. On the Contrary, the method according to the invention can distinctly detect LT-producing *Escherichia coli* alone, hence can be considered to show improved reliability as compared with the prior art methods.

The agarose gel electrophoresis described herein in the examples, when carried out under the conditions mentioned above, can distinguish nucleotides of 100 or less base pairs in size from each other when they differ in size by 5 to 10 base pairs, and nucleotides of 100 to 500 base pairs in size from each other when they differ in size by 10 to 20 base pairs. The precision of nucleotide size measurement can be improved by using acrylamide, for instance, as the gel and, by doing so, the reliability in the selective detection of the LT gene can probably be further improved.

TABLE 18–TABLE 32

Notes to the above tables:
(+) in column "LT gene": The strain has the LT gene.
(2+) in column "LT gene": The strain has the LT gene.
(w) in column "LT gene": The strain has the LT gene.
(−) in column "LT gene": The strain has no LT gene.
(+) in column "Primer": The size of the amplified nucleotide is in agreement with the estimated value.
(w) in column "Primer": The size of the amplified nucleotide is in agreement with the estimated value but the extent of amplification is somewhat weak.
(−) in column "Primer": No nucleotide amplification was noted at all.
The strains shown in Tables 18-30 were obtained from:
Department of Microbiology, Faculty of Medicine, Kyoto University.
The strains Nos. 1-39 shown in Tables 31 and 32 were obtained from:
ATCC (American Type Culture Collection),
JCM (Japanese Collection of Microorganisms, RIKEN Institute of Physical and Chemical Research), and
IFO (Institute for Fermentation, Osaka).
The strains Nos. 4–50 shown in Table 32 were obtained from:
Department of Microbiology, Faculty of Medicine, Kyoto University.
The strains No. 51 shown in Table 32 was obtained from:
Takara Shuzo Co., Ltd.

EXAMPLE 5

Detection of the RTh or RTp gene of toxigenic *Escherichia coli*

EXPERIMENT 1

SAMPLE PREPARATION

As shown in Tables 33-54, a total of 492 strains of pathogenic *Escherichia coli* as isolated from patients with diarrhea were used. Each strain was inoculated into an appropriate enrichment medium and cultured overnight at 37° C. under aerobic conditions. Each culture broth was diluted with 10 mM Tris-hydrochloride buffer (pH 7.5) (hereinafter, TE buffer), heat-treated at 95° C. for 10 minutes and then centrifuged. The supernatant was used as a sample.

PRIMER SYNTHESIS

Based on the base sequence of the STh or STp gene of toxigenic *Escherichia coli* [Moseley, S. L., et al., Infect. Immun., 39, 1167–1174 (1983)], the sequences (a) and (b) defined in claim 7 were selected, and oligonucleotides having the same sequences as those selected were chemically synthesized. The chemical synthesis was carried out by the β-cyanoethylphosphamidite method using a Cyclone Plus DNA synthesizer (Milligen/BioResearch). The oligonucleotides synthesized were purified by high-performance liquid chromatography using a C18 reversed phase column.

PCR

The procedure of Example 4 was followed.
The combination of primers (1) and (2) was as follows.
Primers (1) and (2): Each an aqueous solution of the chemically synthesized and purified product mentioned above (concentration 5 OD/ml).
Primer combination: primer (1): sequence (a), primer (2): sequence (b).
Thermostable DNA polymerase: Taq DNA polymerase (5 units/ml; Perkin Elmer Cetus).
The reaction conditions were the same as used in Example 1.

DETECTION

The procedure of Example 4 was followed.

RESULTS

As mentioned above, the base sequence of the STh or STp gene of toxigenic *Escherichia coli* has already been determined and, therefore, the size of the nucleotide to be amplified by he PCR using the oligonucleotides, namely primers, of the invention can readily be estimated.

Thus, when the combination of primers (a) and (b) is used, a nucleotide of 120 bases in size is expected to be amplified. When the size of the amplified nucleotide was in agreement with said estimated value, it was judged that each primer could contribute to correct amplification of the target region in the STh or STp gene. This judgment was indicated by "+" in Tables 33–54. When no nucleotide amplification was noted, this result was indicated by "−".

The results obtained with 492 strains of pathogenic *Escherichia coli* are shown in Tables 33–54. As can be seen in Tables 33–54, the primers used could correctly detect only those strains shown to have the STh or STp gene by the colony hybridization technique among the pathogenic *Escherichia coli* strains tested.

EXPERIMENT 2

To ascertain whether the results obtained in Experiment 1 were selective for pathogenic *Escherichia coli* strains having the STh or STp gene, diarrhea-causing microorganisms other than pathogenic *Escherichia coli* but generally included as targets in clinical laboratory testing were also tested for comparison.

The procedure of Example 1 was followed except for the method of sample preparation, which is mentioned below.

SAMPLE PREPARATION

Each of the strains shown in Tables 55–57 was inoculated into an appropriate enrichment medium and cultured overnight at 37° C. under aerobic or anaerobic conditions (strains cultured under anaerobic conditions were Clostridium perfringens, *Campylobacter jejuni, Bacteroides flagilis, Bacteroides vulgatus* and *Lactobacillus acidophilus*).

Cells were recovered from each culture broth (0.5 ml) by centrifugation and washed once with TE buffer. To the cells were added an N-acetylmuramidase solution in 50 mM phosphate buffer (pH 7.5) and an achromopeptidase solution to final concentrations of 50 µg/ml and 1 mg/ml, respectively, and the mixture was treated at 37° C. for 10 minutes for causing lysis. A phenolchloroform mixture (mixing ratio 1:1) saturated with TE buffer was added to the lysate, followed by thorough stirring.

After centrifugation, the upper layer liquid was recovered and subjected to ethanol treatment for causing precipitation of nucleic acid components. The precipitate was dissolved in 1 ml of TE buffe and the solution was used as a sample. Further, a 1 µg/ml solution of human placenta DNA was prepared and also subjected to PCR.

RESULTS

As shown in Tables 55–57, the primers used did not cause amplification of any of the various DNAs, including DNAs derived from diarrhea-causing microorganisms. Therefore, it can be declared that the oligonucleotides, namely primers, of the invention react selectively with pathogenic *Escherichia coli* strains having the STh or STp gene.

The agarose gel electrophoresis described herein, when carried out under the conditions mentioned above, can distinguish nucleotides of 100 base pairs or less in size from each other when they differ in size by 5 to 10 base pairs, and nucleotides of 100 to 500 base pairs in size from each other when they differ in size by 10 to 20 base pairs.

The precision of nucleotide size determination can be improved by using acrylamide, for instance, as the gel and, by doing so, the reliability in the selective detection of the STh or STp gene can probably be further improved.

EXAMPLE 6

Detection of the STh gene of toxigenic *Escherichia coli*

EXPERIMENT 1

SAMPLE PREPARATION

Samples were prepared by the same technique as used in Example 5.

PRIMER SYNTHESIS

Based on the base sequence of the STh gene of toxigenic *Escherichia coli* [Moseley, S. L., et al.; Infect. Immun., 39, 1167–1174 (1983)], the sequences (c), (d) and (e) shown in claim 8 were selected, and oligonucleotides having the same sequences as those selected were chemically synthesized. The chemical synthesis and purification of the oligonucleotides synthesized were performed in the same manner as in Example 1.

PCR

The same technique as used in Example 5 was used except that the following primer combinations were used.

| Primer (1) | Primer (2) |
|---|---|
| (c) | (e) |
| (d) | (e) |

DETECTION

The technique used in Example 5 was used.

RESULTS

As mentioned above, the base sequence of the STh gene of toxigenic *Escherichia coli* has already been determined. Therefore, the size of the nucleotide to be amplified by the PCR using the oligonucleotides, or primers, of the invention can be readily estimated.

Thus, when the primer combinations (c)+(e) and (d)+(e) are used, the nucleotides amplified are expected to have the sizes of 137 and 127 bases, respectively. When the size of the amplified nucleotide was in agreement with either of these estimated values, it was judged that each primer could contribute to correct amplification of the target region in the STh gene. This judgment was indicated by "+" in Tables 33–54. When no nucleotide amplification was noted, "−" was given in the tables. The results obtained with 492 strains of pathogenic *Escherichia coli* are shown in Tables 33–54.

As can be seen in Tables 33–54, each of the two primer combinations could correctly detect only those strains of pathogenic *Escherichia coli* that had been shown to have the STh gene by the colony hybridization technique.

EXPERIMENT 2

To ascertain whether the results obtained in Experiment 1 were selective for pathogenic *Escherichia coli* strains having the STh gene, diarrhea-causing microorganisms other than pathogenic Escherichia coli but generally included as targets in clinical laboratory testing were tested for comparison by the same method as used in Example 1.

As shown in Tables 55–57, either of the primer combinations did not cause DNA amplification for any of various DNAs including the DNAs of the diarrhea-causing microorganisms. Therefore, it can be declared that the oligonucleotides, namely primers, of the invention react selectively only with pathogenic *Escherichia coli* strains having the STh gene.

EXAMPLE 7

Detection of the STp gene of toxigenic *Escherichia coli*

EXPERIMENT 1

SAMPLE PREPARATION

Samples were prepared in the same manner as in Example 5.

PRIMER SYNTHESIS

Based on the base sequence of the STp gene of toxigenic *Escherichia coli* [Moseley, S. L., et al., Infect. Immun., 39, 1167–1174 (1983)], the sequences (f), (g) and (h) shown in claim 9 were selected, and oligonucleotides having the same sequences as those selected were chemically synthesized. The chemical synthesis and purification of the oligonucleotides synthesized were performed as described in Example 1.

PCR

The method of Example 5 was used except that the following primer combinations were used.

| Primer (1) | Primer (2) |
|---|---|
| (f) | (h) |
| (g) | (h) |

DETECTION

The method of Example 5 was used.

RESULTS

As mentioned above, the base sequence of the STp gene of toxigenic *Escherichia coli* has already been determined. Accordingly, the size of the nucleotide to be amplified by the PCR using the oligonucleotides, or primers, of the invention can readily be estimated.

Thus, when the primer combinations (f)+(h) and (g)+(h) are used, nucleotides of 143 and 123 bases in size, respectively, are expected to be amplified. When the size of the amplified nucleotide was in agreement with such estimated value, it was judged that each primer could contribute to correct amplification of the target region in the STh gene. This judgment was indicated by "+" in tables 33–54. When no nucleotide amplification was noted, "–" was given. The results obtained with 492 strains of pathogenic *Escherichia coli* are shown in Tables 33–54.

As can be seen in Tables 33–54, each of the two primer combinations could correctly detect only those pathogenic *Escherichia coli* strains that had been shown to have the STp gene by the colony hybridization technique.

EXPERIMENT 2

To ascertain whether the results obtained in Experiment 1 were selective for pathogenic *Escherichia coli* strains having the STp gene, diarrhea-causing microorganisms other than pathogenic *Escherichia coli* but generally included as targets in clinical laboratory testing were tested for comparison by the same technique as used in Example 1.

As shown in Tables 55–57, either of the primer combinations did not cause DNA amplification for any of various DNAs, such as DNAs of diarrhea-causing microorganisms. Therefore, it can be declared that the oligonucleotides, namely primers, of the invention selectively react only with pathogenic *Escherichia coli* strains having the STp gene.

TABLES 33–66

EXAMPLE 8

Detection of the entA gene of *Staphylococcus aureus*

EXPERIMENT 1

SAMPLE PREPARATION

A total of 157 stains of *Staphylococcus aureus*, as shown in Tables 58–63, were used. These were food poisoning case strains isolated from patients' feces or vomits, causative foods, etc. Each strain was inoculated into brain heart infusion medium (BRL) and shake-cultured overnight at 37° C. under aerobic conditions. Each culture broth was diluted with 10 mM Tris-hydrochloride buffer (pH 7.5) (TE buffer), heat-treated at 95° C. for 10 minutes and then centrifuged. The supernatant was used as a sample.

PRIMER SYNTHESIS

Based on the base sequence of the entA gene of *Staphylococcus aureus* [Betley, M. J. and Mekalanos, J. J., J. Bacteriol, 170, 34–41 (1988)], the sequences (a) to (f) shown in claim 11 were selected, and oligonucleotides having the same sequences as those selected were chemically synthesized. The chemical synthesis was carried out by the β-cyanoethylphosphamidite method using a Cyclone Plus DNA synthesizer (Milligen/BioResearch). The oligonucleotides synthesized were purified by high-performance liquid chromatography using a C18 reversed phase column.

PCR

The PCR was conducted by the same method as used in Example 4.

The following primer combinations (1)+(2) were used.

Primers (1) and (2): Each an aqueous solution of the chemically synthesized and purified product mentioned above (concentration 5 OD/ml).

Primer combinations: The above-mentioned chemically synthesized and purified products were used in the following combinations.

| Primer (1) | Primer (2) |
|---|---|
| (a) | (e) |
| (a) | (f) |
| (b) | (d) |
| (b) | (e) |
| (b) | (f) |
| (c) | (d) |
| (c) | (e) |
| (c) | (f) |

Thermostable DNA polymerase: Taq DNA polymerase (5 units/ml; Perkin Elmer Cetus).

The reaction conditions were as mentioned in Example 1.

DETECTION

The procedure of Example 4 was followed.

Reversed passive latex agglutination (RPLA) test

A commercial RPLA kit for detecting *Staphylococcus aureus* neterotoxin (SET-RPLA "Seiken", purchased from Denka Seiken) was used. Samples were prepared and tested as described in the manual attached to the kit.

However, in preparing samples to be submitted to testing, some conditions were modified so that enterotoxin could be produced in sufficient amounts. Thus, while the manual teaches that shake culture should be conducted in brain heart infusion medium or the like at 37° C. for 18–20 hours, the culture in this example was carried out in brain heart infusion medium (BRL) at 37° C. for 48 hours with shaking at 100 rpm. Each culture supernatant was submitted to the RPLA test.

RESULTS

As mentioned above, the base sequence of the entA gene of *Staphylococcus aureus* has already been determined. Accordingly, the size of the nucleotide to be amplified by the PCR using each pair of the oligonucleotides, or primers, of the invention can be readily estimated.

Thus, when the combination of primers (a) and (e) is used, a nucleotide of 513 bases (or 513 base pairs) in size is expected to be amplified.

For all the primer combinations shown above, the sizes (estimated values) of the nucleotides to be amplified are summarized below.

Summary of sizes (estimated values) of amplified nucleotides

|  | Primer (1) | | |
|---|---|---|---|
|  | (a) | (b) | (c) |
| Primer (2) |  |  |  |
| (d) | — | 274 | 236 |
| (e) | 513 | 390 | 352 |
| (f) | 546 | 423 | 385 |
|  |  |  | (in bases) |

When the size of the nucleotide amplified was in agreement with such estimated value, it was judged that each primer could contribute to correct amplification of the target region in the entA gene. This judgment was indicated by "+" in Tables 58–63. When no nucleotide amplification was noted, "–" was given.

The results obtained with 157 strains of *Staphylococcus aureus* are shown in Tables 58–63. As can be seen in the tables, all the primer combinations shown in the tables caused gene amplification only when the strain in question was shown to be an enterotoxin A-producing strain by the RPLA method. This indicates that the primer combinations correctly caused amplification of the entA gene and thereby correctly detected *Staphylococcus aureus* strains having the entA gene.

Other combinations that are not shown in the tables also gave similar test results.

EXPERIMENT 2

To ascertain whether the results obtained in Experiment 1 were selective for *Staphylococcus aureus* strains having the entA gene, the primers of the invention were investigated as to whether they were reactive with the genes of food poisoning- or diarrhea-causing microorganisms other than *Staphylococcus aureus* but generally included as targets in clinical laboratory testing. The procedure used was the same as shown in Experiment 1 except for the method of sample preparation.

SAMPLE PREPARATION

Each of the strains shown in the tables was inoculated into an appropriate enrichment medium and cultured overnight at 37° C. under aerobic or anaerobic conditions. (The strains cultured under anaerobic conditions were *Clostridium perfringens, Campylobacter jejuni, Bacteroides flagilis, Bacteroides vulgatus* and *Lactobacillus acidophilus*.)

Cells were recovered from each culture broth (0.5 ml) by centrifugation and washed once with TE buffer. To these cells were added an N-acetylmuramidase in 50 mM phosphate buffer (pH 7.5) and an achromopeptidase solution to final concentrations of 50 µg/ml and 1 mg/ml, respectively. The mixture was treated at 37° C. for 10 minutes for causing lysis. A phenol-chloroform mixture (mixing ratio 1:1) saturated with TE buffer was added to the lysate, followed by thorough stirring.

After centrifugation, the upper layer liquid was recovered and subjected to ethanol treatment for precipitating nucleic acid components. This precipitate was dissolved in 1 ml of TE buffer and the solution was used as a sample. Further, a 1 µg/ml solution of human placenta DNA was also prepared and submitted to PCR in the same manner.

RESULTS

As shown in Table 64, the primers used did not cause DNA amplification for any of the various DNAs tested, including food poisoning-causing microorganisms. Therefore, it can be declared that the oligonucleotides, namely primers, of the invention selectively react only with *Staphylococcus aureus* strains having the entA gene. The remaining primer combinations other than those shown in Table 64 also gave similar test results.

The agarose gel electrophoresis used herein in the examples, when carried out under the conditions mentioned above, can distinguish nucleotides of 100 base pairs or less in size from each other when they differ in size by 5 to 10 base pairs, and nucleotides of 100 to 500 base pairs in size from each other when they differ in size by 10 to 20 base pairs.

Furthermore, the precision of nucleotide size determination can be improved by using acrylamide, for instance, as the gel and, by doing so, the reliability in the selective detection of the entA gene can probably be further improved.

EXAMPLE 9

Detection of the entB gene of *Staphylococcus aureus*

EXPERIMENT 1

SAMPLE PREPARATION

Samples were prepared in the same manner as in Example 8.

PRIMER SYNTHESIS

Based on the base sequence of the entB gene of *Staphylococcus aureus* [Ranelli, D. M. et al., Proc. Natl. Acad. Sci. U.S.A., 82, 5850–5854 (1985)], the sequences (g) to (l) shown in claim 12 were selected, and oligonucleotides having the same sequences as those selected were chemically synthesized. The chemical synthesis and purification of the oligonucleotides synthesized were performed in the same manner as in Example 8.

PCR

The PCR was carried out in the same manner as in Example 8 except that the following primer combinations were used.

| Primer (1) | Primer (2) |
|---|---|
| (g) | (j) |

-continued

| Primer (1) | Primer (2) |
|---|---|
| (g) | (k) |
| (h) | (j) |
| (h) | (k) |
| (h) | (l) |
| (i) | (k) |
| (i) | (l) |

DETECTION

The method described in Example 4 was used.

Reversed passive latex agglutination (RPLA) test

The method described in Example 8 was used.

RESULTS

As mentioned above, the base sequence of the entB gene of *Staphylococcus aureus* has already been determined. Accordingly, the size of the nucleotide to be amplified by the PCR using the oligonucleotides, namely primers, of the invention can be readily estimated.

Thus, when the primer combination (g)+(j) is used, a nucleotide of 304 bases (or 304 base pairs) is expected to be amplified.

For all the primer combinations used in this example, the sizes (estimated values) of the nucleotides to be amplified are summarized below.

Summary of the sizes (estimated values) of the nucleotides to be amplified

| | Primer (1) | | |
|---|---|---|---|
| | (g) | (h) | (i) |
| Primer (2) | | | |
| (j) | 304 | 241 | — |
| (h) | 391 | 328 | 197 |
| (l) | — | 419 | 288 |
| | | | (in bases) |

When the size of the nucleotide amplified was in agreement with such estimated value, it was judged that each primer contributed to correct amplification of the target region in the entB gene. This judgment was indicated by "+" in Tables 58–63. When no nucleotide amplification was noted, this fact was indicated by "−".

The results obtained with 157 strains of *Staphylococcus aureus* are shown in Tables 58–63. As can be seen in the tables, all the primer combinations shown caused gene amplification only for those strains that had been shown to be enterotoxin B producers by the RPLA method. Thus it is clear that said primer combinations can cause correct amplification of the entB gene and thus correctly detect *Staphylococcus aureus* strains having the entB gene.

The remaining combinations other than those shown in the tables also gave similar results.

EXPERIMENT 2

To ascertain whether the results obtained in Experiment 1 were selective for *Staphylococcus aureus* strains having the entB gene, the primers of the invention were examined as to whether they reacted with the genes of food poisoning- or diarrhea-causing microorganisms other than *Staphylococcus aureus* but generally included as targets in clinical laboratory testing were also tested by following the procedure of Example 8.

As shown in Table 64, the primers used did not cause DNA amplification for any of various DNAs, such as food poisoning-causing microorganisms. Therefore, it can be declared that the oligonucleotides, namely primers, of the invention selectively react only with *Staphylococcus aureus* strains having the entB gene. The remaining primer combinations other than those shown in the tables also gave similar test results.

EXAMPLE 10

Detection of the entC gene of *Staphylococcus aureus*

EXPERIMENT 1

SAMPLE PREPARATION

Samples were prepared in the same manner as in Example 8.

PRIMER SYNTHESIS

Based on the base sequence of the entC gene of *Staphylococcus aureus* [Betley, M. J. and Mekalanos, J. J., J. Bacteriol, 170, 34–41 (1988)], the base sequences (m) to (r) shown in claim 13 were selected, and oligonucleotides having the same sequences as those selected were chemically synthesized. The chemical synthesis and purification of the oligonucleotides synthesized were performed in the same manner as in Example 8.

PCR

The PCR procedure of Example 4 was followed except that the following primer combinations were used.

| Primer (1) | Primer (2) |
|---|---|
| (m) | (q) |
| (m) | (r) |
| (n) | (q) |
| (n) | (r) |
| (o) | (q) |
| (o) | (r) |
| (p) | (q) |
| (p) | (r) |

DETECTION

The detection procedure of Example 4 was followed.

Reversed passive latex agglutination (RPLA) test

The RPLA procedure of Example 8 was followed.

RESULTS

As mentioned above, the base sequence of the entC gene of *Staphylococcus aureus* has already been determined. Therefore, the size of the nucleotide to be amplified by the PCR using the oligonucleotides, or primers, of the invention can be readily estimated.

Thus, when the combination of primers (m) and (q) is used, a nucleotide of 282 bases (or 282 base pairs) in size is expected to be amplified.

For all the primer combinations of the invention as used in this example, the sizes (estimated values) of the respective nucleotides to be amplified are shown below.

Summary of sizes (estimated values) of amplified nucleotides

|  | Primer (1) | | | |
| --- | --- | --- | --- | --- |
|  | (m) | (n) | (o) | (p) |
| Primer (2) | | | | |
| (q) | 282 | 274 | 236 | 99 |
| (r) | 478 | 420 | 342 | 295 |
| | | | | (in bases) |

When the size of the nucleotide amplified was in agreement with such an estimated value, it was judged that each primer contributed to correct amplification of the target region in the entC gene. This judgement is indicated by "+" in Tables 58–63, while no nucleotide amplification is indicated by "−".

The results obtained with 157 strains of *Staphylococcus aureus* are shown in Tables 58–63. As can be seen from the tables, all the primer combinations shown caused gene amplification only for those strains that had been shown to be enterotoxin C-producing strains by the RPLA technique. They caused correct amplification of the entC gene and correctly detected *Staphylococcus aureus* strains having the entC gene.

The remaining combinations other than those shown in the tables also gave similar results.

EXPERIMENT 2

To ascertain whether the results obtained in Experiment 1 were selective for *Staphylococcus aureus* strains having the entC gene, food poisoning- or diarrhea-causing microorganisms other than *Staphylococcus aureus* but generally includes as targets in clinical laboratory testing were studied, by the same technique as used in Example 1, as to whether the primers of the invention react with the genes of said microorganisms.

As shown in Table 64, the primer combinations used did not cause DNA amplification for any of various DNAs, including DNAs of food poisoning-causing microorganisms. Therefore, it can be declared that the oligonucleotides, or primers, of the invention selectively react only with *Staphylococcus aureus* strains having the entC gene. The remaining primer combinations other than those shown in the Table also gave similar results.

EXAMPLE 11

Detection of the entD gene of *Staphylococcus aureus*

EXPERIMENT 1

SAMPLE PREPARATION

Samples were prepared in the same manner as in Example 8.

PRIMER SYNTHESIS

Based on the base sequence of the entD gene of *Staphylococcus aureus* [Betley, M. J. and Mekalanos, J. J., J. Bacteriol, 170, 34–41 (1988)], the base sequences (s) to (z) shown in claim 14 were selected, and oligonucleotides having the same sequences as those selected were chemically synthesized. The chemical synthesis and purification of the oligonucleotides synthesized were performed in the same manner as in Example 8.

PCR

The PCR procedure of Example 4 was followed except that the following primer combinations were used.

| Primer (1) | Primer (2) |
| --- | --- |
| (s) | (w) |
| (s) | (y) |
| (s) | (z) |
| (t) | (w) |
| (t) | (x) |
| (t) | (z) |
| (u) | (x) |
| (u) | (y) |
| (v) | (y) |
| (v) | (z) |

DETECTION

The technique described in Example 4 was used.

Reversed passive latex agglutination (RPLA) test

The RPLA procedure of Example 8 was followed.

As mentioned above, the base sequence of the entD gene of *Staphylococcus aureus* has already been determined. Therefore, the size of the nucleotide to be amplified by the PCR using the oligonucleotides, or primers, of the invention can be readily estimated.

Thus, when the combination of primers (s) and (w) is used, a nucleotide of 211 bases (or 211 base pairs) in size is expected to be amplified.

For all the primer combinations of the invention as used in this example, the sizes (estimated values) of the respective nucleotides to be amplified are shown below.

Summary of sizes (estimated values) of amplified nucleotides

|  | Primer (1) | | | |
| --- | --- | --- | --- | --- |
|  | (s) | (t) | (u) | (v) |
| Primer (2) | | | | |
| (w) | 211 | 142 | — | — |
| (x) | — | 226 | 125 | — |
| (y) | 474 | 405 | 304 | 199 |
| (z) | 501 | 432 | — | 226 |
| | | | | (in bases) |

When the size of the nucleotide amplified was in agreement with such an estimated value, it was judged that each primer contributed to correct amplification of the target region in the entD gene. This judgement is indicated by "+" in Tables 58–63, while no nucleotide amplification is indicated by "–".

The results obtained with 157 strains of *Staphylococcus aureus* are shown in Tables 58–63. As can be seen from the tables, all the primer combinations shown caused gene amplification only for those strains that had been shown to be enterotoxin D-producing strains by the RPLA technique. They caused correct amplification of the entD gene and correctly detected *Staphylococcus aureus* strains having the entD gene.

The remaining combinations other than those shown in the tables also gave similar results.

EXPERIMENT 2

To ascertain whether the results obtained in Experiment 1 were selective for *Staphylococcus aureus* strains having the entD gene, food poisoning- or diarrhea-causing microorganisms other than *Staphylococcus aureus* but generally includes as targets in clinical laboratory testing were studied, by the same technique as used in Example 1, as to Whether the primers of the invention react with the genes of said microorganisms.

As shown in Table 64, the primer combinations used did not cause DNA amplification for any of various DNAs, including DNAs of food poisoning-causing microorganisms. Therefore, it can be declared that the oligonucleotides, or primers, of the invention selectively react only with *Staphylococcus aureus* strains having the entD gene. The remaining primer combinations other than those shown in the Table also gave similar results.

By using, in accordance with the invention, the PCR method and the primers the targets of which are genes most closely associated with pathogenicity, it is possible, in detecting bacteria having such genes, namely (1) *Vibrio parahaemolyticus* and Vibrio species, (2) toxigenic *Escherichia coli*, (3) toxigenic *Escherichia coli* having the STh or STp gene and (4) *Staphylococcus aureus*, to attain high detection sensitivity as a result of gene amplification and, at the same time, high selectivity as a result of the reaction being defined by two or more primers.

Since the detection sensitivity is high, samples are needed only in small amounts, and this makes sample pretreatment simple and easy. In the examples described herein, the reaction time was 3 hours and the time for detection procedure was as short as 30 minutes. The detection may be made easily by using a simple apparatus or instrument. Moreover, when agarose gel electrophoresis and nucleic acid staining with ethidium bromide are used for detection purposes, the detection can be carried out without labeling primers or others and, in addition, nucleic acid size determination in possible. The test results thus become highly reliable.

*Vibrio parahaemolyticus* is a pathogen ranking highest among food poisoning-causing bacteria in Japan. The health disturbance caused by this pathogen mostly lies in gastroenteritis, with diarrhea and abdominal pain as main symptoms. Among pathogenic factors of such gastroenteritis, thermostable direct hemolysin (TDH) is currently at the center of concern. *Vibrio parahaemolyticus* strains having the tdh gene, which are causative of food poisoning, can be detected selectively by taking the tdh gene coding for thermostable direct hemolysin as the target nucleotide for the primers.

Furthermore, thermostable direct hemolysin-related hemolysin (TRH), a pathogenic factor similar to TDH but essentially different therefrom, has recently been discovered and, currently, importance has been attached to the pathogenicity of TRH-producing *Vibrio parahaemolyticus* in food poisoning cases. In accordance with the invention, trh gene-containing *Vibrio parahaemolyticus* strains as food poisoning-causing organisms can be selectively detected by taking the trh gene coding for TRH as the target nucleotide to the primers.

In identifying a food poisoning-causing microorganism as pathogenic *Escherichia coli*, it is important to know whether the organism is capable of producing LT. Since no other living species has the ability to produce LT, pathogenic *Escherichia coli* can be selectively detected by taking the LT gene as the target of the primers.

Recent progress in bacteriology has revealed that organisms equally identifiable and classifiable as *Escherichia coli* include strains of various types, for example strains pathogenic to humans and strains nonpathogenic to humans.

For accurate identification of a factor causative of food poisoning or diarrhea as *Escherichia coli*, it is therefore essential to examine as to whether the *Escherichia coli* strain in question produces a pathogenic factor such as a toxin. In accordance with the invention, pathogenic *Escherichia coli* can be selectively detected in such situation by selectively detecting the gene encoding STh or STp, which is one of pathogenic factors of *Escherichia coli*.

In view of recent findings in bacteriology, detection and affirmation of a strain of *Staphylococcus aureus* as a food poisoning- or diarrhea-causing factor can hardly be regarded as accurate and correct unless said strain has been checked as to the production of the corresponding pathogenic factor, namely enterotoxin or the like, and further, in certain cases, the type of the pathogenic factor. In accordance with the invention, *Staphylococcus aureus* strains causing food poisoning, diarrhea or the like can be accurately detected by detecting the enterotoxin gene, one of the pathogenic factor genes of *Staphylococcus aureus*.

EXAMPLE 12

Detection of the entE gene of *Staphylococcus aureus*

EXPERIMENT 1

SAMPLE PREPARATION

A total of 17 strains of *Staphlylococcus aureus*, as shown in Table 65, were used. Samples were prepared in the same manner as in Example 8.

The enterotoxin producing abilities of these strains were confirmed by Reversed Passive Latex Agglutination: RPLA. The ability of FRI-326 strain was derived from a literature of American Type Culture Collection.

PRIMER SYNTHESIS

Based on the base sequence of the entB gene of *Staphylococcus aureus* [Ranelli, D. M. et al., Proc. Natl. Acad. Sci. U.S.A., 82, 5850–5854 (1985)], the sequences (a) to (f) shown in claim 15 were selected, and oligonucleotides having the same sequences as those selected were chemically synthesized. The chemical synthesis and purification of the oligonucleotides synthesized were performed in the same manner as in Example 8.

PCR

The PCR was carried out in the same manner as in Example 8 except that the following primer combinations were used.

| Primer (1) | Primer (2) |
|---|---|
| (a) | (d) |
| (a) | (f) |
| (b) | (c) |
| (b) | (e) |

DETECTION

The method described in Example 4 was used.
Reversed passive latex agglutination (RPLA) test
The method described in Example 8 was used.

RESULTS

As mentioned above, the base sequence of the entE (see) gene of *Staphylococcus aureus* has already been determined. Accordingly, the size of the nucleotide to be amplified by the PCR using the oligonucleotides, namely primers, of the invention can be readily estimated.

Thus, when the primer combination (a)+(d) is used, a nucleotide of 481 bases (or 481 base pairs) is expected to be amplified.

For all the primer combinations used in this example, the sizes (estimated values) of the nucleotides to be amplified are summarized below.

Summary of the sizes (estimated values) of the nucleotides to be amplified

|  | Primer (1) | |
|---|---|---|
| Primer (2) | (a) | (b) |
| (c) | — | 292 |
| (d) | 481 | |
| (e) | 373 | |
| (f) | 557 | — |

(in bases)

When the size of the nucleotide amplified was in agreement with such estimated value, it was judged that each primer contributed to correct amplification of the target region in the entE gene. This judgment was indicated by "+" in Table 65. When no nucleotide amplification was noted, this fact was indicated by "−".

The results obtained with 17 strains of *Staphylococcus aureus* are shown in Table 65. As can be seen in the tables, all the primer combinations shown caused gene amplification only for FRI-326 strain. Thus it is clear that said primer combinations can cause correct amplification of the entE gene and thus correctly detect *Staphylococcus aureus* strains having the entE gene.

Southern blot hybridization test was carried out by using an oligonucleotide probe having a sequence complementary to ent E (see) gene sequence. It is confirmed that the amplified DNA was derived from ent E (see) gene.

EXPERIMENT 2

To ascertain whether the results obtained in Experiment 1 were selective for Staphylococcus aureus strains having the entE gene, the primers of the invention were examined as to whether they reacted with the genes of food poisoning- or diarrhea-causing microorganisms other than *Staphylococcus aureus* but generally included as targets in clinical laboratory testing were also tested by following the procedure of Example 8.

As shown in Table 66, the primers used did not cause DNA amplification for any of various DNAs, such as food poisoning-causing microorganisms. Therefore, it can be declared that the oligonucleotides, namely primers, of the invention selectively react only with *Staphylococcus aureus* strains having the entE gene. The remaining primer combinations other than those shown in the tables also gave similar test results.

TABLE 1

|  |  |  |  |  | Primer combination | | | | |
|---|---|---|---|---|---|---|---|---|---|
| No. | Strain | Strain No. | trh | tdh | (a) + (b) | (c) + (d) | (e) + (d) | (e) + (f) | (g) + (h) |
|  | *V. parahaemolyticus* WP-1 |  | — | + |  | ○ | ○ | ○ |  |
| 1 | *V. parahaemolyticus* | AQ 3115 | — | + | — | ○ | ○ | ○ | — |
| 2 | *V. parahaemolyticus* | AQ 3170 | 1 | + | ○ | ○ | ○ | ○ | ○ |
| 3 | *V. parahaemolyticus* | AQ 3172 | 2 | — | ○ | — | — | — | — |
| 4 | *V. parahaemolyticus* | AQ 3178 | — | — | — | — | — | — | — |
| 5 | *V. parahaemolyticus* | AQ 3194 | 1 | — | ○ | — | — | — | ○ |
| 6 | *V. parahaemolyticus* | AQ 3214 | 2 | — | ○ | — | — | — | — |
| 7 | *V. parahaemolyticus* | AQ 3228 | 2 | — | ○ | — | — | — | — |
| 8 | *V. parahaemolyticus* | AQ 3230 | 2 | — | ○ | — | — | — | — |
| 9 | *V. parahaemolyticus* | AQ 3264 | — | + | — | ○ | ○ | ○ | — |
| 10 | *V. parahaemolyticus* | AQ 3295 | 1 | + | ○ | ○ | ○ | ○ | ○ |
| 11 | *V. parahaemolyticus* | AQ 3318 | — | — | — | — | — | — | — |
| 12 | *V. parahaemolyticus* | AQ 3326 | 2 | — | ○ | — | — | — | — |
| 13 | *V. parahaemolyticus* | AQ 3334 | — | — | — | — | — | — | — |
| 14 | *V. parahaemolyticus* | AQ 3336 | — | — | — | — | — | — | — |
| 15 | *V. parahaemolyticus* | AQ 3362 | 1 | + | ○ | ○ | ○ | ○ | ○ |
| 16 | *V. parahaemolyticus* | AQ 3367 | — | — | — | — | — | — | — |
| 17 | *V. parahaemolyticus* | AQ 3372 | 2 | — | ○ | — | — | — | — |
| 18 | *V. parahaemolyticus* | AQ 3392 | 2 | — | ○ | — | — | — | — |
| 19 | *V. parahaemolyticus* | AQ 3415 | — | + | — | ○ | ○ | ○ | — |

TABLE 1-continued

| No. | Strain | Strain No. | trh | tdh | (a) + (b) | (c) + (d) | (e) + (d) | (e) + (f) | (g) + (h) |
|---|---|---|---|---|---|---|---|---|---|
| 20 | V. parahaemolyticus | AQ 3421 | — | — | — | — | — | — | — |
| 21 | V. parahaemolyticus | AQ 3454 | 1 | — | O | — | — | — | O |
| 22 | V. parahaemolyticus | AQ 3458 | — | — | — | — | — | — | — |
| 23 | V. parahaemolyticus | AQ 3465 | 1 | + | O | O | O | O | O |
| 24 | V. parahaemolyticus | AQ 3491 | 2 | — | O | — | — | — | — |

TABLE 2

| No. | Strain | Strain No. | trh | tdh | (a) + (b) | (c) + (d) | (e) + (d) | (e) + (f) | (g) + (h) |
|---|---|---|---|---|---|---|---|---|---|
| 25 | V. parahaemolyticus | AQ 3516 | 2 | — | O | — | — | — | O |
| 26 | V. parahaemolyticus | AQ 3548 | 2 | — | O | — | — | — | — |
| 27 | V. parahaemolyticus | AQ 3550 | — | — | — | — | — | — | — |
| 28 | V. parahaemolyticus | AQ 3554 | — | — | — | — | — | — | — |
| 29 | V. parahaemolyticus | AQ 3557 | — | — | — | — | — | — | — |
| 30 | V. parahaemolyticus | AQ 3559 | 2 | — | O | — | — | — | — |
| 31 | V. parahaemolyticus | AQ 3562 | 2 | — | O | — | — | — | — |
| 32 | V. parahaemolyticus | AQ 3564 | 2 | — | O | — | — | — | — |
| 33 | V. parahaemolyticus | AQ 3565 | — | — | — | — | — | — | — |
| 34 | V. parahaemolyticus | AQ 3567 | 2 | — | O | — | — | — | — |
| 35 | V. parahaemolyticus | AQ 3588 | — | — | — | — | — | — | — |
| 36 | V. parahaemolyticus | AQ 3592 | 2 | — | O | — | — | — | — |
| 37 | V. parahaemolyticus | AQ 3594 | 2 | — | O | — | — | — | — |
| 38 | V. parahaemolyticus | AQ 3605 | — | — | — | — | — | — | — |
| 39 | V. parahaemolyticus | AQ 3626 | 2 | — | O | — | — | — | — |
| 40 | V. parahaemolyticus | AQ 3631 | 1 | + | O | O | O | O | O |
| 41 | V. parahaemolyticus | AQ 3635 | 1 | + | O | O | O | O | O |
| 42 | V. parahaemolyticus | AQ 3644 | 2 | — | O | — | — | — | — |
| 43 | V. parahaemolyticus | AQ 3655 | 1 | — | O | — | — | — | O |
| 44 | V. parahaemolyticus | AQ 3665 | 2 | — | O | — | — | — | — |
| 45 | V. parahaemolyticus | AQ 3689 | 2 | — | O | — | — | — | O |
| 46 | V. parahaemolyticus | AQ 3694 | 1 | + | O | O | O | O | O |
| 47 | V. parahaemolyticus | AQ 3704 | 2 | — | O | — | — | — | — |
| 48 | V. parahaemolyticus | AQ 3710 | — | — | — | — | — | — | — |

TABLE 3

| No. | Strain | Strain No. | trh | tdh | (a) + (b) | (c) + (d) | (e) + (d) | (e) + (f) | (g) + (h) |
|---|---|---|---|---|---|---|---|---|---|
| 49 | V. parahaemolyticus | AQ 3713 | 1 | — | O | — | — | — | O |
| 50 | V. parahaemolyticus | AQ 3727 | 2 | — | O | — | — | — | — |
| 51 | V. parahaemolyticus | AQ 3732 | 1 | — | O | — | — | — | O |
| 52 | V. parahaemolyticus | AQ 3739 | 1 | + | O | O | O | O | O |
| 53 | V. parahaemolyticus | AQ 3740 | — | + | — | O | O | O | — |
| 54 | V. parahaemolyticus | AQ 3741 | — | + | — | O | O | O | — |
| 55 | V. parahaemolyticus | AQ 3744 | 1 | + | O | O | O | O | O |
| 56 | V. parahaemolyticus | AQ 3754 | 2 | — | O | — | — | — | — |
| 57 | V. parahaemolyticus | AQ 3756 | — | — | — | — | — | — | — |
| 58 | V. parahaemolyticus | AQ 3765 | 1 | + | O | O | O | O | O |
| 59 | V. parahaemolyticus | AQ 3766 | 1 | + | O | O | O | O | O |
| 60 | V. parahaemolyticus | AQ 3776 | 1 | + | O | O | O | O | O |
| 61 | V. parahaemolyticus | AQ 3777 | 2 | — | O | — | — | — | — |
| 62 | V. parahaemolyticus | AQ 3785 | 2 | — | O | — | — | — | — |
| 63 | V. parahaemolyticus | AQ 3789 | 2 | — | O | — | — | — | — |
| 64 | V. parahaemolyticus | AQ 3794 | 1 | — | O | — | — | — | O |
| 65 | V. parahaemolyticus | AQ 3795 | 1 | — | O | — | — | — | O |
| 66 | V. parahaemolyticus | AQ 3801 | 1 | + | O | O | O | O | O |
| 67 | V. parahaemolyticus | AQ 3837 | 2 | — | O | — | — | — | — |
| 68 | V. parahaemolyticus | AQ 3838 | 2 | — | O | — | — | — | — |
| 69 | V. parahaemolyticus | AQ 3840 | 2 | — | O | — | — | — | — |
| 70 | V. parahaemolyticus | AQ 3853 | 1 | + | O | O | O | O | O |
| 71 | V. parahaemolyticus | AQ 3860 | 1 | + | O | O | O | O | O |
| 72 | V. parahaemolyticus | AQ 3869 | — | — | — | — | — | — | — |
| 73 | V. parahaemolyticus | AQ 3880 | 2 | — | O | — | — | — | — |
| 74 | V. parahaemolyticus | AQ 3881 | 2 | — | O | — | — | — | — |

TABLE 4

| No. | Strain | Strain No. | trh | tdh | (a) + (b) | (c) + (d) | (e) + (d) | (e) + (f) | (g) + (h) |
|---|---|---|---|---|---|---|---|---|---|
| 75 | V. parahaemolyticus | AQ 3892 | — | — | — | — | — | — | — |
| 76 | V. parahaemolyticus | AQ 3897 | 1 | + | O | O | O | O | O |
| 77 | V. parahaemolyticus | AQ 3907 | — | — | — | — | — | — | — |
| 78 | V. parahaemolyticus | AQ 3910 | — | — | — | — | — | — | — |
| 79 | V. parahaemolyticus | AQ 3911 | 2 | — | O | — | — | — | — |
| 80 | V. parahaemolyticus | AQ 3915 | 2 | + | O | O | O | O | — |
| 81 | V. parahaemolyticus | AQ 3916 | 2 | — | O | — | — | — | — |
| 82 | V. parahaemolyticus | AQ 3919 | N.A. | — | O | — | — | — | — |
| 83 | V. parahaemolyticus | AQ 3924 | 1 | + | O | O | O | O | O |
| 84 | V. parahaemolyticus | AQ 3933 | — | — | — | — | — | — | — |
| 85 | V. parahaemolyticus | AQ 3945 | 1 | — | O | — | — | — | O |
| 86 | V. parahaemolyticus | AQ 3948 | — | + | — | O | O | O | — |
| 87 | V. parahaemolyticus | AQ 3951 | 1 | — | O | — | — | — | O |
| 88 | V. parahaemolyticus | AQ 3953 | — | — | — | — | — | — | — |
| 89 | V. parahaemolyticus | AQ 3966 | 1 | + | O | O | O | O | O |
| 90 | V. parahaemolyticus | AQ 3969 | 2 | — | O | — | — | — | — |
| 91 | V. parahaemolyticus | AQ 3980 | 2 | — | O | — | — | — | — |
| 92 | V. parahaemolyticus | AQ 3986 | — | + | — | O | O | O | — |
| 93 | V. parahaemolyticus | AQ 3531 | — | + | — | O | O | O | — |
| 94 | V. parahaemolyticus | AQ 3541 | — | + | — | O | O | O | — |
| 95 | V. parahaemolyticus | AQ 3551 | — | + | — | O | O | O | — |
| 96 | V. parahaemolyticus | AQ 3561 | — | + | — | O | O | O | — |
| 97 | V. parahaemolyticus | AQ 3571 | — | + | — | O | O | O | — |
| 98 | V. parahaemolyticus | AQ 3582 | — | + | — | O | O | O | — |
| 99 | V. parahaemolyticus | AQ 3591 | 1 | — | O | — | — | — | O |

TABLE 5

| No. | Strain | Strain No. | trh | tdh | (a) + (b) | (c) + (d) | (e) + (d) | (e) + (f) | (g) + (h) |
|---|---|---|---|---|---|---|---|---|---|
| 100 | V. parahaemolyticus | AQ 3600 | — | + | — | O | O | O | — |
| 101 | V. parahaemolyticus | AQ 3610 | — | + | — | O | O | O | — |
| 102 | V. parahaemolyticus | AQ 3620 | — | + | — | O | O | O | — |
| 103 | V. parahaemolyticus | AQ 3630 | — | + | — | O | O | O | — |
| 104 | V. parahaemolyticus | AQ 3640 | — | + | — | O | O | O | — |
| 105 | V. parahaemolyticus | AQ 3660 | — | + | — | O | O | O | — |
| 106 | V. parahaemolyticus | AQ 3670 | — | + | — | O | O | O | — |
| 107 | V. parahaemolyticus | AQ 3680 | — | + | — | O | O | O | — |
| 108 | V. parahaemolyticus | AQ 3690 | — | + | — | O | O | O | — |
| 109 | V. parahaemolyticus | AQ 3700 | — | + | — | O | O | O | — |
| 110 | V. parahaemolyticus | AQ 3711 | — | + | — | O | O | O | — |
| 111 | V. parahaemolyticus | AQ 3720 | — | + | — | O | O | O | — |
| 112 | V. parahaemolyticus | AQ 3730 | — | + | — | O | O | O | — |
| 113 | V. parahaemolyticus | AQ 3750 | — | + | — | O | O | O | — |
| 114 | V. parahaemolyticus | AQ 3760 | — | + | — | O | O | O | — |
| 115 | V. parahaemolyticus | AQ 3770 | — | + | — | O | O | O | — |
| 116 | V. parahaemolyticus | AQ 3780 | — | + | — | O | O | O | — |
| 117 | V. parahaemolyticus | AQ 3790 | — | + | — | O | O | O | — |
| 118 | V. parahaemolyticus | AQ 3800 | — | + | — | O | O | O | — |
| 119 | V. parahaemolyticus | AQ 3820 | — | + | — | O | O | O | — |
| 120 | V. parahaemolyticus | AQ 3820 | — | + | — | O | O | O | — |
| 121 | V. parahaemolyticus | AQ 3830 | — | + | — | O | O | O | — |
| 122 | V. parahaemolyticus | AQ 3841 | — | + | — | O | O | O | — |
| 123 | V. parahaemolyticus | AQ 3890 | — | + | — | O | O | O | — |
| 124 | V. parahaemolyticus | AQ 3920 | — | + | — | O | O | O | — |
| 125 | V. parahaemolyticus | AQ 3930 | — | + | — | O | O | O | — |

TABLE 6

| No. | Strain | Strain No. | trh | tdh | (a) + (b) | (c) + (d) | (e) + (d) | (e) + (f) | (g) + (h) |
|---|---|---|---|---|---|---|---|---|---|
| 126 | V. parahaemolyticus | AQ 3940 | — | — | — | — | — | — | — |
| 127 | V. parahaemolyticus | AQ 3950 | — | + | — | O | O | O | — |
| 128 | V. parahaemolyticus | AQ 3960 | 1 | — | O | — | — | — | O |
| 129 | V. parahaemolyticus | AQ 3970 | — | + | — | O | O | O | — |
| 130 | V. parahaemolyticus | AQ 3981 | — | + | — | O | O | O | — |
| 131 | V. parahaemolyticus | AQ 3990 | — | + | — | O | O | O | — |
| 132 | V. parahaemolyticus | AQ 4000 | — | + | — | O | O | O | — |

TABLE 6-continued

|  |  |  |  |  | Primer combination | | | | |
| --- | --- | --- | --- | --- | --- | --- | --- | --- | --- |
| No. | Strain | Strain No. | trh | tdh | (a) + (b) | (c) + (d) | (e) + (d) | (e) + (f) | (g) + (h) |
| 133 | V. parahaemolyticus | AQ 4010 | — | + | — | O | O | O | — |
| 134 | V. parahaemolyticus | AQ 4030 | — | + | — | O | O | O | — |
| 135 | V. parahaemolyticus | AQ 4040 | — | + | — | O | O | O | — |
| 136 | V. parahaemolyticus | AQ 4050 | 2 | + | O | O | O | O | — |
| 137 | V. parahaemolyticus | AQ 4060 | — | + | — | O | O | O | — |
| 138 | V. parahaemolyticus | AQ 3128 | — | + | — | O | O | O | — |
| 139 | V. parahaemolyticus | AQ 3138 | — | + | — | O | O | O | — |
| 140 | V. parahaemolyticus | AQ 3158 | — | + | — | O | O | O | — |
| 141 | V. parahaemolyticus | AQ 3161 | — | + | — | O | O | O | — |
| 142 | V. parahaemolyticus | AQ 3171 | — | + | — | O | O | O | — |
| 143 | V. parahaemolyticus | AQ 3181 | 1 | + | O | O | O | O | O |
| 144 | V. parahaemolyticus | AQ 3202 | — | + | — | O | O | O | — |
| 145 | V. parahaemolyticus | AQ 3208 | — | + | — | O | O | O | — |
| 146 | V. parahaemolyticus | AQ 3211 | 1 | + | O | O | O | O | O |
| 147 | V. parahaemolyticus | AQ 3221 | — | + | — | O | O | O | — |
| 148 | V. parahaemolyticus | AQ 3231 | — | + | — | O | O | O | — |
| 149 | V. parahaemolyticus | AQ 3240 | — | + | — | O | O | O | — |
| 150 | V. parahaemolyticus | AQ 3241 | — | + | — | O | O | O | — |

TABLE 7

|  |  |  |  |  | Primer combination | | | | |
| --- | --- | --- | --- | --- | --- | --- | --- | --- | --- |
| No. | Strain | Strain No. | trh | tdh | (a) + (b) | (c) + (d) | (e) + (d) | (e) + (f) | (g) + (h) |
| 151 | V. parahaemolyticus | AQ 3242 | — | + | — | O | O | O | — |
| 152 | V. parahaemolyticus | AQ 3251 | — | + | — | O | O | O | — |
| 153 | V. parahaemolyticus | AQ 3261 | — | + | — | O | O | O | — |
| 154 | V. parahaemolyticus | AQ 3269 | — | + | — | O | O | O | — |
| 155 | V. parahaemolyticus | AQ 3270 | — | + | — | O | O | O | — |
| 156 | V. parahaemolyticus | AQ 3271 | — | + | — | O | O | O | — |
| 157 | V. parahaemolyticus | AQ 3274 | 1 | + | O | O | O | O | O |
| 158 | V. parahaemolyticus | AQ 3281 | — | + | — | O | O | O | — |
| 159 | V. parahaemolyticus | AQ 3294 | — | + | — | O | O | O | — |
| 160 | V. parahaemolyticus | AQ 3304 | — | + | — | O | O | O | — |
| 161 | V. parahaemolyticus | AQ 3306 | — | + | — | O | O | O | — |
| 162 | V. parahaemolyticus | AQ 3307 | — | + | — | O | O | O | — |
| 163 | V. parahaemolyticus | AQ 3308 | — | + | — | O | O | O | — |
| 164 | V. parahaemolyticus | AQ 3312 | — | + | — | O | O | O | — |
| 165 | V. parahaemolyticus | AQ 3314 | — | + | — | O | O | O | — |
| 166 | V. parahaemolyticus | AQ 3324 | — | + | — | O | O | O | — |
| 167 | V. parahaemolyticus | AQ 3335 | — | + | — | O | O | O | — |
| 168 | V. parahaemolyticus | AQ 3345 | — | + | — | O | O | O | — |
| 169 | V. parahaemolyticus | AQ 3365 | — | + | — | O | O | O | — |
| 170 | V. parahaemolyticus | AQ 3382 | — | + | — | O | O | O | — |
| 171 | V. parahaemolyticus | AQ 3385 | — | + | — | O | O | O | — |
| 172 | V. parahaemolyticus | AQ 3395 | — | + | — | O | O | O | — |
| 173 | V. parahaemolyticus | AQ 3405 | — | + | — | O | O | O | — |
| 174 | V. parahaemolyticus | AQ 3426 | — | + | — | O | O | O | — |
| 175 | V. parahaemolyticus | AQ 3436 | — | + | — | O | O | O | — |

TABLE 8

|  |  |  |  |  | Primer combination | | | | |
| --- | --- | --- | --- | --- | --- | --- | --- | --- | --- |
| No. | Strain | Strain No. | trh | tdh | (a) + (b) | (c) + (d) | (e) + (d) | (e) + (f) | (g) + (h) |
| 176 | V. parahaemolyticus | AQ 3446 | — | + | — | O | O | O | — |
| 177 | V. parahaemolyticus | AQ 3451 | — | + | — | O | O | O | — |
| 178 | V. parahaemolyticus | AQ 3471 | — | + | — | O | O | O | — |
| 179 | V. parahaemolyticus | AQ 3492 | — | + | — | O | O | O | — |
| 180 | V. parahaemolyticus | AQ 3501 | — | + | — | O | O | O | — |
| 181 | V. parahaemolyticus | AQ 3511 | — | + | — | O | O | O | — |
| 182 | V. parahaemolyticus | AQ 3521 | — | + | — | O | O | O | — |
| 183 | V. parahaemolyticus | AQ 4070 | — | + | — | O | O | O | — |
| 184 | V. parahaemolyticus | AQ 4080 | — | + | — | O | O | O | — |
| 185 | V. parahaemolyticus | AQ 4090 | — | + | — | O | O | O | — |
| 186 | V. parahaemolyticus | AQ 4093 | 1 | — | O | — | — | — | O |
| 187 | V. parahaemolyticus | AQ 4095 | 1 | — | O | — | — | — | O |
| 188 | V. parahaemolyticus | AQ 4129 | 1 | — | O | — | — | — | O |
| 189 | V. parahaemolyticus | AQ 4100 | — | + | — | O | O | O | — |
| 190 | V. parahaemolyticus | AQ 4110 | — | + | — | O | O | O | — |

TABLE 8-continued

| No. | Strain | Strain No. | trh | tdh | Primer combination | | | | |
|---|---|---|---|---|---|---|---|---|---|
| | | | | | (a) + (b) | (c) + (d) | (e) + (d) | (e) + (f) | (g) + (h) |
| 191 | V. parahaemolyticus | AQ 4120 | — | + | — | ○ | ○ | ○ | — |
| 192 | V. parahaemolyticus | AQ 4130 | — | + | — | ○ | ○ | ○ | — |
| 193 | V. parahaemolyticus | AQ 4133 | 1 | — | ○ | — | — | — | ○ |
| 194 | V. parahaemolyticus | AQ 4150 | — | + | — | ○ | ○ | ○ | — |
| 195 | V. parahaemolyticus | AQ 4160 | — | + | — | ○ | ○ | ○ | — |
| 196 | V. parahaemolyticus | AQ 4170 | — | + | — | ○ | ○ | ○ | — |
| 197 | V. metschnikovii | ATCC 7708 | NT | — | — | — | — | — | — |
| 198 | V. cholerae O1 | PB 1 | — | — | — | — | — | — | — |
| 199 | V. cholerae O1 | SGN 7277 | — | — | — | — | — | — | — |
| 200 | V. cholerae O1 | 1094-79 | — | — | — | — | — | — | — |
| 201 | V. cholerae O1 | E 9120 | — | — | — | — | — | — | — |

TABLE 9

| No. | Strain | Strain No. | trh | tdh | Primer combination | | | | |
|---|---|---|---|---|---|---|---|---|---|
| | | | | | (a) + (b) | (c) + (d) | (e) + (d) | (e) + (f) | (g) + (h) |
| 202 | V. cholerae O1 | E 506 | — | — | — | — | — | — | — |
| 203 | V. cholerae O1 | PB 17 | — | — | — | — | — | — | — |
| 204 | V. furnissil | ATCC 35016 | — | — | — | — | — | — | — |
| 205 | V. mimicus | ATCC 33653 | — | — | — | — | — | — | — |
| 206 | V. mimicus | Lab No. 1 | — | — | — | ○ | ○ | ○ | — |
| 207 | V. mimicus | Lab No. 14 | — | — | — | — | — | — | — |
| 208 | V. parahaemolyticus | AQ 4033 | 1 | + | ○ | ○ | ○ | ○ | ○ |
| 209 | V. parahaemolyticus | AQ 4037 | 1 | — | ○ | — | — | — | ○ |
| 210 | Aeromonas | Lab No. 74 | — | — | — | — | — | — | — |
| 211 | V. cholerae non O1 | Lab No. 90 | — | — | — | — | — | — | — |
| 212 | V. cholerae non O1 | Lab No. 91 | — | + | — | ○ | ○ | ○ | — |
| 213 | V. cholerae non O1 | Lab No. 7 | — | — | — | — | — | — | — |
| 214 | V. cholerae non O1 | AQ 1254 | — | — | — | — | — | — | — |
| 215 | V. cholerae non O1 | AQ 1255 | — | — | — | — | — | — | — |
| 216 | V. cholerae non O1 | AQ 1257 | — | — | — | — | — | — | — |
| 217 | V. cholerae non O1 | AQ 1259 | — | — | — | — | — | — | — |
| 218 | V. cholerae non O1 | AQ 1261 | — | — | — | — | — | — | — |
| 219 | V. cholerae non O1 | AQ 1262 | — | — | — | — | — | — | — |
| 220 | V. cholerae non O1 | AQ 1266 | — | — | — | — | — | — | — |
| 221 | V. cholerae non O1 | AQ 1268 | — | — | — | — | — | — | — |
| 222 | V. cholerae non O1 | AQ 1271 | — | — | — | — | — | — | — |
| 223 | V. cholerae non O1 | AQ 1272 | — | — | — | — | — | — | — |
| 224 | V. cholerae non O1 | AQ 1273 | — | — | — | — | — | — | — |
| 225 | V. cholerae non O1 | AQ 1276 | — | — | — | — | — | — | — |
| 226 | V. cholerae non O1 | AQ 1278 | — | — | — | — | — | — | — |
| 227 | V. cholerae non O1 | AQ 1280 | — | — | — | — | — | — | — |

TABLE 10

| No. | Strain | Strain No. | trh | tdh | Primer combination | | | | |
|---|---|---|---|---|---|---|---|---|---|
| | | | | | (a) + (b) | (c) + (d) | (e) + (d) | (e) + (f) | (g) + (h) |
| 228 | V. cholerae non O1 | AQ 1283 | — | — | — | — | — | — | — |
| 229 | V. cholerae non O1 | AQ 1286 | — | — | — | — | — | — | — |
| 230 | V. cholerae non O1 | AQ 1289 | — | — | — | — | — | — | — |
| 231 | V. cholerae non O1 | AQ 1290 | — | — | — | — | — | — | — |
| 232 | V. cholerae non O1 | AQ 1292 | — | — | — | — | — | — | — |
| 233 | V. cholerae non O1 | AQ 1294 | — | — | — | — | — | — | — |
| 234 | V. cholerae non O1 | AQ 1297 | — | — | — | — | — | — | — |
| 235 | V. cholerae non O1 | AQ 1299 | — | — | — | — | — | — | — |
| 236 | V. cholerae non O1 | AQ 1300 | — | — | — | — | — | — | — |
| 237 | V. cholerae non O1 | AQ 1304 | — | — | — | — | — | — | — |
| 238 | V. cholerae non O1 | AQ 1305 | — | — | — | — | — | — | — |
| 239 | V. cholerae non O1 | AQ 1306 | — | — | — | — | — | — | — |
| 240 | V. cholerae non O1 | AQ 1308 | — | — | — | — | — | — | — |
| 241 | V. cholerae non O1 | AQ 1312 | — | — | — | — | — | — | — |
| 242 | V. cholerae non O1 | AQ 1314 | — | — | — | — | — | — | — |
| 243 | V. cholerae non O1 | AQ 1315 | — | — | — | — | — | — | — |
| 244 | V. cholerae non O1 | AQ 1316 | — | — | — | — | — | — | — |
| 245 | V. cholerae non O1 | AQ 1317 | — | — | — | — | — | — | — |
| 246 | V. cholerae non O1 | AQ 1321 | — | — | — | — | — | — | — |
| 247 | V. cholerae non O1 | AQ 1322 | — | — | — | — | — | — | — |
| 248 | V. cholerae non O1 | AQ 1325 | — | — | — | — | — | — | — |

TABLE 10-continued

|  |  |  |  |  | Primer combination | | | | |
| --- | --- | --- | --- | --- | --- | --- | --- | --- | --- |
| No. | Strain | Strain No. | trh | tdh | (a) + (b) | (c) + (d) | (e) + (d) | (e) + (f) | (g) + (h) |
| 249 | V. cholerae non O1 | KB 274 | — | — | — | — | — | — | — |
| 250 | V. cholerae non O1 | KB 289 | — | — | — | — | — | — | — |
| 251 | V. cholerae non O1 | KB 297 | — | — | — | — | — | — | — |
| 252 | V. cholerae non O1 | KB 305 | — | — | — | — | — | — | — |

TABLE 11

|  |  |  |  |  | Primer combination | | | | |
| --- | --- | --- | --- | --- | --- | --- | --- | --- | --- |
| No. | Strain | Strain No. | trh | tdh | (a) + (b) | (c) + (d) | (e) + (d) | (e) + (f) | (g) + (h) |
| 253 | V. cholerae non O1 | 59H-63 | — | — | — | — | — | — | — |
| 254 | V. cholerae non O1 | 59H-168 | — | — | — | — | — | — | — |
| 255 | V. cholerae non O1 | 60H-113 | — | — | — | — | — | — | — |
| 256 | V. fluvialis | 59H-165 | — | — | — | — | — | — | — |
| 257 | V. fluvialis | 61H-79 | — | — | — | — | — | — | — |
| 258 | V. fluvialis | 61H-175 | — | — | — | — | — | — | — |
| 259 | V. furnissil | 61H-176 | — | — | — | — | — | — | — |
| 260 | V. fluvialis | 61H-178 | — | — | — | — | — | — | — |
| 261 | V. furnissil | 61H-180 | — | — | — | — | — | — | — |
| 262 | V. furnissil | 61H-212 | — | — | — | — | — | — | — |
| 263 | V. mimicus | 60H-39 | — | + | — | ○ | ○ | ○ | — |
| 264 | V. cholerae O1 | 61H-110 | — | — | — | — | — | — | — |
| 265 | V. cholerae O1 | 61H-151 | — | — | — | — | — | — | — |
| 266 | V. cholerae O1 | 56H-118 | — | — | — | — | — | — | — |
| 267 | V. cholerae O1 | 56H-119 | — | — | — | — | — | — | — |
| 268 | V. fluvialis | 58H-128 | — | — | — | — | — | — | — |
| 269 | V. cholerae non O1 | 1 | — | — | — | — | — | — | — |
| 270 | V. cholerae non O1 | 7 | — | — | — | — | — | — | — |
| 271 | V. cholerae non O1 | 8 | — | — | — | — | — | — | — |
| 272 | V. cholerae non O1 | 12 | — | — | — | — | — | — | — |
| 273 | V. cholerae non O1 | 17 | — | — | — | — | — | — | — |
| 274 | V. cholerae non O1 | 21 | — | — | — | — | — | — | — |
| 275 | V. cholerae non O1 | 37 | — | — | — | — | — | — | — |
| 276 | V. cholerae non O1 | 41 | — | — | — | — | — | — | — |
| 277 | V. cholerae non O1 | 62 | — | — | — | — | — | — | — |

TABLE 12

|  |  |  |  |  | Primer combination | | | | |
| --- | --- | --- | --- | --- | --- | --- | --- | --- | --- |
| No. | Strain | Strain No. | trh | tdh | (a) + (b) | (c) + (d) | (e) + (d) | (e) + (f) | (g) + (h) |
| 278 | V. cholerae non O1 | 70 | — | — | — | — | — | — | — |
| 279 | V. cholerae non O1 | 75 | — | — | — | — | — | — | — |
| 280 | V. cholerae non O1 | 102 | — | — | — | — | — | — | — |
| 281 | V. cholerae non O1 | 106 | — | — | — | — | — | — | — |
| 282 | V. cholerae non O1 | 107 | — | — | — | — | — | — | — |
| 283 | V. cholerae non O1 | 109 | — | — | — | — | — | — | — |
| 284 | V. cholerae non O1 | 111 | — | — | — | — | — | — | — |
| 285 | V. cholerae non O1 | 126 | — | — | — | — | — | — | — |
| 286 | V. cholerae non O1 | 128 | — | — | — | — | — | — | — |
| 287 | V. cholerae non O1 | 129 | — | — | — | — | — | — | — |
| 288 | V. cholerae non O1 | 131 | — | — | — | — | — | — | — |
| 289 | V. cholerae non O1 | 133 | — | — | — | — | — | — | — |
| 290 | V. cholerae non O1 | 138 | — | — | — | — | — | — | ● |
| 291 | V. cholerae non O1 | 139 | — | — | — | — | — | — | — |
| 292 | V. cholerae non O1 | 142 | — | — | — | — | — | — | — |
| 293 | V. cholerae non O1 | 147 | — | — | — | — | — | — | — |
| 294 | V. cholerae non O1 | 150 | — | — | — | — | — | — | — |
| 295 | V. cholerae non O1 | 151 | — | — | — | — | — | — | — |
| 296 | V. cholerae non O1 | 157 | — | — | — | — | — | — | — |
| 297 | V. cholerae non O1 | 184 | — | — | — | — | — | — | — |
| 298 | V. parahaemolyticus | BG-50 | — | — | — | — | — | — | — |
| 299 | V. parahaemolyticus | BG-51 | — | — | — | — | — | — | — |
| 300 | V. parahaemolyticus | BG-52 | — | — | — | — | — | — | — |
| 301 | V. parahaemolyticus | BG-53 | — | — | — | — | — | — | — |
| 302 | V. parahaemolyticus | BG-56 | — | — | — | — | — | — | — |
| 303 | V. parahaemolyticus | BG-57 | — | — | — | — | — | — | — |

TABLE 13

| No. | Strain | Strain No. | trh | tdh | Primer combination | | | | |
|-----|--------|------------|-----|-----|-------|-------|-------|-------|-------|
| | | | | | (a) + (b) | (c) + (d) | (e) + (d) | (e) + (f) | (g) + (h) |
| 304 | V. parahaemolyticus | BG-58 | — | — | — | — | — | — | — |
| 305 | V. parahaemolyticus | BG-59 | — | — | — | — | — | — | — |
| 306 | V. parahaemolyticus | BG-62 | — | — | — | — | — | — | — |
| 307 | V. parahaemolyticus | BG-64 | 2 | — | ○ | — | — | — | — |
| 308 | V. parahaemolyticus | BG-94 | 2 | — | ○ | — | — | ● | — |
| 309 | V. parahaemolyticus | BG-95 | — | — | — | — | — | — | — |
| 310 | V. parahaemolyticus | BG-121 | — | — | — | — | — | — | — |
| 311 | V. parahaemolyticus | BG-124 | — | — | — | — | — | — | — |
| 312 | V. parahaemolyticus | BG-126 | — | — | — | — | — | — | — |
| 313 | V. parahaemolyticus | BG-127 | — | — | — | — | — | — | — |
| 314 | V. parahaemolyticus | BG-128 | — | — | — | — | — | — | — |
| 315 | V. parahaemolyticus | BG-129 | — | — | — | — | — | — | — |
| 316 | V. parahaemolyticus | BG-130 | — | — | — | — | — | — | — |
| 317 | V. parahaemolyticus | BG-132 | — | — | — | — | — | — | — |
| 318 | V. parahaemolyticus | BG-133 | — | — | — | — | — | — | — |
| 319 | V. parahaemolyticus | BG-134 | — | — | — | — | — | — | — |
| 320 | V. parahaemolyticus | BG-135 | — | — | — | — | — | — | — |
| 321 | V. parahaemolyticus | BG-137 | — | — | — | — | — | — | — |
| 322 | V. parahaemolyticus | BG-138 | — | — | — | — | — | — | — |
| 323 | V. parahaemolyticus | BG-1 | — | — | — | — | — | — | — |
| 324 | V. parahaemolyticus | BG-2 | — | — | — | — | — | — | — |
| 325 | V. parahaemolyticus | BG-3 | — | — | — | — | — | — | — |
| 326 | V. parahaemolyticus | BG-12 | — | — | — | — | — | — | — |
| 327 | V. parahaemolyticus | BG-13 | — | — | — | — | — | — | — |
| 328 | V. parahaemolyticus | BG-14 | — | — | — | — | — | — | — |

TABLE 14

| No. | Strain | Strain No. | trh | tdh | Primer combination | | | | |
|-----|--------|------------|-----|-----|-------|-------|-------|-------|-------|
| | | | | | (a) + (b) | (c) + (d) | (e) + (d) | (e) + (f) | (g) + (h) |
| 329 | V. parahaemolyticus | BG-22 | — | — | — | — | — | — | — |
| 330 | V. parahaemolyticus | BG-23 | — | — | — | — | — | — | — |
| 331 | V. parahaemolyticus | BG-24 | — | — | — | — | — | — | — |
| 332 | V. parahaemolyticus | BG-25 | — | — | — | — | — | — | — |
| 333 | V. parahaemolyticus | BG-26 | — | — | — | — | — | — | — |
| 334 | V. parahaemolyticus | BG-31 | — | — | — | — | — | — | — |
| 335 | V. parahaemolyticus | BG-33 | — | — | — | — | — | — | — |
| 336 | V. parahaemolyticus | BG-34 | — | — | — | — | — | — | — |
| 337 | V. parahaemolyticus | BG-35 | — | — | — | — | — | — | — |
| 338 | V. parahaemolyticus | A-3-2 | — | — | — | — | — | — | — |
| 339 | V. parahaemolyticus | AP-2 | 2 | — | ○ | — | — | — | — |
| 340 | V. parahaemolyticus | AT-4 | 2 | — | ○ | — | — | — | — |
| 341 | V. parahaemolyticus | AY-3-4 | — | — | — | — | — | ● | — |
| 342 | V. parahaemolyticus | BM-2-3 | — | — | — | — | — | — | — |
| 343 | V. parahaemolyticus | CH-8-3 | — | — | — | — | — | — | — |
| 344 | V. parahaemolyticus | CK-5-5 | — | — | — | — | — | — | — |
| 345 | V. parahaemolyticus | CM-32-3 | — | — | — | — | ● | ● | — |
| 346 | V. parahaemolyticus | CX-6 | — | — | — | — | — | ● | — |
| 347 | V. parahaemolyticus | DW-1-2 | — | — | — | — | — | — | — |
| 348 | V. parahaemolyticus | EW-2-2 | — | — | — | — | — | — | — |
| 349 | V. parahaemolyticus | FD-2-3 | — | — | — | — | — | — | — |
| 350 | V. parahaemolyticus | FE-2-2 | 2 | — | ○ | — | — | ● | — |
| 351 | V. parahaemolyticus | FG-34-4 | — | — | — | — | — | — | — |
| 352 | V. parahaemolyticus | GH-13-3 | — | — | — | — | — | — | — |
| 353 | V. parahaemolyticus | 257 | 1 | + | ○ | ○ | ○ | ○ | ○ |
| 354 | V. parahaemolyticus | 266 | — | + | — | ○ | ○ | ○ | — |

TABLE 15

| No. | Strain | Strain No. | trh | tdh | Primer combination | | | | |
|-----|--------|------------|-----|-----|-------|-------|-------|-------|-------|
| | | | | | (a) + (b) | (c) + (d) | (e) + (d) | (e) + (f) | (g) + (h) |
| 355 | V. parahaemolyticus | 268 | — | + | — | ○ | ○ | ○ | — |
| 356 | V. parahaemolyticus | 269 | — | + | — | ○ | ○ | ○ | — |
| 357 | V. parahaemolyticus | 270 | — | + | — | ○ | ○ | ○ | — |
| 358 | V. parahaemolyticus | 282 | — | + | — | ○ | ○ | ○ | — |
| 359 | V. parahaemolyticus | 283 | — | + | — | ○ | ○ | ○ | — |
| 360 | V. parahaemolyticus | 284 | — | + | — | ○ | ○ | ○ | — |
| 361 | V. parahaemolyticus | 285 | — | + | — | ○ | ○ | ○ | — |

TABLE 15-continued

| No. | Strain | Strain No. | trh | tdh | Primer combination | | | | |
|---|---|---|---|---|---|---|---|---|---|
| | | | | | (a) + (b) | (c) + (d) | (e) + (d) | (e) + (f) | (g) + (h) |
| 362 | V. parahaemolyticus | 286 | — | + | — | O | O | O | — |

TABLE 16

| No. | Strain | Strain No. | Primer combination | | | | |
|---|---|---|---|---|---|---|---|
| | | | (a) + (b) | (c) + (d) | (e) + (d) | (e) + (f) | (g) + (h) |
| 1 | Bacillus cereus | ATCC 14579 | — | — | — | — | — |
| 2 | Bacillus subtilis | JCM 1465 | — | — | — | — | — |
| 3 | Staphylococcus auveus | JCM 2413 | — | — | — | — | — |
| 4 | Staphylococcus epidermidis | JCM 2414 | — | — | — | — | — |
| 5 | Salmonella typhimurium | IFO 12529 | — | — | — | — | — |
| 6 | Salmonella enteritidis | IFO 3163 | — | — | — | — | — |
| 7 | Clostridium perfringens | ATCC 12917 | — | — | — | — | — |
| 8 | Vibrio cholerae | ATCC 25872 | — | — | — | — | — |
| 9 | Vibrio cholerae type Ogawa | ATCC 9458 | — | — | — | — | — |
| 10 | Vibrio cholerae type Inaba | ATCC 9459 | — | — | — | — | — |
| 11 | Vibrio fluvialis | JCM 3752 | — | — | — | — | — |
| 12 | Campylobacter jejuni | JCM 2013 | — | — | — | — | — |
| 13 | Campylobacter coli | JCM 2529 | — | — | — | — | — |
| 14 | E. coli | JCM 1649 | — | — | — | — | — |
| 15 | Yersinia enterocolitica | ATCC 9610 | — | — | — | — | — |
| 16 | Sigella dysenteriae | ATCC 9361 | — | — | — | — | — |
| 17 | Sigella flexneri | ATCC 29903 | — | — | — | — | — |
| 18 | Sigella sonnei | ATCC 29930 | — | — | — | — | — |
| 19 | Bacteroides flagilis | ATCC 23745 | — | — | — | — | — |
| 20 | Bacteroides vulgatus | JCM 5826 | — | ● | — | — | — |

TABLE 17

| No. | Strain | Strain No. | Primer combination | | | | |
|---|---|---|---|---|---|---|---|
| | | | (a) + (b) | (c) + (d) | (e) + (d) | (e) + (f) | (g) + (h) |
| 21 | Enterococcus feacalis | JCM 5803 | — | — | — | — | — |
| 22 | Klebsiella pneumoniae | JCM 1662 | — | — | — | — | — |
| 23 | Proteus vulgaris | JCM 1668 | — | — | — | — | — |
| 24 | Citrobacter freundil | ATCC 33128 | — | — | — | — | — |
| 25 | Streptococcus pyogenes | ATCC 12344 | — | — | — | — | — |
| 26 | Streptococcus pneumoniae | ATCC 33400 | — | — | — | — | — |
| 27 | Haemophilus influenzae | ATCC 33391 | — | — | — | — | ● |
| 28 | Proteus mivabilis | ATCC 29906 | — | — | — | — | — |
| 29 | Neisseria gonorrheae | ATCC 19424 | — | — | — | — | — |
| 30 | Neisseria meningitidis | ATCC 13077 | — | — | — | — | — |
| 31 | Listeria monocygenes | ATCC 15313 | — | — | — | — | — |
| 32 | Lactobacillus acidophillus | JCM 1132 | — | — | — | — | — |
| 33 | Bifidobacterium adolescentis | JCM 1275 | — | — | — | — | — |
| 34 | Fusobacterium nucleatum | ATCC 25586 | — | — | — | — | — |
| 35 | Propiobacterium acnes | ATCC 6919 | — | — | — | — | — |
| 36 | Veillonella alypica | ATCC 17744 | — | — | — | — | — |
| 37 | Pseudomonas aeruginosa | IFO 12689 | — | — | — | — | — |
| 38 | Corinebacterium diphtheriae | JCM 1310 | — | — | — | — | — |
| 39 | Peptostreptococcus anaerobius | ATCC 27337 | — | — | — | — | — |
| 40 | Human placental DNA | | — | ● | — | — | — |

TABLE 18

| No. | Strain | (Strain No.) | LT gene | Primer | | |
|---|---|---|---|---|---|---|
| | | | | (a) + (b) | (c) + (d) | (e) + (d) |
| 1 | E. coli | WHO1 | — | — | — | — |
| 2 | E. coli | WHO2 | — | — | — | — |
| 3 | E. coli | WHO3 | — | — | — | — |
| 4 | E. coli | WHO4 | — | — | — | — |
| 5 | E. coli | WHO5 | — | — | — | — |
| 6 | E. coli | WHO6 | — | — | — | — |
| 7 | E. coli | WHO7 | — | — | — | — |
| 8 | E. coli | WHO8 | + | + | + | + |
| 9 | E. coli | WHO9 | + | + | + | + |
| 10 | E. coli | WHO10 | + | + | + | + |
| 11 | E. coli | WHO11 | — | — | — | — |
| 12 | E. coli | WHO12 | — | — | — | — |
| 13 | E. coli | WHO13 | — | — | — | — |
| 14 | E. coli | WHO14 | — | — | — | — |

TABLE 18-continued

| No. | (Strain No.) | LT gene | Primer (a) + (b) | (c) + (d) | (e) + (d) |
|---|---|---|---|---|---|
| 15 | E. coli WHO15 | — | — | — | — |
| 16 | E. coli WHO16 | — | — | — | — |
| 17 | E. coli WHO17 | + | + | + | + |
| 18 | E. coli WHO18 | + | + | + | + |
| 19 | E. coli WHO19 | — | — | — | — |
| 20 | E. coli WHO20 | — | — | — | — |
| 21 | E. coli WHO21 | — | — | — | — |
| 22 | E. coli WHO22 | — | — | — | — |
| 23 | E. coli WHO23 | — | — | — | — |
| 24 | E. coli WHO24 | 2+ | + | + | + |
| 25 | E. coli WHO25 | + | + | + | + |
| 26 | E. coli WHO26 | w | + | + | + |
| 27 | E. coli WHO27 | w | + | + | + |
| 28 | E. coli WHO28 | + | + | + | + |
| 29 | E. coli WHO29 | — | — | — | — |
| 30 | E. coli WHO30 | — | — | — | — |
| 31 | E. coli WHO31 | — | — | — | — |
| 32 | E. coli WHO32 | — | — | — | — |
| 33 | E. coli WHO33 | — | — | — | — |
| 34 | E. coli WHO34 | — | — | — | — |
| 35 | E. coli WHO35 | 2+ | + | + | + |
| 36 | E. coli WHO36 | w | + | + | + |
| 37 | E. coli WHO37 | — | — | — | — |
| 38 | E. coli WHO38 | — | — | — | — |
| 39 | E. coli WHO39 | — | — | — | — |
| 40 | E. coli WHO40 | — | — | — | — |

TABLE 19

| No. | (Strain No.) | LT gene | Primer (a) + (b) | (c) + (d) | (e) + (d) |
|---|---|---|---|---|---|
| 41 | E. coli WHO41 | — | — | — | — |
| 42 | E. coli WHO42 | — | — | — | — |
| 43 | E. coli WHO43 | + | + | + | + |
| 44 | E. coli WHO44 | + | + | + | + |
| 45 | E. coli WHO45 | + | + | + | + |
| 46 | E. coli WHO46 | — | — | — | — |
| 47 | E. coli WHO47 | — | — | — | — |
| 48 | E. coli WHO48 | — | — | — | — |
| 49 | E. coli WHO49 | — | — | — | — |
| 50 | E. coli WHO50 | — | — | — | — |
| 51 | E. coli WHO51 | — | — | — | — |
| 52 | E. coli WHO52 | — | — | — | — |
| 53 | E. coli WHO53 | — | — | — | — |
| 54 | E. coli WHO54 | — | — | — | — |
| 55 | E. coli WHO55 | — | — | — | — |
| 56 | E. coli WHO56 | — | — | — | — |
| 57 | E. coli WHO57 | + | + | + | + |
| 58 | E. coli WHO58 | + | + | + | + |
| 59 | E. coli WHO59 | — | — | — | — |
| 60 | E. coli WHO60 | — | — | — | — |
| 61 | E. coli WHO61 | — | — | — | — |
| 62 | E. coli WHO62 | — | — | — | — |
| 63 | E. coli WHO63 | + | + | + | + |
| 64 | E. coli WHO64 | — | — | — | — |
| 65 | E. coli WHO65 | — | — | — | — |
| 66 | E. coli WHO66 | — | — | — | — |
| 67 | E. coli WHO67 | + | + | + | + |
| 68 | E. coli WHO68 | 2+ | + | + | + |
| 69 | E. coli WHO69 | — | — | — | — |
| 70 | E. coli WHO70 | — | — | — | — |
| 71 | E. coli WHO71 | + | + | + | + |
| 72 | E. coli WHO72 | + | + | + | + |
| 73 | E. coli WHO73 | + | + | + | + |
| 74 | E. coli WHO74 | — | — | — | — |
| 75 | E. coli WHO75 | + | + | + | + |
| 76 | E. coli WHO76 | — | — | — | — |
| 77 | E. coli WHO77 | — | — | — | — |
| 78 | E. coli WHO78 | — | — | — | — |
| 79 | E. coli WHO79 | — | — | — | — |
| 80 | E. coli WHO80 | — | — | — | — |

TABLE 20

| No. | (Strain No.) | LT gene | Primer (a) + (b) | (c) + (d) | (e) + (d) |
|---|---|---|---|---|---|
| 81 | E. coli WHO81 | — | — | — | — |
| 82 | E. coli WHO82 | — | — | — | — |
| 83 | E. coli WHO83 | — | — | — | — |
| 84 | E. coli WHO84 | — | — | — | — |
| 85 | E. coli WHO85 | + | + | + | + |
| 86 | E. coli WHO86 | — | — | — | — |
| 87 | E. coli WHO87 | — | — | — | — |
| 88 | E. coli WHO88 | — | — | — | — |
| 89 | E. coli WHO89 | + | + | + | + |
| 90 | E. coli WHO90 | — | — | — | — |
| 91 | E. coli WHO91 | + | + | + | + |
| 92 | E. coli WHO92 | — | — | — | — |
| 93 | E. coli WHO93 | + | + | + | + |
| 94 | E. coli WHO94 | + | + | + | + |
| 95 | E. coli WHO95 | — | — | — | — |
| 96 | E. coli WHO96 | + | + | + | + |
| 97 | E. coli WHO97 | — | — | — | — |
| 98 | E. coli WHO98 | — | — | — | — |
| 99 | E. coli WHO99 | + | + | + | + |
| 100 | E. coli WHO100 | + | + | + | + |
| 101 | E. coli WHO101 | — | — | — | — |
| 102 | E. coli WHO102 | + | + | + | + |
| 103 | E. coli WHO103 | — | — | — | — |
| 104 | E. coli WHO104 | — | — | — | — |
| 105 | E. coli WHO105 | — | — | — | — |
| 106 | E. coli WHO106 | — | — | — | — |
| 107 | E. coli WHO107 | — | — | — | — |
| 108 | E. coli WHO108 | — | — | — | — |
| 109 | E. coli WHO109 | — | — | — | — |
| 110 | E. coli WHO110 | — | — | — | — |
| 111 | E. coli WHO111 | + | + | + | + |
| 112 | E. coli WHO112 | + | + | + | + |
| 113 | E. coli WHO113 | — | — | — | — |
| 114 | E. coli WHO114 | — | — | — | — |
| 115 | E. coli WHO115 | — | — | — | — |
| 116 | E. coli WHO116 | — | — | — | — |
| 117 | E. coli WHO117 | — | — | — | — |
| 118 | E. coli WHO118 | — | — | — | — |
| 119 | E. coli WHO119 | — | — | — | — |
| 120 | E. coli WHO120 | — | — | — | — |

TABLE 21

| No. | (Strain No.) | Lt gene | Primer (a) + (b) | (c) + (d) | (e) + (d) |
|---|---|---|---|---|---|
| 121 | E. coli WHO121 | — | — | — | — |
| 122 | E. coli WHO122 | — | — | — | — |
| 123 | E. coli WHO123 | — | — | — | — |
| 124 | E. coli WHO124 | + | + | + | + |
| 125 | E. coli WHO125 | — | — | — | — |
| 126 | E. coli WHO126 | — | — | — | — |
| 127 | E. coli WHO127 | — | — | — | — |
| 128 | E. coli WHO128 | — | — | — | — |
| 129 | E. coli WHO129 | + | + | + | + |
| 130 | E. coli WHO130 | — | — | — | — |
| 131 | E. coli WHO131 | — | — | — | — |
| 132 | E. coli WHO132 | — | — | — | — |
| 133 | E. coli WHO133 | — | — | — | — |
| 134 | E. coli WHO134 | — | — | — | — |
| 135 | E. coli WHO135 | — | — | — | — |
| 136 | E. coli WHO136 | + | + | + | + |
| 137 | E. coli WHO137 | — | — | — | — |

TABLE 21-continued

| No. | (Strain No.) | Lt gene | Primer (a) + (b) | (c) + (d) | (e) + (d) |
|---|---|---|---|---|---|
| 138 | E. coli WHO138 | + | + | + | + |
| 139 | E. coli WHO139 | — | — | — | — |
| 140 | E. coli WHO140 | — | — | — | — |
| 141 | E. coli WHO141 | — | — | — | — |
| 142 | E. coli WHO142 | + | + | + | + |
| 143 | E. coli WHO143 | — | — | — | — |
| 144 | E. coil WHO144 | — | — | — | — |
| 145 | E. coli WHO145 | + | + | + | + |
| 146 | E. coli WHO146 | — | — | — | — |
| 147 | E. coli WHO147 | — | — | — | — |
| 148 | E. coli WHO148 | + | + | + | + |
| 149 | E. coli WHO149 | — | — | — | — |
| 150 | E. coli WHO150 | — | — | — | — |
| 151 | E. coli WHO151 | — | — | — | — |
| 152 | E. coli WHO152 | — | — | — | — |
| 153 | E. coli WHO153 | + | + | + | + |
| 154 | E. coli WHO154 | + | + | + | + |
| 155 | E. coli WHO155 | — | — | — | — |
| 156 | E. coli WHO156 | — | — | — | — |
| 157 | E. coli WHO157 | — | — | — | — |
| 158 | E. coli WHO158 | + | + | + | + |
| 159 | E. coli WHO159 | — | — | — | — |
| 160 | E. coli WHO160 | — | — | — | — |

TABLE 22

| No. | (Strain No.) | Lt gene | Primer (a) + (b) | (c) + (d) | (e) + (d) |
|---|---|---|---|---|---|
| 161 | E. coli WHO161 | — | — | — | — |
| 162 | E. coli WHO162 | — | — | — | — |
| 163 | E. coli WHO163 | — | — | — | — |
| 164 | E. coli WHO164 | — | — | — | — |
| 165 | E. coli WHO165 | — | — | — | — |
| 166 | E. coli WHO166 | — | — | — | — |
| 167 | E. coli WHO167 | — | — | — | — |
| 168 | E. coli WHO168 | + | + | + | + |
| 169 | E. coli WHO169 | — | — | — | — |
| 170 | E. coli WHO170 | — | — | — | — |
| 171 | E. coli WHO171 | — | — | — | — |
| 172 | E. coli WHO172 | — | — | — | — |
| 173 | E. coli WHO173 | — | — | — | — |
| 174 | E. coli WHO174 | — | — | — | — |
| 175 | E. coli WHO175 | + | + | + | + |
| 176 | E. coli WHO176 | — | — | — | — |
| 177 | E. coli WHO177 | — | — | — | — |
| 178 | E. coli WHO178 | + | + | + | + |
| 179 | E. coli WHO179 | — | — | — | — |
| 180 | E. coli WHO180 | — | — | — | — |
| 181 | E. coli WHO181 | — | — | — | — |
| 182 | E. coli WHO182 | — | — | — | — |
| 183 | E. coli WHO183 | — | — | — | — |
| 184 | E. coil WHO184 | — | — | — | — |
| 185 | E. coli WHO185 | — | — | — | — |
| 186 | E. coli WHO186 | — | — | — | — |
| 187 | E. coli WHO187 | — | — | — | — |
| 188 | E. coli WHO188 | — | — | — | — |
| 189 | E. coli WHO189 | — | — | — | — |
| 190 | E. coli WHO190 | + | + | + | + |
| 191 | E. coli WHO191 | + | + | + | + |
| 192 | E. coli WHO192 | — | — | — | — |
| 193 | E. coli WHO193 | — | — | — | — |
| 194 | E. coli WHO194 | — | — | — | — |
| 195 | E. coli WHO195 | — | — | — | — |
| 196 | E. coli WHO196 | + | + | + | + |
| 197 | E. coli WHO197 | — | — | — | — |
| 198 | E. coli WHO198 | — | — | — | — |
| 199 | E. coli WHO199 | — | — | — | — |
| 200 | E. coli WHO200 | + | + | + | + |

TABLE 23

| No. | (Strain No.) | LT gene | Primer (a) + (b) | (c) + (d) | (e) + (d) |
|---|---|---|---|---|---|
| 201 | E. coli 21-21 | — | — | — | — |
| 202 | E. coli 21-22 | — | — | — | — |
| 203 | E. coli 21-23 | — | — | — | — |
| 204 | E. coli 21-24 | — | — | — | — |
| 205 | E. coli 7-62 | — | — | — | — |
| 206 | E. coli 7-63 | — | — | — | — |
| 207 | E. coli 7-64 | — | — | — | — |
| 208 | E. coli 8-41 | + | + | + | + |
| 209 | E. coli 8-43 | — | — | — | — |
| 210 | E. coli 8-44 | + | + | + | + |
| 211 | E. coli 5-13 | — | — | — | — |
| 212 | E. coli 5-14 | — | — | — | — |
| 213 | E. coli 7-53 | — | — | — | — |
| 214 | E. coli 7-56 | — | — | — | — |
| 215 | E. coli 7-58 | — | — | — | — |
| 216 | E. coli 2-15-161 | — | — | — | — |
| 217 | E. coli 2-15-163 | — | — | — | — |
| 218 | E. coli 28-103 | — | — | — | — |
| 219 | E. coli 28-104 | — | — | — | — |
| 220 | E. coli 19-126 | — | — | — | — |
| 221 | E. coli 9-127 | — | — | — | — |
| 222 | E. coli 29-212 | — | — | — | — |
| 223 | E. coli 29-213 | — | — | — | — |
| 224 | E. coli 29-214 | — | — | — | — |
| 225 | E. coli 9-215 | — | — | — | — |
| 226 | E. coli 14-13 | — | — | — | — |
| 227 | E. coli 14-14 | — | — | — | — |
| 228 | E. coli 5-11 | — | — | — | — |
| 229 | E. coli 5-12 | — | — | — | — |
| 230 | E. coli 13-13 | — | — | — | — |
| 231 | E. coli 13-15 | — | — | — | — |
| 232 | E. coli 13-21 | — | — | — | — |
| 233 | E. coli 13-22 | — | — | — | — |
| 234 | E. coli 13-23 | — | — | — | — |
| 235 | E. coli 13-24 | — | — | — | — |
| 236 | E. coli 14-15 | — | — | — | — |
| 237 | E. coli 14-16 | — | — | — | — |
| 238 | E. coli 9-122 | — | — | — | — |
| 239 | E. coli 9-125 | — | — | — | — |
| 240 | E. coli 13-12 | — | — | — | — |

TABLE 24

| No. | (Strain No.) | LT gene | Primer (a) + (b) | (c) + (d) | (e) + (d) |
|---|---|---|---|---|---|
| 241 | E. coli 13-11 | — | — | — | — |
| 242 | E. coli 225-2 | + | + | + | + |
| 243 | E. coli 225-3 | — | — | — | — |
| 244 | E. coli 225-5 | — | — | — | — |
| 245 | E. coli 229-1 | — | — | — | — |
| 246 | E. coli 229-4 | — | — | — | — |
| 247 | E. coli 230-2 | — | — | — | — |
| 248 | E. coli 230-5 | + | + | + | + |
| 249 | E. coli 232-1 | — | — | — | — |
| 250 | E. coli 232-3 | — | — | — | — |
| 251 | E. coli 234-1 | — | — | — | — |
| 252 | E. coli 234-4 | — | — | — | — |
| 253 | E. coli 235-1 | — | — | — | — |
| 254 | E. coli 235-2 | — | — | — | — |
| 255 | E. coli 238-1 | — | — | — | — |
| 256 | E. coli 238-2 | — | — | — | — |
| 257 | E. coli 238-3 | — | — | — | — |
| 258 | E. coli 238-4 | — | — | — | — |
| 259 | E. coli 240-3 | + | + | + | + |
| 260 | E. coli 245-1 | + | + | + | + |
| 261 | E. coli 245-2 | + | + | + | + |
| 262 | E. coli 245-3 | + | + | + | + |
| 263 | E. coli 245-4 | + | + | + | + |
| 264 | E. coli 245-5 | — | — | — | — |
| 265 | E. coli 252-1 | + | + | + | + |
| 266 | E. coli 252-2 | — | — | — | — |

TABLE 24-continued

| No. | (Strain No.) | LT gene | Primer (a) + (b) | (c) + (d) | (e) + (d) |
|---|---|---|---|---|---|
| 267 | E. coli 252-3 | — | — | — | — |
| 268 | E. coli 252-4 | — | — | — | — |
| 269 | E. coli 252-5 | — | — | — | — |
| 270 | E. coli 254-2 | — | — | — | — |
| 271 | E. coli 254-5 | — | — | — | — |
| 272 | E. coli 257-1 | — | — | — | — |
| 273 | E. coli 257-2 | — | — | — | — |
| 274 | E. coli 257-3 | — | — | — | — |
| 275 | E. coli 257-4 | — | — | — | — |
| 276 | E. coli 259-1 | — | — | — | — |
| 277 | E. coli 259-2 | — | — | — | — |
| 278 | E. coli 259-4 | — | — | — | — |
| 279 | E. coli 259-5 | — | — | — | — |
| 280 | E. coli 260-2 | — | — | — | — |

TABLE 25

| No. | (Strain No.) | LT gene | Primer (a) + (b) | (c) + (d) | (e) + (d) |
|---|---|---|---|---|---|
| 281 | E. coli 260-3 | + | + | + | + |
| 282 | E. coli 260-4 | + | + | + | + |
| 283 | E. coli 260-5 | + | + | + | + |
| 284 | E. coli 261-1 | + | + | + | + |
| 285 | E. coli 261-2 | — | — | — | — |
| 286 | E. coli 261-3 | — | — | — | — |
| 287 | E. coli 264-1 | — | — | — | — |
| 288 | E. coli 264-2 | — | — | — | — |
| 289 | E. coli 264-3 | — | — | — | — |
| 290 | E. coli 264-4 | — | — | — | — |
| 291 | E. coli 264-5 | — | — | — | — |
| 292 | E. coli 266-1 | — | — | — | — |
| 293 | E. coli 266-2 | — | — | — | — |
| 294 | E. coli 266-3 | + | + | + | + |
| 295 | E. coli 266-4 | — | — | — | — |
| 296 | E. coli 269-2 | — | — | — | — |
| 297 | E. coli 281-1 | — | — | — | — |
| 298 | E. coli 281-2 | — | — | — | — |
| 299 | E. coli 281-3 | — | — | — | — |
| 300 | E. coli 281-4 | — | — | — | — |
| 301 | E. coli 281-5 | — | — | — | — |
| 302 | E. coli 282-3 | — | — | — | — |
| 303 | E. coli 282-5 | — | — | — | — |
| 304 | E. coli 285-1 | — | — | — | — |
| 305 | E. coli 285-2 | — | — | — | — |
| 306 | E. coli 285-3 | — | — | — | — |
| 307 | E. coli 285-4 | — | — | — | — |
| 308 | E. coli 285-5 | — | — | — | — |
| 309 | E. coli 286-2 | — | — | — | — |
| 310 | E. coli 286-3 | — | — | — | — |
| 311 | E. coli 288-1 | — | — | — | — |
| 312 | E. coli 288-2 | — | — | — | — |
| 313 | E. coli 288-3 | + | + | + | + |
| 314 | E. coli 288-4 | + | + | + | + |
| 315 | E. coli 288-5 | — | — | — | — |
| 316 | E. coli 289-3 | + | + | + | + |
| 317 | E. coli 292-1 | — | — | — | — |
| 318 | E. coli 292-2 | — | — | — | — |
| 319 | E. coli 292-5 | — | — | — | — |
| 320 | E. coli 294-2 | + | + | + | + |

TABLE 26

| No. | (Strain No.) | LT gene | Primer (a) + (b) | (c) + (d) | (e) + (d) |
|---|---|---|---|---|---|
| 321 | E. coli 294-3 | — | — | — | — |
| 322 | E. coli 294-4 | + | + | + | + |
| 323 | E. coli 294-5 | — | — | — | — |
| 324 | E. coli 297-2 | — | — | — | — |
| 325 | E. coli 297-3 | — | — | — | — |
| 326 | E. coli 297-4 | — | — | — | — |
| 327 | E. coli 297-5 | — | — | — | — |
| 328 | E. coli 306-1 | — | — | — | — |
| 329 | E. coli 306-3 | — | — | — | — |
| 330 | E. coli 309-1 | + | + | + | + |
| 331 | E. coli 309-2 | + | + | + | + |
| 332 | E. coli 309-3 | — | — | — | — |
| 333 | E. coli 310-2 | — | — | — | — |
| 334 | E. coli 310-3 | — | — | — | — |
| 335 | E. coli 310-4 | — | — | — | — |
| 336 | E. coli 310-5 | — | — | — | — |
| 337 | E. coli 311-1 | — | — | — | — |
| 338 | E. coli 311-2 | — | — | — | — |
| 339 | E. coli 311-3 | + | + | + | + |
| 340 | E. coli 311-4 | — | — | — | — |
| 341 | E. coli 311-5 | + | + | + | + |
| 342 | E. coli 313-1 | + | + | + | + |
| 343 | E. coli 313-2 | — | — | — | — |
| 344 | E. coli 313-3 | — | — | — | — |
| 345 | E. coli 313-4 | — | — | — | — |
| 346 | E. coli 313-5 | — | — | — | — |
| 347 | E. coli 322-4 | + | + | + | + |
| 348 | E. coli 324-1 | + | + | + | + |
| 349 | E. coli 324-2 | + | + | + | + |
| 350 | E. coli 324-3 | — | — | — | — |
| 351 | E. coli 324-4 | + | + | + | + |
| 352 | E. coli 324-5 | — | — | — | — |
| 353 | E. coli 328-1 | + | + | + | + |
| 354 | E. coli 329-1 | — | — | — | — |
| 355 | E. coli 329-2 | — | — | — | — |
| 356 | E. coli 334-1 | + | + | + | + |
| 357 | E. coli 334-2 | + | + | + | + |
| 358 | E. coli 334-3 | + | + | + | + |
| 359 | E. coli 334-4 | + | + | + | + |
| 360 | E. coli 334-5 | + | + | + | + |

TABLE 27

| No. | (Strain No.) | LT gene | Primer (a) + (b) | (c) + (d) | (e) + (d) |
|---|---|---|---|---|---|
| 361 | E. coli 339-2 | — | — | — | — |
| 362 | E. coli 339-5 | — | — | — | — |
| 363 | E. coli 287-1 | — | — | — | — |
| 364 | E. coli 287-2 | — | — | — | — |
| 365 | E. coli 287-3 | — | — | — | — |
| 366 | E. coli 287-4 | — | — | — | — |
| 367 | E. coli 287-5 | + | + | + | + |
| 368 | E. coli 344-1 | — | — | — | — |
| 369 | E. coli 344-2 | — | — | — | — |
| 370 | E. coli 344-3 | — | — | — | — |
| 371 | E. coli 344-4 | — | — | — | — |
| 372 | E. coli 344-5 | — | — | — | — |
| 373 | E. coli 346-1 | — | — | — | — |
| 374 | E. coli 346-2 | — | — | — | — |
| 375 | E. coli 346-3 | — | — | — | — |
| 376 | E. coli 346-4 | — | — | — | — |
| 377 | E. coli 364-5 | — | — | — | — |
| 378 | E. coli 348-1 | + | + | + | + |
| 379 | E. coli 348-2 | — | — | — | — |
| 380 | E. coli 348-3 | — | — | — | — |
| 381 | E. coli 348-4 | — | — | — | — |
| 382 | E. coli 348-5 | — | — | — | — |
| 383 | E. coli 349-5 | — | — | — | — |
| 384 | E. coli 352-2 | — | — | — | — |
| 385 | E. coli 352-5 | — | — | — | — |
| 386 | E. coli 357-1 | + | + | + | + |
| 387 | E. coli 357-2 | — | — | — | — |
| 388 | E. coli 358-1 | — | — | — | — |
| 389 | E. coli 358-2 | — | — | — | — |
| 390 | E. coli 358-3 | — | — | — | — |

TABLE 27-continued

| No. | (Strain No.) | LT gene | Primer (a) + (b) | (c) + (d) | (e) + (d) |
|---|---|---|---|---|---|
| 391 | E. coli 361-3 | + | + | + | + |
| 392 | E. coli 361-4 | — | — | — | — |
| 393 | E. coli 361-5 | — | — | — | — |
| 394 | E. coli 366-1 | — | — | — | — |
| 395 | E. coli 383-4 | + | + | + | + |
| 396 | E. coli 383-5 | + | + | + | + |
| 397 | E. coli 384-1 | — | — | — | — |
| 398 | E. coli 385-1 | + | + | + | + |
| 399 | E. coli 385-2 | + | + | + | + |
| 400 | E. coli 385-3 | + | + | + | + |

TABLE 28

| No. | (Strain No.) | LT gene | Primer (a) + (b) | (c) + (d) | (e) + (d) |
|---|---|---|---|---|---|
| 401 | E. coli 385-4 | + | + | + | + |
| 402 | E. coli 385-5 | + | + | + | + |
| 403 | E. coli 392-1 | — | — | — | — |
| 404 | E. coli 392-2 | — | — | — | — |
| 405 | E. coli 392-3 | — | — | — | — |
| 406 | E. coli 392-5 | — | — | — | — |
| 407 | E. coli 402-1 | — | — | — | — |
| 408 | E. coli 402-2 | — | — | — | — |
| 409 | E. coli 402-3 | — | — | — | — |
| 410 | E. coli 402-4 | — | — | — | — |
| 411 | E. coli 402-5 | — | — | — | — |
| 412 | E. coli 409-2 | — | — | — | — |
| 413 | E. coli 409-3 | — | — | — | — |
| 414 | E. coli 409-4 | — | — | — | — |
| 415 | E. coli 409-5 | — | — | — | — |
| 416 | E. coli 417-1 | — | — | — | — |
| 417 | E. coli 417-2 | — | — | — | — |
| 418 | E. coli 417-3 | — | — | — | — |
| 419 | E. coli 417-4 | — | — | — | — |
| 420 | E. coli 417-5 | — | — | — | — |
| 421 | E. coli 412-4 | — | — | — | — |
| 422 | E. coli 421-2 | — | — | — | — |
| 423 | E. coli 421-3 | — | — | — | — |
| 424 | E. coli 429-3 | + | + | + | + |
| 425 | E. coli 429-5 | + | + | + | + |
| 426 | E. coli 430-1 | + | + | + | + |
| 427 | E. coli 430-3 | + | + | + | + |
| 428 | E. coli 433-1 | — | — | — | — |
| 429 | E. coli 433-2 | + | + | + | + |
| 430 | E. coli 433-3 | w | + | w | + |
| 431 | E. coli 433-4 | — | — | — | — |
| 432 | E. coli 434-1 | — | — | — | — |
| 433 | E. coli 434-2 | — | — | — | — |
| 434 | E. coli 434-4 | + | + | + | + |
| 435 | E. coli 434-5 | w | + | + | + |
| 436 | E. coli 441-1 | + | + | + | + |
| 437 | E. coli 486-3 | — | — | — | — |
| 438 | E. coli 486-4 | — | — | — | — |
| 439 | E. coli 486-5 | — | — | — | — |
| 440 | E. coli 490-2 | — | — | — | — |

TABLE 29

| No. | (Strain No.) | LT gene | Primer (a) + (b) | (c) + (d) | (e) + (d) |
|---|---|---|---|---|---|
| 441 | E. coli 513-1 | — | — | — | — |
| 442 | E. coli 513-2 | — | — | — | — |
| 443 | E. coli 513-3 | — | — | — | — |
| 444 | E. coli 513-5 | — | — | — | — |
| 445 | E. coli 514-1 | — | — | — | — |
| 446 | E. coli 514-2 | — | — | — | — |
| 447 | E. coli 514-3 | — | — | — | — |
| 448 | E. coli 514-5 | — | — | — | — |
| 449 | E. coli 514-4 | — | — | — | — |
| 450 | E. coli 524-2 | — | — | — | — |
| 451 | E. coli 524-5 | — | — | — | — |
| 452 | E. coli 530-2 | — | — | — | — |
| 453 | E. coli 530-3 | — | — | — | — |
| 454 | E. coli 530-4 | — | — | — | — |
| 455 | E. coli 530-5 | — | — | — | — |
| 456 | E. coli 531-3 | — | — | — | — |
| 457 | E. coli 536-1 | — | — | — | — |
| 458 | E. coli 536-2 | + | + | + | + |
| 459 | E. coli 536-5 | + | + | + | + |
| 460 | E. coli 554-1 | — | — | — | — |
| 461 | E. coli 554-2 | — | — | — | — |
| 462 | E. coli 554-3 | — | — | — | — |
| 463 | E. coli 554-4 | — | — | — | — |
| 464 | E. coli 554-5 | — | — | — | — |
| 465 | E. coli 568-1 | — | — | — | — |
| 466 | E. coli 568-2 | — | — | — | — |
| 467 | E. coli 568-4 | — | — | — | — |
| 468 | E. coli 568-3 | — | — | — | — |
| 469 | E. coli 578-1 | — | — | — | — |
| 470 | E. coli 578-2 | — | — | — | — |
| 471 | E. coli 578-4 | — | — | — | — |
| 472 | E. coli 578-5 | — | — | — | — |
| 473 | E. coli 590-1 | + | + | + | + |
| 474 | E. coli 590-2 | + | + | + | + |
| 475 | E. coli 590-3 | — | — | — | — |
| 476 | E. coli 590-4 | + | + | + | + |
| 477 | E. coli 590-5 | + | + | + | + |
| 478 | E. coli 591-1 | — | — | — | — |
| 479 | E. coli 591-2 | — | — | — | — |
| 480 | E. coli 591-3 | — | — | — | — |

TABLE 30

| No. | (Strain No.) | LT gene | Primer (a) + (b) | (c) + (d) | (e) + (d) |
|---|---|---|---|---|---|
| 481 | E. coli 591-4 | — | — | — | — |
| 482 | E. coli 592-5 | — | — | — | — |
| 483 | E. coli 599-1 | — | — | — | — |
| 484 | E. coli 599-2 | — | — | — | — |
| 485 | E. coli 599-3 | — | — | — | — |
| 486 | E. coli 599-4 | — | — | — | — |
| 487 | E. coli 599-5 | — | — | — | — |
| 488 | E. coli 603-4 | — | — | — | — |
| 489 | E. coli 604-1 | — | — | — | — |
| 490 | E. coli 604-2 | — | — | — | — |
| 491 | E. coli 604-3 | — | — | — | — |
| 492 | E. coli 617-1 | — | — | — | — |

TABLE 31

| No. | | (Strain No.) | Primer (a) + (b) | (c) + (d) | (e) + (d) |
|---|---|---|---|---|---|
| 1 | *Bacillus cereus* | ATCC 14579 | — | — | — |
| 2 | *Bacillus subtilis* | JCM 1465 | — | — | — |
| 3 | *Staphylococcus auveus* | JCM 2413 | — | — | — |
| 4 | *Staphylococcus epidermidis* | JCM 2414 | — | — | — |
| 5 | *Salmonella typhimurium* | IFO 12529 | — | — | — |
| 6 | *Salmonella enteritidis* | IFO 3163 | — | — | — |
| 7 | *Clostridium perfringens* | ATCC 12917 | — | — | — |
| 8 | *Vibrio cholerae* | ATCC 25872 | — | — | — |
| 9 | *Vibrio cholerae* type Ogawa | ATCC 9458 | — | — | — |
| 10 | *Vibrio cholerae* type Inaba | ATCC 9459 | — | — | — |
| 11 | *Vibrio fluvialis* | JCM 3752 | — | — | — |
| 12 | *Campylobacter jejuni* | JCM 2013 | — | — | — |
| 13 | *Campylobacter coli* | JCM 2529 | — | — | — |
| 14 | *E. coli* | JCM 1649 | — | — | — |
| 15 | *Yersinia enterocolitica* | ATCC 9610 | — | — | — |
| 16 | *Sigella dysenteriae* | ATCC 9361 | — | — | — |
| 17 | *Sigella flexneri* | ATCC 29903 | — | — | — |
| 18 | *Sigella sonnei* | ATCC 29930 | — | — | — |
| 19 | *Bacteroides flagilis* | ATCC 23745 | — | — | — |
| 20 | *Bacteroides vulgatus* | JCM 5826 | — | — | — |
| 21 | *Enterococcus feacalis* | JCM 5803 | — | — | — |
| 22 | *Klebsiella pneumoniae* | JCM 1662 | — | — | — |
| 23 | *Proteus vulgaris* | JCM 1668 | — | — | — |
| 24 | *Citrobacter freundil* | ATCC 33128 | — | — | — |
| 25 | *Streptococcus pyogenes* | ATCC 12344 | — | — | — |
| 26 | *Streptococcus pneumoniae* | ATCC 33400 | — | — | — |

TABLE 32

| No. | | (Strain No.) | Primer (a) + (b) | (c) + (d) | (e) + (d) |
|---|---|---|---|---|---|
| 27 | *Haemophilus influenzae* | ATCC 33391 | — | — | — |
| 28 | *Proteus mivabilis* | ATCC 29906 | — | — | — |
| 29 | *Neisseria gonorrheae* | ATCC 19424 | — | — | — |
| 30 | *Neisseria meningitidis* | ATCC 13077 | — | — | — |
| 31 | *Listeria monocygenes* | ATCC 15313 | — | — | — |
| 32 | *Lactobacillus acidophillus* | JCM 1132 | — | — | — |
| 33 | *Bifidobacterium adolescentis* | JCM 1275 | — | — | — |
| 34 | *Fusobacterium nucleatum* | ATCC 25586 | — | — | — |
| 35 | *Propiobacterium acnes* | ATCC 6919 | — | — | — |
| 36 | *Veillonella atypica* | ATCC 17744 | — | — | — |
| 37 | *Pseudomonas aeruginosa* | IFO 12689 | — | — | — |
| 38 | *Corinebacterium diphtheriae* | JCM 1310 | — | — | — |
| 39 | *Peptostreptococcus anaerobius* | ATCC 27337 | — | — | — |
| 40 | Human placental DNA | | — | — | — |
| 41 | *V. cholerae* O1 cix + | PB 1 | — | — | — |
| 42 | *V. cholerae* O1 cix + | SGN 7277 | — | — | — |
| 43 | *V. cholerae* O1 cix — | 1094-79 | — | — | — |
| 44 | *V. cholerae* O1 cix + | E 9120 | — | — | — |
| 45 | *V. cholerae* O1 cix + | E 506 | — | — | — |
| 46 | *V. cholerae* O1 cix + | PB 17 | — | — | — |
| 47 | *V. cholerae* O1 cix — | 61H-110 | — | — | — |
| 48 | *V. cholerae* O1 cix + | 61H-151 | — | — | — |
| 49 | *V. cholerae* O1 cix — | 56H-118 | — | — | — |
| 50 | *V. cholerae* O1 cix — | 56H-119 | — | — | — |
| 51 | *E. coli* | HB-101 | — | — | — |

TABLE 33

| No. | | (Strain No.) | Colony Hybr | | Primer combination | | | | |
|---|---|---|---|---|---|---|---|---|---|
| | | | STh | STp | a + b | c + e | d + e | d + h | g + h |
| 1 | *E. coli* | WHO1 | — | — | — | — | — | — | — |
| 2 | *E. coli* | WHO2 | + | — | + | + | + | — | — |
| 3 | *E. coli* | WHO3 | + | — | + | + | + | — | — |
| 4 | *E. coli* | WHO4 | — | — | — | — | — | — | — |
| 5 | *E. coli* | WHO5 | — | — | — | — | — | — | — |
| 6 | *E. coli* | WHO6 | — | — | — | — | — | — | — |
| 7 | *E. coli* | WHO7 | — | — | — | — | — | — | — |

TABLE 33-continued

| No. | (Strain No.) | | Colony Hybr | | Primer combination | | | |
|---|---|---|---|---|---|---|---|---|
| | | | STh | STp | a + b | c + e | d + e | d + h | g + h |
| 8  | E. coli | WHO8  | + | — | + | + | + | + | + |
| 9  | E. coli | WHO9  | — | + | + | — | — | + | + |
| 10 | E. coli | WHO10 | — | + | + | — | — | — | — |
| 11 | E. coli | WHO11 | + | — | + | + | + | — | — |
| 12 | E. coli | WHO12 | — | — | — | — | — | — | — |
| 13 | E. coli | WHO13 | + | — | + | + | + | — | — |
| 14 | E. coli | WHO14 | — | — | — | — | — | — | — |
| 15 | E. coli | WHO15 | — | — | — | — | — | — | — |
| 16 | E. coli | WHO16 | — | — | — | — | — | — | — |
| 17 | E. coli | WHO17 | — | — | — | — | — | — | — |
| 18 | E. coli | WHO18 | — | — | — | — | — | — | — |
| 19 | E. coli | WHO19 | — | — | — | — | — | — | — |
| 20 | E. coli | WHO20 | — | — | — | — | — | — | — |
| 21 | E. coli | WHO21 | + | — | + | + | + | — | — |
| 22 | E. coli | WHO22 | + | — | + | + | + | — | — |

TABLE 34

| No. | (Strain No.) | | Colony Hybr | | Primer combination | | | |
|---|---|---|---|---|---|---|---|---|
| | | | STh | STp | a + b | c + e | d + e | d + h | g + h |
| 23 | E. coli | WHO23 | — | — | — | — | — | — | — |
| 24 | E. coli | WHO24 | + | — | + | + | + | — | — |
| 25 | E. coli | WHO25 | — | — | — | — | — | — | — |
| 26 | E. coli | WHO26 | — | — | — | — | — | — | — |
| 27 | E. coli | WHO27 | — | — | — | — | — | — | — |
| 28 | E. coli | WHO28 | + | — | + | + | + | — | — |
| 29 | E. coli | WHO29 | + | — | + | + | + | — | — |
| 30 | E. coli | WHO30 | + | — | + | + | + | — | — |
| 31 | E. coli | WHO31 | — | — | — | — | — | — | — |
| 32 | E. coli | WHO32 | — | — | — | — | — | — | — |
| 33 | E. coli | WHO33 | — | — | — | — | — | — | — |
| 34 | E. coli | WHO34 | — | — | — | — | — | — | — |
| 35 | E. coli | WHO35 | — | — | — | — | — | — | — |
| 36 | E. coli | WHO36 | — | — | — | — | — | — | — |
| 37 | E. coli | WHO37 | — | — | — | — | — | — | — |
| 38 | E. coli | WHO38 | — | — | — | — | — | — | — |
| 39 | E. coli | WHO39 | + | — | + | + | + | — | — |
| 40 | E. coli | WHO40 | + | — | + | + | + | — | — |
| 41 | E. coli | WHO41 | — | — | — | — | — | — | — |
| 42 | E. coli | WHO42 | — | — | — | — | — | — | — |
| 43 | E. coli | WHO43 | — | — | — | — | — | — | — |
| 44 | E. coli | WHO44 | — | — | — | — | — | — | — |

TABLE 35

| No. | (Strain No.) | | Colony Hybr | | Primer combination | | | |
|---|---|---|---|---|---|---|---|---|
| | | | STh | STp | a + b | c + e | d + e | d + h | g + h |
| 45 | E. coli | WHO45 | + | — | + | + | + | — | — |
| 46 | E. coli | WHO46 | — | — | — | — | — | — | — |
| 47 | E. coli | WHO47 | — | + | + | — | — | + | + |
| 48 | E. coli | WHO48 | — | — | — | — | — | — | — |
| 49 | E. coli | WHO49 | — | — | — | — | — | — | — |
| 50 | E. coli | WHO50 | — | — | — | — | — | — | — |
| 51 | E. coli | WHO51 | — | — | — | — | — | — | — |
| 52 | E. coli | WHO52 | — | — | — | — | — | — | — |
| 53 | E. coli | WHO53 | — | — | — | — | — | — | — |
| 54 | E. coli | WHO54 | — | — | — | — | — | — | — |
| 55 | E. coli | WHO55 | — | — | — | — | — | — | — |
| 56 | E. coli | WHO56 | — | — | — | — | — | — | — |
| 57 | E. coli | WHO57 | — | + | + | — | — | + | + |
| 58 | E. coli | WHO58 | + | — | + | + | + | — | — |
| 59 | E. coli | WHO59 | — | — | — | — | — | — | — |
| 60 | E. coli | WHO60 | — | — | — | — | — | — | — |
| 61 | E. coli | WHO61 | — | — | — | — | — | — | — |
| 62 | E. coli | WHO62 | — | — | — | — | — | — | — |

TABLE 35-continued

| No. | (Strain No.) | Colony Hybr STh | Colony Hybr STp | Primer combination a+b | Primer combination c+e | Primer combination d+e | Primer combination d+h | Primer combination g+h |
|---|---|---|---|---|---|---|---|---|
| 63 | E. coli WHO63 | — | — | — | — | — | — | — |
| 64 | E. coli WHO64 | — | — | — | — | — | — | — |
| 65 | E. coli WHO65 | — | — | — | — | — | — | — |
| 66 | E. coli WHO66 | — | — | — | — | — | — | — |

TABLE 36

| No. | (Strain No.) | Colony Hybr STh | Colony Hybr STp | Primer combination a+b | Primer combination c+e | Primer combination d+e | Primer combination d+h | Primer combination g+h |
|---|---|---|---|---|---|---|---|---|
| 67 | E. coli WHO67 | — | — | — | — | — | + | + |
| 68 | E. coli WHO68 | — | + | + | — | — | — | — |
| 69 | E. coli WHO69 | — | — | — | — | — | — | — |
| 70 | E. coli WHO70 | + | — | + | + | + | — | — |
| 71 | E. coli WHO71 | — | — | — | — | — | — | — |
| 72 | E. coli WHO72 | — | — | — | — | — | — | — |
| 73 | E. coli WHO73 | — | — | — | — | — | — | — |
| 74 | E. coli WHO74 | — | — | — | — | — | — | — |
| 75 | E. coli WHO75 | — | — | — | — | — | — | — |
| 76 | E. coli WHO76 | — | — | — | — | — | — | — |
| 77 | E. coli WHO77 | — | — | — | — | — | — | — |
| 78 | E. coli WHO78 | — | — | — | — | — | — | — |
| 79 | E. coli WHO79 | — | — | — | — | — | — | — |
| 80 | E. coli WHO80 | — | — | — | — | — | — | — |
| 81 | E. coli WHO81 | + | — | + | + | + | — | — |
| 82 | E. coli WHO82 | — | — | — | — | — | — | — |
| 83 | E. coli WHO83 | — | — | — | — | — | — | — |
| 84 | E. coli WHO84 | — | — | — | — | — | — | — |
| 85 | E. coli WHO85 | — | — | — | — | — | — | — |
| 86 | E. coli WHO86 | — | — | — | — | — | — | — |
| 87 | E. coli WHO87 | — | — | — | — | — | — | — |
| 88 | E. coli WHO88 | — | — | — | — | — | — | — |

TABLE 37

| No. | (Strain No.) | Colony Hybr STh | Colony Hybr STp | Primer combination a+b | Primer combination c+e | Primer combination d+e | Primer combination d+h | Primer combination g+h |
|---|---|---|---|---|---|---|---|---|
| 89 | E. coli WHO89 | — | — | — | — | — | — | — |
| 90 | E. coli WHO90 | — | — | — | — | — | — | — |
| 91 | E. coli WHO91 | — | — | — | — | — | — | — |
| 92 | E. coli WHO92 | — | — | — | — | — | — | — |
| 93 | E. coli WHO93 | — | — | — | — | — | — | — |
| 94 | E. coli WHO94 | — | — | — | — | — | — | — |
| 95 | E. coli WHO95 | — | — | — | — | — | — | — |
| 96 | E. coli WHO96 | — | — | — | — | — | — | — |
| 97 | E. coli WHO97 | — | — | — | — | — | — | — |
| 98 | E. coli WHO98 | — | — | — | — | — | — | — |
| 99 | E. coli WHO99 | — | — | — | — | — | — | — |
| 100 | E. coli WHO100 | — | — | — | — | — | — | — |
| 101 | E. coli WHO101 | — | — | — | — | — | — | — |
| 102 | E. coli WHO102 | — | — | — | — | — | — | — |
| 103 | E. coli WHO103 | — | — | — | — | — | — | — |
| 104 | E. coli WHO104 | — | — | — | — | — | — | — |
| 105 | E. coli WHO105 | + | — | + | + | + | — | — |
| 106 | E. coli WHO106 | — | — | — | — | — | — | — |
| 107 | E. coli WHO107 | — | — | — | — | — | — | — |
| 108 | E. coli WHO108 | — | — | — | — | — | — | — |
| 109 | E. coli WHO109 | — | — | — | — | — | — | — |
| 110 | E. coli WHO110 | — | — | — | — | — | — | — |

TABLE 38

| No. | (Strain No.) | Colony Hybr STh | Colony Hybr STp | Primer combination a+b | Primer combination c+e | Primer combination d+e | Primer combination d+h | Primer combination g+h |
|---|---|---|---|---|---|---|---|---|
| 111 | E. coli WHO111 | — | — | — | — | — | — | — |

TABLE 38-continued

| | | Colony Hybr | | Primer combination | | | | |
|---|---|---|---|---|---|---|---|---|
| No. | (Strain No.) | STh | STp | a + b | c + e | d + e | d + h | g + h |
| 112 | E. coli WHO112 | — | — | — | — | — | — | — |
| 113 | E. coli WHO113 | — | — | — | — | — | — | — |
| 114 | E. coli WHO114 | — | — | — | — | — | — | — |
| 115 | E. coli WHO115 | + | — | + | + | + | — | — |
| 116 | E. coli WHO116 | — | — | — | — | — | — | — |
| 117 | E. coli WHO117 | — | — | — | — | — | — | — |
| 118 | E. coli WHO118 | — | — | — | — | — | — | — |
| 119 | E. coli WHO119 | — | — | — | — | — | — | — |
| 120 | E. coli WHO120 | — | — | — | — | — | — | — |
| 121 | E. coli WHO121 | — | — | — | — | — | — | — |
| 122 | E. coli WHO122 | + | — | + | + | + | — | — |
| 123 | E. coli WHO123 | — | — | — | — | — | — | — |
| 124 | E. coli WHO124 | — | — | — | — | — | — | — |
| 125 | E. coli WHO125 | + | — | + | + | + | — | — |
| 126 | E. coli WHO126 | — | — | — | — | — | — | — |
| 127 | E. coli WHO127 | — | — | — | — | — | — | — |
| 128 | E. coli WHO128 | — | — | — | — | — | — | — |
| 129 | E. coli WHO129 | — | — | — | — | — | — | — |
| 130 | E. coli WHO130 | + | — | + | + | + | — | — |
| 131 | E. coli WHO131 | — | — | — | — | — | — | — |
| 132 | E. coli WHO132 | + | — | + | + | + | — | — |

TABLE 39

| | | Colony Hybr | | Primer combination | | | | |
|---|---|---|---|---|---|---|---|---|
| No. | (Strain No.) | STh | STp | a + b | c + e | d + e | d + h | g + h |
| 133 | E. coli WHO133 | — | — | — | — | — | — | — |
| 134 | E. coli WHO134 | + | — | + | + | + | — | — |
| 135 | E. coli WHO135 | — | — | — | — | — | — | — |
| 136 | E. coli WHO136 | — | — | — | — | — | — | — |
| 137 | E. coli WHO137 | — | — | — | — | — | — | — |
| 138 | E. coli WHO138 | — | — | — | — | — | — | — |
| 139 | E. coli WHO139 | — | — | — | — | — | — | — |
| 140 | E. coli WHO140 | — | — | — | — | — | — | — |
| 141 | E. coli WHO141 | — | — | — | — | — | — | — |
| 142 | E. coli WHO142 | — | + | + | — | — | + | + |
| 143 | E. coli WHO143 | — | — | — | — | — | — | — |
| 144 | E. coli WHO144 | — | — | — | — | — | — | — |
| 145 | E. coli WHO145 | — | — | — | — | — | — | — |
| 146 | E. coli WHO146 | — | — | — | — | — | — | — |
| 147 | E. coli WHO147 | — | — | — | — | — | — | — |
| 148 | E. coli WHO148 | — | — | — | — | — | — | — |
| 149 | E. coli WHO149 | — | — | — | — | — | — | — |
| 150 | E. coli WHO150 | — | — | — | — | — | — | — |
| 151 | E. coli WHO151 | — | — | — | — | — | — | — |
| 152 | E. coli WHO152 | — | — | — | — | — | — | — |
| 153 | E. coli WHO153 | + | — | + | + | + | — | — |
| 154 | E. coli WHO154 | — | — | — | — | — | — | — |

TABLE 40

| | | Colony Hybr | | Primer combination | | | | |
|---|---|---|---|---|---|---|---|---|
| No. | (Strain No.) | STh | STp | a + b | c + e | d + e | d + h | g + h |
| 155 | E. coli WHO155 | — | — | — | — | — | — | — |
| 156 | E. coli WHO156 | — | — | — | — | — | — | — |
| 157 | E. coli WHO157 | — | — | — | — | — | — | — |
| 158 | E. coli WHO158 | — | — | — | — | — | — | — |
| 159 | E. coli WHO159 | — | — | — | — | — | — | — |
| 160 | E. coli WHO160 | + | — | + | + | + | — | — |
| 161 | E. coli WHO161 | — | — | — | — | — | — | — |
| 162 | E. coli WHO162 | — | — | — | — | — | — | — |
| 163 | E. coli WHO163 | — | — | — | — | — | — | — |
| 164 | E. coli WHO164 | + | — | + | + | + | — | — |
| 165 | E. coli WHO165 | — | — | — | — | — | — | — |
| 166 | E. coli WHO166 | — | — | — | — | — | — | — |
| 167 | E. coli WHO167 | — | — | — | — | — | — | — |
| 168 | E. coli WHO168 | — | + | + | — | — | + | + |
| 169 | E. coli WHO169 | — | — | — | — | — | — | — |

TABLE 40-continued

| No. | (Strain No.) | Colony Hybr | | Primer combination | | | | |
|---|---|---|---|---|---|---|---|---|
| | | STh | STp | a + b | c + e | d + e | d + h | g + h |
| 170 | E. coli WHO170 | — | — | — | — | — | — | — |
| 171 | E. coli WHO171 | — | — | — | — | — | — | — |
| 172 | E. coli WHO172 | — | — | — | — | — | — | — |
| 173 | E. coli WHO173 | — | — | — | — | — | — | — |
| 174 | E. coli WHO174 | — | — | — | — | — | — | — |
| 175 | E. coli WHO175 | — | — | — | — | — | — | — |
| 176 | E. coli WHO176 | — | — | — | — | — | — | — |

TABLE 41

| No | (Strain No.) | Colony Hybri | | Primer combination | | | | |
|---|---|---|---|---|---|---|---|---|
| | | STh | STp | a + b | c + e | d + e | f + h | g + h |
| 177 | E. coli WHO177 | — | — | — | — | — | — | — |
| 178 | E. coli WHO178 | — | + | + | — | — | + | + |
| 179 | E. coli WHO179 | — | — | — | — | — | — | — |
| 180 | E. coli WHO180 | — | — | — | — | — | — | — |
| 181 | E. coli WHO181 | — | — | — | — | — | — | — |
| 182 | E. coli WHO182 | — | — | — | — | — | — | — |
| 183 | E. coli WHO183 | + | — | + | + | + | — | — |
| 184 | E. coli WHO184 | — | — | — | — | — | — | — |
| 185 | E. coli WHO185 | W | — | + | + | + | — | — |
| 186 | E. coli WHO186 | + | — | + | + | + | — | — |
| 187 | E. coli WHO187 | — | — | — | — | — | — | — |
| 188 | E. coli WHO188 | — | — | — | — | — | — | — |
| 189 | E. coli WHO189 | — | — | — | — | — | — | — |
| 190 | E. coli WHO190 | + | — | + | + | + | — | — |
| 191 | E. coli WHO191 | — | + | + | — | — | + | + |
| 192 | E. coli WHO192 | — | — | — | — | — | — | — |
| 193 | E. coli WHO193 | — | — | — | — | — | — | — |
| 194 | E. coli WHO194 | — | — | — | — | — | — | — |
| 195 | E. coli WHO195 | — | — | — | — | — | — | — |
| 196 | E. coli WHO196 | — | + | + | — | — | — | — |
| 197 | E. coli WHO197 | — | — | — | — | — | — | — |
| 198 | E. coli WHO198 | — | — | — | — | — | — | — |

TABLE 42

| No | (Strain No.) | Colony Hybri | | Primer combination | | | | |
|---|---|---|---|---|---|---|---|---|
| | | STh | STp | a + b | c + e | d + e | f + h | g + h |
| 199 | E. coli WHO199 | — | — | — | — | — | — | — |
| 200 | E. coli WHO200 | — | — | — | — | — | — | — |
| 201 | E. coli 21-21 | + | — | + | + | + | — | — |
| 202 | E. coli 21-22 | + | — | + | + | + | — | — |
| 203 | E. coli 21-23 | + | — | + | + | + | — | — |
| 204 | E. coli 21-24 | + | — | + | + | + | — | — |
| 205 | E. coli 7-62 | — | — | — | — | — | — | — |
| 206 | E. coli 7-63 | — | — | — | — | — | — | — |
| 207 | E. coli 7-64 | — | — | — | — | — | — | — |
| 208 | E. coli 8-41 | + | — | + | + | + | — | — |
| 209 | E. coli 8-43 | — | — | — | — | — | — | — |
| 210 | E. coli 8-44 | + | — | + | + | + | — | — |
| 211 | E. coli 5-13 | — | — | — | — | — | — | — |
| 212 | E. coli 5-14 | — | — | — | — | — | — | — |
| 213 | E. coli 7-53 | — | — | — | — | — | — | — |
| 214 | E. coli 7-56 | — | — | — | — | — | — | — |
| 215 | E. coli 7-58 | — | — | — | — | — | — | — |
| 216 | E. coli 2-15-161 | — | — | — | — | — | — | — |
| 217 | E. coli 2-15-163 | — | — | — | — | — | — | — |
| 218 | E. coli 28-10-3 | — | — | — | — | — | — | — |
| 219 | E. coli 28-10-4 | — | — | — | — | — | — | — |
| 220 | E. coli 9-126 | — | — | — | — | — | — | — |

TABLE 43

| No | (Strain No.) | Colony Hybri STh | STp | Primer combination a + b | c + e | d + e | f + h | g + h |
|---|---|---|---|---|---|---|---|---|
| 221 | E. coli 9-127 | − | − | − | − | − | − | − |
| 222 | E. coli 2-9-212 | − | − | − | − | − | − | − |
| 223 | E. coli 2-9-213 | − | − | − | − | − | − | − |
| 224 | E. coli 2-9-214 | − | − | − | − | − | − | − |
| 225 | E. coli 9-215 | − | − | − | − | − | − | − |
| 226 | E. coli 14-13 | − | − | − | − | − | − | − |
| 227 | E. coli 14-14 | − | − | − | − | − | − | − |
| 228 | E. coli 5-11 | − | − | − | − | − | − | − |
| 229 | E. coli 5-12 | − | − | − | − | − | − | − |
| 230 | E. coli 13-13 | − | − | − | − | − | − | − |
| 231 | E. coli 13-15 | − | − | − | − | − | − | − |
| 232 | E. coli 13-21 | − | − | − | − | − | − | − |
| 233 | E. coli 13-22 | − | − | − | − | − | − | − |
| 234 | E. coli 13-23 | − | − | − | − | − | − | − |
| 235 | E. coli 13-24 | − | − | − | − | − | − | − |
| 236 | E. coli 14-15 | − | − | − | − | − | − | − |
| 237 | E. coli 14-16 | − | − | − | − | − | − | − |
| 238 | E. coli 9-122 | − | − | − | − | − | − | − |
| 239 | E. coli 9-125 | − | − | − | − | − | − | − |
| 240 | E. coli 13-12 | − | − | − | − | − | − | − |
| 241 | E. coli 13-11 | − | − | − | − | − | − | − |
| 242 | E. coli 225-2 | + | − | + | + | + | − | − |

TABLE 44

| No | (Strain No.) | Colony Hybri STh | STp | Primer combination a + b | c + e | d + e | f + h | g + h |
|---|---|---|---|---|---|---|---|---|
| 243 | E. coli 225-3 | − | − | − | − | − | − | − |
| 244 | E. coli 225-5 | + | − | + | + | + | − | − |
| 245 | E. coli 229-1 | − | − | − | − | − | − | − |
| 246 | E. coli 229-4 | − | − | − | − | − | − | − |
| 247 | E. coli 230-2 | − | − | − | − | − | − | − |
| 248 | E. coli 239-5 | − | − | − | − | − | − | − |
| 249 | E. coli 232-1 | − | − | − | − | − | − | − |
| 250 | E. coli 232-3 | − | − | − | − | − | − | − |
| 251 | E. coli 234-1 | − | − | − | − | − | − | − |
| 252 | E. coli 234-4 | − | − | − | − | − | − | − |
| 253 | E. coli 235-1 | + | − | + | + | + | − | − |
| 254 | E. coli 235-2 | + | − | + | + | + | − | − |
| 255 | E. coli 238-1 | − | − | − | − | − | − | − |
| 256 | E. coli 238-2 | − | − | − | − | − | − | − |
| 257 | E. coli 238-3 | − | − | − | − | − | − | − |
| 258 | E. coli 238-4 | − | − | − | − | − | − | − |
| 259 | E. coli 240-3 | − | − | − | − | − | − | − |
| 260 | E. coli 245-1 | − | − | − | − | − | − | − |
| 261 | E. coli 245-2 | + | − | + | + | + | − | − |
| 262 | E. coli 245-3 | − | − | − | − | − | − | − |
| 263 | E. coli 245-4 | + | − | + | + | + | − | − |
| 264 | E. coli 245-5 | − | − | − | − | − | − | − |

TABLE 45

| No | (Strain No.) | Colony Hybri STh | STp | Primer combination a + b | c + e | d + e | f + h | g + h |
|---|---|---|---|---|---|---|---|---|
| 265 | E. coli 252-1 | + | − | + | + | + | − | − |
| 266 | E. coli 252-2 | − | − | − | − | − | − | − |
| 267 | E. coli 252-3 | − | − | − | − | − | − | − |
| 268 | E. coli 252-4 | − | − | − | − | − | − | − |
| 269 | E. coli 252-5 | − | − | − | − | − | − | − |
| 270 | E. coli 254-2 | − | − | − | − | − | − | − |
| 271 | E. coli 254-5 | − | − | − | − | − | − | − |
| 272 | E. coli 257-1 | − | − | − | − | − | − | − |
| 273 | E. coli 257-2 | − | − | − | − | − | − | − |
| 274 | E. coli 257-3 | − | − | − | − | − | − | − |
| 275 | E. coli 257-4 | − | − | − | − | − | − | − |
| 276 | E. coli 259-1 | − | − | − | − | − | − | − |
| 277 | E. coli 259-2 | − | − | − | − | − | − | − |
| 278 | E. coli 259-4 | − | − | − | − | − | − | − |

TABLE 45-continued

| No | (Strain No.) | Colony Hybri | | Primer combination | | | |
| | | STh | STp | a + b | c + e | d + e | f + h | g + h |
| --- | --- | --- | --- | --- | --- | --- | --- | --- |
| 279 | E. coli 259-5 | − | − | − | − | − | − | − |
| 280 | E. coli 260-2 | − | − | − | − | − | − | − |
| 281 | E. coli 260-3 | − | − | − | − | − | − | − |
| 282 | E. coli 260-4 | − | − | − | − | − | − | − |
| 283 | E. coli 260-5 | − | − | − | − | − | − | − |
| 284 | E. coli 261-1 | − | + | + | − | − | + | + |
| 285 | E. coli 261-2 | − | − | − | − | − | − | − |
| 286 | E. coli 261-3 | − | − | − | − | − | − | − |

TABLE 46

| No | (Strain No.) | Colony Hybri | | Primer combination | | | |
| | | STh | STp | a + b | c + e | d + e | f + h | g + h |
| --- | --- | --- | --- | --- | --- | --- | --- | --- |
| 287 | E. coli 264-1 | + | − | + | + | + | − | − |
| 288 | E. coli 264-2 | + | − | + | + | + | − | − |
| 289 | E. coli 264-3 | + | − | + | + | + | − | − |
| 290 | E. coli 264-4 | + | − | + | + | + | − | − |
| 291 | E. coli 264-5 | + | − | + | + | + | − | − |
| 292 | E. coli 266-1 | + | − | + | + | + | − | − |
| 293 | E. coli 266-2 | + | − | + | + | + | − | − |
| 294 | E. coli 266-3 | − | + | + | − | − | + | + |
| 295 | E. coli 266-4 | + | − | + | + | + | − | − |
| 296 | E. coli 269-2 | − | − | − | − | − | − | − |
| 297 | E. coli 281-1 | − | − | − | − | − | − | − |
| 298 | E. coli 281-2 | + | − | + | + | + | − | − |
| 299 | E. coli 281-3 | + | − | + | + | + | − | − |
| 300 | E. coli 281-4 | + | − | + | + | + | − | − |
| 301 | E. coli 281-5 | + | − | + | + | + | − | − |
| 302 | E. coli 282-3 | + | − | + | + | + | − | − |
| 303 | E. coli 282-5 | + | − | + | + | + | − | − |
| 304 | E. coli 285-1 | − | − | − | − | − | − | − |
| 305 | E. coli 285-2 | − | − | − | − | − | − | − |
| 306 | E. coli 285-3 | − | − | − | − | − | − | − |
| 307 | E. coli 285-4 | − | − | − | − | − | − | − |
| 308 | E. coli 285-5 | − | − | − | − | − | − | − |

TABLE 47

| No | (Strain No.) | Colony Hybri | | Primer combination | | | |
| | | STh | STp | a + b | c + e | d + e | f + h | g + h |
| --- | --- | --- | --- | --- | --- | --- | --- | --- |
| 309 | E. coli 286-2 | − | − | − | − | − | − | − |
| 310 | E. coli 286-3 | − | − | − | − | − | − | − |
| 311 | E. coli 288-1 | − | − | − | − | − | − | − |
| 312 | E. coli 288-2 | − | − | − | − | − | − | − |
| 313 | E. coli 288-3 | − | − | − | − | − | − | − |
| 314 | E. coli 288-4 | + | − | + | + | + | − | − |
| 315 | E. coli 288-5 | − | − | − | − | − | − | − |
| 316 | E. coli 289-3 | − | + | + | − | − | + | + |
| 317 | E. coli 292-1 | − | − | − | − | − | − | − |
| 318 | E. coli 292-2 | − | − | − | − | − | − | − |
| 319 | E. coli 292-5 | − | − | − | − | − | − | − |
| 320 | E. coli 294-2 | − | − | − | − | − | − | − |
| 321 | E. coli 294-3 | − | − | − | − | − | − | − |
| 322 | E. coli 294-4 | − | − | − | − | − | − | − |
| 323 | E. coli 294-5 | − | − | − | − | − | − | − |
| 324 | E. coli 297-2 | − | − | − | − | − | − | − |
| 325 | E. coli 297-3 | − | − | − | − | − | − | − |
| 326 | E. coli 297-4 | − | − | − | − | − | − | − |
| 327 | E. coli 297-5 | − | − | − | − | − | − | − |
| 328 | E. coli 306-1 | − | − | − | − | − | − | − |
| 329 | E. coli 306-3 | − | − | − | − | − | − | − |
| 330 | E. coli 309-1 | − | + | + | − | − | + | + |

TABLE 48

| No | (Strain No.) | Colony Hybri | | Primer combination | | | | |
|---|---|---|---|---|---|---|---|---|
| | | STh | STp | a + b | c + e | d + e | f + h | g + h |
| 331 | E. coli 309-2 | − | + | + | − | − | + | + |
| 332 | E. coli 309-3 | − | − | − | − | − | − | − |
| 333 | E. coli 310-2 | − | − | − | − | − | − | − |
| 334 | E. coli 310-3 | − | − | − | − | − | − | − |
| 335 | E. coli 310-4 | − | − | − | − | − | − | − |
| 336 | E. coli 310-5 | − | − | − | − | − | − | − |
| 337 | E. coli 311-1 | − | − | − | − | − | − | − |
| 338 | E. coli 311-2 | − | − | − | − | − | − | − |
| 339 | E. coli 311-3 | − | − | − | − | − | − | − |
| 340 | E. coli 311-4 | − | − | − | − | − | − | − |
| 341 | E. coli 311-5 | − | − | − | − | − | − | − |
| 342 | E. coli 313-1 | − | + | + | − | − | + | + |
| 343 | E. coli 313-2 | − | − | − | − | − | − | − |
| 344 | E. coli 313-3 | − | − | − | − | − | − | − |
| 345 | E. coli 313-4 | − | − | − | − | − | − | − |
| 346 | E. coli 313-5 | − | − | − | − | − | − | − |
| 347 | E. coli 322-4 | − | − | − | − | − | − | − |
| 348 | E. coli 324-1 | + | − | + | + | + | − | − |
| 349 | E. coli 324-2 | − | − | − | − | − | − | − |
| 350 | E. coli 324-3 | − | − | − | − | − | − | − |
| 351 | E. coli 324-4 | + | − | + | + | + | − | − |
| 352 | E. coli 324-5 | − | − | − | − | − | − | − |

TABLE 49

| No | (Strain No.) | Colony Hybri | | Primer combination | | | | |
|---|---|---|---|---|---|---|---|---|
| | | STh | STp | a + b | c + e | d + e | f + h | g + h |
| 353 | E. coli 328-1 | − | − | − | − | − | − | − |
| 354 | E. coli 329-1 | − | − | − | − | − | − | − |
| 355 | E. coli 329-2 | + | − | + | + | + | − | − |
| 356 | E. coli 334-1 | − | + | + | − | − | + | + |
| 357 | E. coli 334-2 | − | + | + | − | − | + | + |
| 358 | E. coli 334-3 | − | + | + | − | − | + | + |
| 359 | E. coli 334-4 | − | + | + | − | − | + | + |
| 360 | E. coli 334-5 | − | + | + | − | − | + | + |
| 361 | E. coli 339-2 | − | − | − | − | − | − | − |
| 362 | E. coli 339-5 | − | − | − | − | − | − | − |
| 363 | E. coli 287-1 | − | − | − | − | − | − | − |
| 364 | E. coli 287-2 | − | − | − | − | − | − | − |
| 365 | E. coli 287-3 | − | − | − | − | − | − | − |
| 366 | E. coli 287-4 | − | − | − | − | − | − | − |
| 367 | E. coli 287-5 | + | − | + | + | + | − | − |
| 368 | E. coli 344-1 | − | − | − | − | − | − | − |
| 369 | E. coli 344-2 | − | − | − | − | − | − | − |
| 370 | E. coli 344-3 | − | − | − | − | − | − | − |
| 371 | E. coli 344-4 | − | − | − | − | − | − | − |
| 372 | E. coli 344-5 | − | − | − | − | − | − | − |
| 373 | E. coli 346-1 | − | − | − | − | − | − | − |
| 374 | E. coli 346-2 | − | − | − | − | − | − | − |

TABLE 50

| No | (Strain No.) | Colony Hybri | | Primer combination | | | | |
|---|---|---|---|---|---|---|---|---|
| | | STh | STp | a + b | c + e | d + e | f + h | g + h |
| 375 | E. coli 346-3 | − | − | − | − | − | − | − |
| 376 | E. coli 346-4 | − | − | − | − | − | − | − |
| 377 | E. coli 364-5 | − | − | − | − | − | − | − |
| 378 | E. coli 348-1 | − | − | − | − | − | − | − |
| 379 | E. coli 348-2 | − | − | − | − | − | − | − |
| 380 | E. coli 348-3 | − | − | − | − | − | − | − |
| 381 | E. coli 348-4 | − | − | − | − | − | − | − |
| 382 | E. coli 348-5 | − | − | − | − | − | − | − |
| 383 | E. coli 349-5 | + | − | + | + | + | − | − |
| 384 | E. coli 352-2 | − | − | − | − | − | − | − |
| 385 | E. coli 352-5 | − | − | − | − | − | − | − |
| 386 | E. coli 357-1 | + | − | + | + | + | − | − |
| 387 | E. coli 357-2 | − | − | − | − | − | − | − |
| 388 | E. coli 358-1 | − | − | − | − | − | − | − |

TABLE 50-continued

| No | (Strain No.) | Colony Hybri STh | STp | Primer combination a + b | c + e | d + e | f + h | g + h |
|---|---|---|---|---|---|---|---|---|
| 389 | E. coli 358-2 | − | − | − | − | − | − | − |
| 390 | E. coli 358-3 | − | − | − | − | − | − | − |
| 391 | E. coli 361-3 | + | − | + | + | + | − | − |
| 392 | E. coli 361-4 | − | − | − | − | − | − | − |
| 393 | E. coli 361-5 | − | − | − | − | − | − | − |
| 394 | E. coli 366-1 | + | − | + | + | + | − | − |
| 395 | E. coli 383-4 | − | − | − | − | − | − | − |
| 396 | E. coli 383-5 | − | − | − | − | − | − | − |

TABLE 51

| No. | (Strain No.) | Colony Hybr. STh | STp | Primer combination a + b | c + e | d + e | f + h | g + h |
|---|---|---|---|---|---|---|---|---|
| 397 | E. coli 384-1 | − | − | − | − | − | − | − |
| 398 | E. coli 385-1 | − | − | − | − | − | − | − |
| 399 | E. coli 385-2 | − | − | − | − | − | − | − |
| 400 | E. coli 385-3 | − | − | − | − | − | − | − |
| 401 | E. coli 385-4 | − | − | − | − | − | − | − |
| 402 | E. coli 385-5 | − | − | − | − | − | − | − |
| 403 | E. coli 392-1 | − | − | − | − | − | − | − |
| 404 | E. coli 392-2 | − | − | − | − | − | − | − |
| 405 | E. coli 392-3 | − | − | − | − | − | − | − |
| 406 | E. coli 392-5 | − | − | − | − | − | − | − |
| 407 | E. coli 402-1 | − | − | − | − | − | − | − |
| 408 | E. coli 402-2 | − | − | − | − | − | − | − |
| 409 | E. coli 402-3 | − | − | − | − | − | − | − |
| 410 | E. coli 402-4 | − | − | − | − | − | − | − |
| 411 | E. coli 402-5 | − | − | − | − | − | − | − |
| 412 | E. coli 409-2 | + | − | + | + | + | − | − |
| 413 | E. coli 409-3 | + | − | + | + | + | − | − |
| 414 | E. coli 409-4 | + | − | + | + | + | − | − |
| 415 | E. coli 409-5 | + | − | + | + | + | − | − |
| 416 | E. coli 417-1 | − | − | − | − | − | − | − |
| 417 | E. coli 417-2 | − | − | − | − | − | − | − |
| 418 | E. coli 417-3 | − | − | − | − | − | − | − |

TABLE 52

| No. | (Strain No.) | Colony Hybr. STh | STp | Primer combination a + b | c + e | d + e | f + h | g + h |
|---|---|---|---|---|---|---|---|---|
| 419 | E. coli 417-4 | + | − | + | + | + | − | − |
| 420 | E. coli 417-5 | + | − | + | + | + | − | − |
| 421 | E. coli 412-4 | + | − | + | + | + | − | − |
| 422 | E. coli 421-2 | + | − | + | + | + | − | − |
| 423 | E. coli 421-3 | + | − | + | + | + | − | − |
| 424 | E. coli 429-3 | − | − | − | − | − | − | − |
| 425 | E. coli 429-5 | − | − | − | − | − | − | − |
| 426 | E. coli 430-1 | − | − | − | − | − | − | − |
| 427 | E. coli 430-3 | − | − | − | − | − | − | − |
| 428 | E. coli 433-1 | − | + | + | − | − | + | + |
| 429 | E. coli 433-2 | − | + | + | − | − | + | + |
| 430 | E. coli 433-3 | − | − | − | − | − | − | − |
| 431 | E. coli 433-4 | − | − | − | − | − | − | − |
| 432 | E. coli 434-1 | − | − | − | − | − | − | − |
| 433 | E. coli 434-2 | − | − | − | − | − | − | − |
| 434 | E. coli 434-4 | − | − | − | − | − | − | − |
| 435 | E. coli 434-5 | − | − | − | − | − | − | − |
| 436 | E. coli 441-1 | − | − | − | − | − | − | − |
| 437 | E. coli 486-3 | − | − | − | − | − | − | − |
| 438 | E. coli 486-4 | − | − | − | − | − | − | − |
| 439 | E. coli 486-5 | − | − | − | − | − | − | − |

TABLE 52-continued

| No. | (Strain No.) | Colony Hybr. STh | STp | Primer combination a + b | c + e | d + e | f + h | g + h |
|---|---|---|---|---|---|---|---|---|
| 440 | E. coli 490-2 | + | − | + | + | + | − | − |

TABLE 53

| No. | (Strain No.) | Colony Hybr. STh | STp | Primer combination a + b | c + e | d + e | f + h | g + h |
|---|---|---|---|---|---|---|---|---|
| 441 | E. coli 513-1 | + | − | + | + | + | − | − |
| 442 | E. coli 513-2 | + | − | + | + | + | − | − |
| 443 | E. coli 513-3 | − | − | − | − | − | − | − |
| 444 | E. coli 513-5 | + | − | + | + | + | − | − |
| 445 | E. coli 514-1 | + | − | + | + | + | − | − |
| 446 | E. coli 514-2 | − | − | − | − | − | − | − |
| 447 | E. coli 514-3 | + | − | + | + | + | − | − |
| 448 | E. coli 514-5 | + | − | + | + | + | − | − |
| 449 | E. coli 514-4 | + | − | + | + | + | − | − |
| 450 | E. coli 524-2 | + | − | + | + | + | − | − |
| 451 | E. coli 524-5 | − | − | − | − | − | − | − |
| 452 | E. coli 530-2 | − | − | − | − | − | − | − |
| 453 | E. coli 530-3 | − | − | − | − | − | − | − |
| 454 | E. coli 530-4 | − | − | − | − | − | − | − |
| 455 | E. coli 530-5 | − | − | − | − | − | − | − |
| 456 | E. coli 531-3 | − | − | − | − | − | − | − |
| 457 | E. coli 536-1 | − | − | − | − | − | − | − |
| 458 | E. coli 536-2 | − | − | − | − | − | − | − |
| 459 | E. coli 536-5 | − | − | − | − | − | − | − |
| 460 | E. coli 554-1 | − | − | − | − | − | − | − |
| 461 | E. coli 554-2 | − | − | − | − | − | − | − |
| 462 | E. coli 554-3 | − | − | − | − | − | − | − |

TABLE 54

| No. | (Strain No.) | Colony Hybr. STh | STp | Primer combination a + b | c + e | d + e | f + h | g + h |
|---|---|---|---|---|---|---|---|---|
| 463 | E. coli 554-4 | − | − | − | − | − | − | − |
| 464 | E. coli 554-5 | − | − | − | − | − | − | − |
| 465 | E. coli 568-1 | − | − | − | − | − | − | − |
| 466 | E. coli 568-2 | + | − | + | + | + | − | − |
| 467 | E. coli 568-4 | − | − | − | − | − | − | − |
| 468 | E. coli 568-3 | − | − | − | − | − | − | − |
| 469 | E. coli 578-1 | + | − | + | + | + | − | − |
| 470 | E. coli 578-2 | − | − | − | − | − | − | − |
| 471 | E. coli 578-4 | + | − | + | + | + | − | − |
| 472 | E. coli 578-5 | − | − | − | − | − | − | − |
| 473 | E. coli 590-1 | − | − | − | − | − | − | − |

TABLE 54-continued

| | | Colony Hybr. | | Primer combination | | | | |
|---|---|---|---|---|---|---|---|---|
| No. | (Strain No.) | STh | STp | a + b | c + e | d + e | f + h | g + h |
| 474 | E. coli 590-2 | − | − | − | − | − | − | − |
| 475 | E. coli 590-3 | − | − | − | − | − | − | − |
| 476 | E. coli 590-4 | − | − | − | − | − | − | − |
| 477 | E. coli 590-5 | − | − | − | − | − | − | − |
| 478 | E. coli 591-1 | − | − | − | − | − | − | − |
| 479 | E. coli 591-2 | − | − | − | − | − | − | − |
| 480 | E. coli 591-3 | − | − | − | − | − | − | − |
| 481 | E. coli 591-4 | − | − | − | − | − | − | − |
| 482 | E. coli 592-5 | − | − | − | − | − | − | − |
| 483 | E. coli 599-1 | − | − | − | − | − | − | − |
| 484 | E. coli 599-2 | − | − | − | − | − | − | − |

TABLE 55

| | | | STh | | | STp | | |
|---|---|---|---|---|---|---|---|---|
| No. | Name | | a + b | c + e | d + e | a + b | f + h | g + h |
| 1 | Bacillus cereus | ATCC 14579 | − | − | − | − | − | − |
| 2 | Bacillus subtilis | JCM 1465 | − | − | − | − | − | − |
| 3 | Staphylococcus aureus | JCM 2413 | − | − | − | − | − | − |
| 4 | Staphylococcus epidermidis | JCM 2414 | − | − | − | − | − | − |
| 5 | Salmonella typhimurium | IFO 12529 | − | − | − | − | − | − |
| 6 | Salmonella enteritidis | IFO 3183 | − | − | − | − | − | − |
| 7 | Clostridium perfringens | ATCC 12917 | − | − | − | − | − | − |
| 8 | Vibrio cholerae | ATCC 25872 | − | − | − | − | − | − |
| 9 | Vibrio cholerae type ogawa | ATCC 9458 | − | − | − | − | − | − |
| 10 | Vibrio cholerae type inaba | ATCC 9459 | − | − | − | − | − | − |
| 11 | Vibrio fluvialis | JCM 3752 | − | − | − | − | − | − |
| 12 | Campylobacter jejuni | JCM 2013 | − | − | − | − | − | − |
| 13 | Campylobacter coli | JCM 2529 | − | − | − | − | − | − |
| 14 | Escherichia coli | JCM 1649 | − | − | − | − | − | − |
| 15 | Yersinia enterocolitica | ATCC 9810 | − | − | − | − | − | − |
| 16 | Shigella dysenteriae | ATCC 9361 | − | − | − | − | − | − |
| 17 | Shigella flexneri | ATCC 29903 | − | − | − | − | − | − |
| 18 | Shigella sonnei | ATCC 29930 | − | − | − | − | − | − |
| 19 | Bacteroides fragilis | ATCC 23745 | − | − | − | − | − | − |
| 20 | Bacteroides vulgatus | JCM 5826 | − | − | − | − | − | − |

TABLE 56

| | | | STh | | | STp | | |
|---|---|---|---|---|---|---|---|---|
| No. | Name | | a + b | c + e | d + e | a + b | f + h | g + h |
| 21 | Enterococcus faecalis | JCM 6803 | − | − | − | − | − | − |
| 22 | Klebsiella pneumoniae | JCM 1682 | − | − | − | − | − | − |
| 23 | Proteus vulgaris | JCM 1668 | − | − | − | − | − | − |
| 24 | Citrobacter freundii | ATCC 33128 | − | − | − | − | − | − |
| 25 | Streptococcus pyogenes | ATCC 12344 | − | − | − | − | − | − |
| 26 | Streptococcus pneumoniae | ATCC 33400 | − | − | − | − | − | − |
| 27 | Haemophilus influenzae | ATCC 33391 | − | − | − | − | − | − |
| 28 | Proteus mirabilis | ATCC 29906 | − | − | − | − | − | − |
| 29 | Neisseria gonorrhoeae | ATCC 19424 | − | − | − | − | − | − |
| 30 | Neisseria meningitidis | ATCC 13077 | − | − | − | − | − | − |
| 31 | Listeria monocytogenes | ATCC 15313 | − | − | − | − | − | − |
| 32 | Lactobacillus acidophilus | JCM 1132 | − | − | − | − | − | − |
| 33 | Bifidobacterium adolescentis | JCM 1275 | − | − | − | − | − | − |
| 34 | Fusobacterium nucleatum | ATCC 25586 | − | − | − | − | − | − |
| 35 | Propionibacterium acnes | ATCC 5919 | − | − | − | − | − | − |
| 36 | Veillonella atypica | ATCC 17744 | − | − | − | − | − | − |
| 37 | Pseudomonas aeruginosa | IFO 12689 | − | − | − | − | − | − |
| 38 | Corynebacterium diphtheriae | JCM 1310 | − | − | − | − | − | − |
| 39 | Peptostreptococcus anaerobius | ATCC 27337 | − | − | − | − | − | − |
| 40 | Human placental DNA | | − | − | − | − | − | − |

TABLE 57

| No. | Name | | STh | | | STp | | |
|---|---|---|---|---|---|---|---|---|
| | | | a + b | c + e | d + e | a + b | f + h | g + h |
| 41 | Vibrio cholerae 01 | PB1 | − | − | − | − | − | − |
| 42 | Vibrio cholerae 01 | SGN 7277 | − | − | − | − | − | − |
| 43 | Vibrio cholerae 01 | 1094-79 | − | − | − | − | − | − |
| 44 | Vibrio cholerae 01 | E 9120 | − | − | − | − | − | − |
| 45 | Vibrio cholerae 01 | E 506 | − | − | − | − | − | − |
| 46 | Vibrio cholerae 01 | PB 17 | − | − | − | − | − | − |
| 47 | Vibrio cholerae 01 | 61H-110 | − | − | − | − | − | − |
| 48 | Vibrio cholerae 01 | 61H-151 | − | − | − | − | − | − |
| 49 | Vibrio cholerae 01 | 56H-118 | − | − | − | − | − | − |

TABLE 58

| No. | RPLA | PCR primer combination | | | | | | | PCR primer combination | | | | |
|---|---|---|---|---|---|---|---|---|---|---|---|---|---|
| | | a + f | b + d | b + e | b + f | c + d | c + e | c + f | g + k | h + j | h + k | h + l | i + k |
| 1 | AB | + | + | + | + | + | + | + | + | + | + | + | + |
| 2 | AB | + | + | + | + | + | + | + | + | + | + | + | + |
| 3 | — | − | − | − | − | − | − | − | − | − | − | − | − |
| 4 | A | + | + | + | + | + | + | + | − | − | − | − | − |
| 5 | A | + | + | + | + | + | + | + | − | − | − | − | − |
| 6 | A | + | + | + | + | + | + | + | − | − | − | − | − |
| 7 | A | + | + | + | + | + | + | + | − | − | − | − | − |
| 8 | A | + | + | + | + | + | + | + | − | − | − | − | − |
| 9 | A | + | + | + | + | + | + | + | − | − | − | − | − |
| 10 | — | − | − | − | − | − | − | − | − | − | − | − | − |
| 11 | A | + | + | + | + | + | + | + | − | − | − | − | − |
| 12 | A | + | + | + | + | + | + | + | − | − | − | − | − |
| 13 | A | + | + | + | + | + | + | + | − | − | − | − | − |
| 14 | A | + | + | + | + | + | + | + | − | − | − | − | − |
| 15 | A | + | + | + | + | + | + | + | − | − | − | − | − |
| 16 | A | + | + | + | + | + | + | + | − | − | − | − | − |
| 17 | A | + | + | + | + | + | + | + | − | − | − | − | − |
| 18 | A | + | + | + | + | + | + | + | − | − | − | − | − |
| 19 | A | + | + | + | + | + | + | + | − | − | − | − | − |
| 20 | A | + | + | + | + | + | + | + | − | − | − | − | − |
| 21 | — | − | − | − | − | − | − | − | − | − | − | − | − |
| 22 | A | + | + | + | + | + | + | + | − | − | − | − | − |
| 23 | A | + | + | + | + | + | + | + | − | − | − | − | − |
| 24 | A | + | + | + | + | + | + | + | − | − | − | − | − |
| 25 | A | + | + | + | + | + | + | + | − | − | − | − | − |
| 26 | A | + | + | + | + | + | + | + | − | − | − | − | − |
| 27 | D | − | − | − | − | − | − | − | − | − | − | − | − |
| 28 | D | − | − | − | − | − | − | − | − | − | − | − | − |
| 29 | — | − | − | − | − | − | − | − | − | − | − | − | − |
| 30 | D | − | − | − | − | − | − | − | − | − | − | − | − |

| No. | PCR primer combination | | | | PCR primer combination | | |
|---|---|---|---|---|---|---|---|
| | m + g | n + q | o + q | o + r | s + z | t + z | u + x |
| 1 | − | − | − | − | − | − | − |
| 2 | − | − | − | − | − | − | − |
| 3 | − | − | − | − | − | − | − |
| 4 | − | − | − | − | − | − | − |
| 5 | − | − | − | − | − | − | − |
| 6 | − | − | − | − | − | − | − |
| 7 | − | − | − | − | − | − | − |
| 8 | − | − | − | − | − | − | − |
| 9 | − | − | − | − | − | − | − |
| 10 | − | − | − | − | − | − | − |
| 11 | − | − | − | − | − | − | − |
| 12 | − | − | − | − | − | − | − |
| 13 | − | − | − | − | − | − | − |
| 14 | − | − | − | − | − | − | − |
| 15 | − | − | − | − | − | − | − |
| 16 | − | − | − | − | − | − | − |
| 17 | − | − | − | − | − | − | − |
| 18 | − | − | − | − | − | − | − |
| 19 | − | − | − | − | − | − | − |

TABLE 58-continued

| | | | | | | | |
|---|---|---|---|---|---|---|---|
| 20 | − | − | − | − | − | − | − |
| 21 | − | − | − | − | − | − | − |
| 22 | − | − | − | − | − | − | − |
| 23 | − | − | − | − | − | − | − |
| 24 | − | − | − | − | − | − | − |
| 25 | − | − | − | − | − | − | − |
| 26 | − | − | − | − | − | − | − |
| 27 | − | − | − | − | + | + | + |
| 28 | − | − | − | − | + | + | + |
| 29 | − | − | − | − | − | − | − |
| 30 | − | − | − | − | + | + | + |

TABLE 59

| No. | RPLA | PCR primer combination | | | | | | | PCR primer combination | | | | |
|---|---|---|---|---|---|---|---|---|---|---|---|---|---|
| | | a+f | b+d | b+e | b+f | c+d | c+e | c+f | g+k | h+j | h+k | h+l | i+k |
| 31 | D | − | − | − | − | − | − | − | − | − | − | − | − |
| 32 | A | + | + | + | + | + | + | + | − | − | − | − | − |
| 33 | A | + | + | + | + | + | + | + | − | − | − | − | − |
| 34 | A | + | + | + | + | + | + | + | − | − | − | − | − |
| 35 | C | − | − | − | − | − | − | − | − | − | − | − | − |
| 36 | D | − | − | − | − | − | − | − | − | − | − | − | − |
| 37 | C | − | − | − | − | − | − | − | − | − | − | − | − |
| 38 | — | − | − | − | − | − | − | − | − | − | − | − | − |
| 39 | — | − | − | − | − | − | − | − | − | − | − | − | − |
| 40 | C | − | − | − | − | − | − | − | − | − | − | − | − |
| 41 | C | − | − | − | − | − | − | − | − | − | − | − | − |
| 42 | — | − | − | − | − | − | − | − | − | − | − | − | − |
| 43 | D | − | − | − | − | − | − | − | − | − | − | − | − |
| 44 | — | − | − | − | − | − | − | − | − | − | − | − | − |
| 45 | C | − | − | − | − | − | − | − | − | − | − | − | − |
| 46 | C | − | − | − | − | − | − | − | − | − | − | − | − |
| 47 | — | − | − | − | − | − | − | − | − | − | − | − | − |
| 48 | D | − | − | − | − | − | − | − | − | − | − | − | − |
| 49 | — | − | − | − | − | − | − | − | − | − | − | − | − |
| 50 | C | − | − | − | − | − | − | − | − | − | − | − | − |
| 51 | — | − | − | − | − | − | − | − | − | − | − | − | − |
| 52 | C | − | − | − | − | − | − | − | − | − | − | − | − |
| 53 | C | − | − | − | − | − | − | − | − | − | − | − | − |
| 54 | C | − | − | − | − | − | − | − | − | − | − | − | − |
| 55 | C | − | − | − | − | − | − | − | − | − | − | − | − |
| 56 | — | − | − | − | − | − | − | − | − | − | − | − | − |
| 57 | C | − | − | − | − | − | − | − | − | − | − | − | − |
| 58 | — | − | − | − | − | − | − | − | − | − | − | − | − |
| 59 | — | − | − | − | − | − | − | − | − | − | − | − | − |
| 60 | — | − | − | − | − | − | − | − | − | − | − | − | − |

| No. | PCR primer combination | | | | PCR primer combination | | |
|---|---|---|---|---|---|---|---|
| | m+g | n+q | o+q | o+r | s+z | t+z | u+x |
| 31 | − | − | − | − | + | + | + |
| 32 | − | − | − | − | − | − | − |
| 33 | − | − | − | − | − | − | − |
| 34 | − | − | − | − | − | − | − |
| 35 | + | + | + | + | − | − | − |
| 36 | − | − | − | − | + | + | + |
| 37 | + | + | + | + | − | − | − |
| 38 | − | − | − | − | − | − | − |
| 39 | − | − | − | − | − | − | − |
| 40 | + | + | + | + | − | − | − |
| 41 | + | + | + | + | − | − | − |
| 42 | − | − | − | − | − | − | − |
| 43 | − | − | − | − | + | + | + |
| 44 | − | − | − | − | − | − | − |
| 45 | + | + | + | + | − | − | − |
| 46 | + | + | + | + | − | − | − |
| 47 | − | − | − | − | − | − | − |
| 48 | − | − | − | − | + | + | + |
| 49 | − | − | − | − | − | − | − |
| 50 | + | + | + | + | − | − | − |
| 51 | − | − | − | − | − | − | − |
| 52 | + | + | + | + | − | − | − |

TABLE 59-continued

| | | | | | | | |
|---|---|---|---|---|---|---|---|
| 53 | + | + | + | + | − | − | − |
| 54 | + | + | + | + | − | − | − |
| 55 | + | + | + | + | − | − | − |
| 56 | − | − | − | − | − | − | − |
| 57 | + | + | + | + | − | − | − |
| 58 | − | − | − | − | − | − | − |
| 59 | − | − | − | − | − | − | − |
| 60 | − | − | − | − | − | − | − |

TABLE 60

| No. | RPLA | PCR primer combination | | | | | | | PCR primer combination | | | | |
|---|---|---|---|---|---|---|---|---|---|---|---|---|---|
| | | a + f | b + d | b + e | b + f | c + d | c + e | c + f | g + k | h + j | h + k | h + l | i + k |
| 61 | — | − | − | − | − | − | − | − | − | − | − | − | − |
| 62 | — | − | − | − | − | − | − | − | − | − | − | − | − |
| 63 | — | − | − | − | − | − | − | − | − | − | − | − | − |
| 64 | — | − | − | − | − | − | − | − | − | − | − | − | − |
| 65 | — | − | − | − | − | − | − | − | − | − | − | − | − |
| 66 | — | − | − | − | − | − | − | − | − | − | − | − | − |
| 67 | D | − | − | − | − | − | − | − | − | − | − | − | − |
| 68 | D | − | − | − | − | − | − | − | − | − | − | − | − |
| 69 | AD | + | + | + | + | + | + | + | − | − | − | − | − |
| 70 | D | − | − | − | − | − | − | − | − | − | − | − | − |
| 71 | D | − | − | − | − | − | − | − | − | − | − | − | − |
| 72 | C | − | − | − | − | − | − | − | − | − | − | − | − |
| 73 | AB | + | + | + | + | + | + | + | + | + | + | + | + |
| 74 | AB | + | + | + | + | + | + | + | + | + | + | + | + |
| 75 | AB | + | + | + | + | + | + | + | + | + | + | + | + |
| 76 | AB | + | + | + | + | + | + | + | + | + | + | + | + |
| 77 | A | + | + | + | + | + | + | + | − | − | − | − | − |
| 78 | A | + | + | + | + | + | + | + | − | − | − | − | − |
| 79 | A | + | + | + | + | + | + | + | − | − | − | − | − |
| 80 | A | + | + | + | + | + | + | + | − | − | − | − | − |
| 81 | — | − | − | − | − | − | − | − | − | − | − | − | − |
| 82 | A | + | + | + | + | + | + | + | − | − | − | − | − |
| 83 | A | + | + | + | + | + | + | + | − | − | − | − | − |
| 84 | A | + | + | + | + | + | + | + | − | − | − | − | − |
| 85 | A | + | + | + | + | + | + | + | − | − | − | − | − |
| 86 | A | + | + | + | + | + | + | + | − | − | − | − | − |
| 87 | A | + | + | + | + | + | + | + | − | − | − | − | − |
| 88 | A | + | + | + | + | + | + | + | − | − | − | − | − |
| 89 | AB | + | + | + | + | + | + | + | + | + | + | + | + |
| 90 | AB | + | + | + | + | + | + | + | + | + | + | + | + |

| No. | PCR primer combination | | | | PCR primer combination | | |
|---|---|---|---|---|---|---|---|
| | m + g | n + q | o + q | o + r | s + z | t + z | u + x |
| 61 | − | − | − | − | − | − | − |
| 62 | − | − | − | − | − | − | − |
| 63 | − | − | − | − | − | − | − |
| 64 | − | − | − | − | − | − | − |
| 65 | − | − | − | − | − | − | − |
| 66 | − | − | − | − | − | − | − |
| 67 | − | − | − | − | + | + | + |
| 68 | − | − | − | − | + | + | + |
| 69 | − | − | − | − | + | + | + |
| 70 | − | − | − | − | + | + | + |
| 71 | − | − | − | − | + | + | + |
| 72 | + | + | + | + | − | − | − |
| 73 | − | − | − | − | − | − | − |
| 74 | − | − | − | − | − | − | − |
| 75 | − | − | − | − | − | − | − |
| 76 | − | − | − | − | − | − | − |
| 77 | − | − | − | − | − | − | − |
| 78 | − | − | − | − | − | − | − |
| 79 | − | − | − | − | − | − | − |
| 80 | − | − | − | − | − | − | − |
| 81 | − | − | − | − | − | − | − |
| 82 | − | − | − | − | − | − | − |
| 83 | − | − | − | − | − | − | − |
| 84 | − | − | − | − | − | − | − |
| 85 | − | − | − | − | − | − | − |

TABLE 60-continued

| | | | | | | | |
|---|---|---|---|---|---|---|---|
| 86 | – | – | – | – | – | – | – |
| 87 | – | – | – | – | – | – | – |
| 88 | – | – | – | – | – | – | – |
| 89 | – | – | – | – | – | – | – |
| 90 | – | – | – | – | – | – | – |

TABLE 61

| No. | RPLA | PCR primer combination | | | | | | | PCR primer combination | | | | |
|---|---|---|---|---|---|---|---|---|---|---|---|---|---|
| | | a + f | b + d | b + e | b + f | c + d | c + e | c + f | g + k | h + j | h + k | h + l | i + k |
| 91 | AB | + | + | + | + | + | + | + | + | + | + | + | + |
| 92 | AB | + | + | + | + | + | + | + | + | + | + | + | + |
| 93 | — | – | – | – | – | – | – | – | – | – | – | – | – |
| 94 | — | – | – | – | – | – | – | – | – | – | – | – | – |
| 95 | — | – | – | – | – | – | – | – | – | – | – | – | – |
| 96 | — | – | – | – | – | – | – | – | – | – | – | – | – |
| 97 | — | – | – | – | – | – | – | – | – | – | – | – | – |
| 98 | — | – | – | – | – | – | – | – | – | – | – | – | – |
| 99 | A | + | + | + | + | + | + | + | – | – | – | – | – |
| 100 | — | – | – | – | – | – | – | – | – | – | – | – | – |
| 101 | — | – | – | – | – | – | – | – | – | – | – | – | – |
| 102 | — | – | – | – | – | – | – | – | – | – | – | – | – |
| 103 | — | – | – | – | – | – | – | – | – | – | – | – | – |
| 104 | — | – | – | – | – | – | – | – | – | – | – | – | – |
| 105 | A | + | + | + | + | + | + | + | – | – | – | – | – |
| 106 | A | + | + | + | + | + | + | + | – | – | – | – | – |
| 107 | A | + | + | + | + | + | + | + | – | – | – | – | – |
| 108 | A | + | + | + | + | + | + | + | – | – | – | – | – |
| 109 | AD | + | + | + | + | + | + | + | – | – | – | – | – |
| 110 | AD | + | + | + | + | + | + | + | – | – | – | – | – |
| 111 | AD | + | + | + | + | + | + | + | – | – | – | – | – |
| 112 | D | – | – | – | – | – | – | – | – | – | – | – | – |
| 113 | A | + | + | + | + | + | + | + | – | – | – | – | – |
| 114 | A | + | + | + | + | + | + | + | – | – | – | – | – |
| 115 | A | + | + | + | + | + | + | + | – | – | – | – | – |
| 116 | A | + | + | + | + | + | + | + | – | – | – | – | – |
| 117 | A | + | + | + | + | + | + | + | – | – | – | – | – |
| 118 | A | + | + | + | + | + | + | + | – | – | – | – | – |
| 119 | A | + | + | + | + | + | + | + | – | – | – | – | – |
| 120 | A | + | + | + | + | + | + | + | – | – | – | – | – |

| No. | PCR primer combination | | | | PCR primer combination | | |
|---|---|---|---|---|---|---|---|
| | m + g | n + q | o + q | o + r | s + z | t + z | u + x |
| 91 | – | – | – | – | – | – | – |
| 92 | – | – | – | – | – | – | – |
| 93 | – | – | – | – | – | – | – |
| 94 | – | – | – | – | – | – | – |
| 95 | – | – | – | – | – | – | – |
| 96 | – | – | – | – | – | – | – |
| 97 | – | – | – | – | – | – | – |
| 98 | – | – | – | – | – | – | – |
| 99 | – | – | – | – | – | – | – |
| 100 | – | – | – | – | – | – | – |
| 101 | – | – | – | – | – | – | – |
| 102 | – | – | – | – | – | – | – |
| 103 | – | – | – | – | – | – | – |
| 104 | – | – | – | – | – | – | – |
| 105 | – | – | – | – | – | – | – |
| 106 | – | – | – | – | – | – | – |
| 107 | – | – | – | – | – | – | – |
| 108 | – | – | – | – | – | – | – |
| 109 | – | – | – | – | + | + | + |
| 110 | – | – | – | – | + | + | + |
| 111 | – | – | – | – | + | + | + |
| 112 | – | – | – | – | + | + | + |
| 113 | – | – | – | – | – | – | – |
| 114 | – | – | – | – | – | – | – |
| 115 | – | – | – | – | – | – | – |
| 116 | – | – | – | – | – | – | – |
| 117 | – | – | – | – | – | – | – |
| 118 | – | – | – | – | – | – | – |

TABLE 61-continued

| | | | | | | | |
|---|---|---|---|---|---|---|---|
| 119 | − | − | − | − | − | − | − |
| 120 | − | − | − | − | − | − | − |

TABLE 62

| | | PCR primer combination | | | | | | | PCR primer combination | | | |
|---|---|---|---|---|---|---|---|---|---|---|---|---|
| No. | RPLA | a + f | b + d | b + e | b + f | c + d | c + e | c + f | g + k | h + j | h + k | h + l | i + k |
| 121 | A | + | + | + | + | + | + | + | − | − | − | − | − |
| 122 | — | − | − | − | − | − | − | − | − | − | − | − | − |
| 123 | — | − | − | − | − | − | − | − | − | − | − | − | − |
| 124 | — | − | − | − | − | − | − | − | − | − | − | − | − |
| 125 | A | + | + | + | + | + | + | + | − | − | − | − | − |
| 126 | A | + | + | + | + | + | + | + | − | − | − | − | − |
| 127 | A | + | + | + | + | + | + | + | − | − | − | − | − |
| 128 | — | − | − | − | − | − | − | − | − | − | − | − | − |
| 129 | — | − | − | − | − | − | − | − | − | − | − | − | − |
| 130 | — | − | − | − | − | − | − | − | − | − | − | − | − |
| 131 | — | − | − | − | − | − | − | − | − | − | − | − | − |
| 132 | − | − | − | − | − | − | − | − | − | − | − | − | − |
| 133 | A | + | + | + | + | + | + | + | − | − | − | − | − |
| 134 | B | − | − | − | − | − | − | − | + | + | + | + | + |
| 135 | C, D | − | − | − | − | − | − | − | − | − | − | − | − |
| 136 | D | − | − | − | − | − | − | − | − | − | − | − | − |
| 137 | — | − | − | − | − | − | − | − | − | − | − | − | − |
| 138 | — | − | − | − | − | − | − | − | − | − | − | − | − |
| 139 | — | − | − | − | − | − | − | − | − | − | − | − | − |
| 140 | — | − | − | − | − | − | − | − | − | − | − | − | − |
| 141 | A | + | + | + | + | + | + | + | − | − | − | − | − |
| 142 | B | − | − | − | − | − | − | − | + | + | + | + | + |
| 143 | — | − | − | − | − | − | − | − | − | − | − | − | − |
| 144 | B | − | − | − | − | − | − | − | + | + | + | + | + |
| 145 | — | − | − | − | − | − | − | − | − | − | − | − | − |
| 146 | — | − | − | − | − | − | − | − | − | − | − | − | − |
| 147 | — | − | − | − | − | − | − | − | − | − | − | − | − |
| 148 | — | − | − | − | − | − | − | − | − | − | − | − | − |
| 149 | AB | + | + | + | + | + | + | + | + | + | + | + | + |
| 150 | AB | + | + | + | + | + | + | + | + | + | + | + | + |

| No. | PCR primer combination | | | | PCR primer combination | | |
|---|---|---|---|---|---|---|---|
| | m + g | n + q | o + q | o + r | s + z | t + z | u + x |
| 121 | − | − | − | − | − | − | − |
| 122 | − | − | − | − | − | − | − |
| 123 | − | − | − | − | − | − | − |
| 124 | − | − | − | − | − | − | − |
| 125 | − | − | − | − | − | − | − |
| 126 | − | − | − | − | − | − | − |
| 127 | − | − | − | − | − | − | − |
| 128 | − | − | − | − | − | − | − |
| 129 | − | − | − | − | − | − | − |
| 130 | − | − | − | − | − | − | − |
| 131 | − | − | − | − | − | − | − |
| 132 | − | − | − | − | − | − | − |
| 133 | − | − | − | − | + | + | + |
| 134 | − | − | − | − | − | − | − |
| 135 | + | + | + | + | + | + | + |
| 136 | − | − | − | − | + | + | + |
| 137 | − | − | − | − | − | − | − |
| 138 | − | − | − | − | − | − | − |
| 139 | − | − | − | − | − | − | − |
| 140 | − | − | − | − | − | − | − |
| 141 | − | − | − | − | − | − | − |
| 142 | − | − | − | − | − | − | − |
| 143 | − | − | − | − | + | + | + |
| 144 | − | − | − | − | − | − | − |
| 145 | − | − | − | − | − | − | − |
| 146 | − | − | − | − | − | − | − |
| 147 | − | − | − | − | − | − | − |
| 148 | − | − | − | − | + | + | + |
| 149 | − | − | − | − | − | − | − |
| 150 | − | − | − | − | − | − | − |

TABLE 63

| No. | RPLA | PCR primer combination | | | | | | | PCR primer combination | | | | |
|-----|------|-----|-----|-----|-----|-----|-----|-----|-----|-----|-----|-----|-----|
|     |      | a+f | b+d | b+e | b+f | c+d | c+e | c+f | g+k | h+j | h+k | h+l | i+k |
| 151 | AB   | +   | +   | +   | +   | +   | +   | +   | +   | +   | +   | +   | +   |
| 152 | AB   | +   | +   | +   | +   | +   | +   | +   | +   | +   | +   | +   | +   |
| 153 | AB   | +   | +   | +   | +   | +   | +   | +   | +   | +   | +   | +   | +   |
| 154 | AB   | +   | +   | +   | +   | +   | +   | +   | +   | +   | +   | +   | +   |
| 155 | —    | —   | —   | —   | —   | —   | —   | —   | —   | —   | —   | —   | —   |
| 156 | —    | —   | —   | —   | —   | —   | —   | —   | —   | —   | —   | —   | —   |
| 157 | —    | —   | —   | —   | —   | —   | —   | —   | —   | —   | —   | —   | —   |

| No. | PCR primer combination | | | | PCR primer combination | | |
|-----|-----|-----|-----|-----|-----|-----|-----|
|     | m+g | n+q | o+q | o+r | s+z | t+z | u+x |
| 151 | —   | —   | —   | —   | —   | —   | —   |
| 152 | —   | —   | —   | —   | —   | —   | —   |
| 153 | —   | —   | —   | —   | —   | —   | —   |
| 154 | —   | —   | —   | —   | —   | —   | —   |
| 155 | —   | —   | —   | —   | —   | —   | —   |
| 156 | —   | —   | —   | —   | —   | —   | —   |
| 157 | —   | —   | —   | —   | —   | —   | —   |

TABLE 64

| No. | Name | | PCR primer combination | | | | | | |
|-----|------|---|-----|-----|-----|-----|-----|-----|-----|
|     |      |   | a+f | b+d | b+a | b+f | c+d | c+e | c+f |
| 1   | *Bacillus cereus* | ATCC 14579 | — | — | — | — | — | — | — |
| 2   | *Bacillus subtilis* | JCK 1465 | — | — | — | — | — | — | — |
| 3   | *Staphylococcus epidermidis* | JCK 2414 | — | — | — | — | — | — | — |
| 4   | *Salmonella typhimurius* | IFO 12529 | — | — | — | — | — | — | — |
| 5   | *Salmonella enteritidis* | IFO 3163 | — | — | — | — | — | — | — |
| 6   | *Clostridium perfringens* | ATCC 12917 | — | — | — | — | — | — | — |
| 7   | *Vibrio cholerae* | ATCC 25872 | — | — | — | — | — | — | — |
| 8   | *Vibrio cholerae* type ogawa | ATCC 9458 | — | — | — | — | — | — | — |
| 9   | *Vibrio cholerae* type inaba | ATCC 9459 | — | — | — | — | — | — | — |
| 10  | *Vibrio fluvialis* | JCM 3752 | — | — | — | — | — | — | — |
| 11  | *Campylobacter jejuni* | JCM 2013 | — | — | — | — | — | — | — |
| 12  | *Campylobacter coli* | JCM 2529 | — | — | — | — | — | — | — |
| 13  | *Escherichia coli* | JCM 1649 | — | — | — | — | — | — | — |
| 14  | *Yersinia enterocolitica* | ATCC 9610 | — | — | — | — | — | — | — |
| 15  | *Shigella dysenteriae* | ATCC 9361 | — | — | — | — | — | — | — |
| 16  | *Shigella flexneri* | ATCC 29903 | — | — | — | — | — | — | — |
| 17  | *Shigella sonnei* | ATCC 29930 | — | — | — | — | — | — | — |
| 18  | *Bacteroides fragilis* | ATCC 23745 | — | — | — | — | — | — | — |
| 19  | *Bacteroides vulgatus* | JCM 5826 | — | — | — | — | — | — | — |
| 20  | *Enterococcus iaocalis* | JCM 5802 | — | — | — | — | — | — | — |
| 21  | *Klebsiella pneumoniae* | JCM 1652 | — | — | — | — | — | — | — |
| 22  | *Proteus vulgaris* | JCM 1668 | — | — | — | — | — | — | — |
| 23  | *Citrobacter freundii* | ATCC 33123 | — | — | — | — | — | — | — |
| 24  | *Streptococcus pyogenes* | ATCC 12344 | — | — | — | — | — | — | — |
| 25  | *Streptococcus pneumoniae* | ATCC 33400 | — | — | — | — | — | — | — |
| 26  | *Haemophilus influenzae* | ATCC 33391 | — | — | — | — | — | — | — |
| 27  | *Proteus mirabilis* | ATCC 23906 | — | — | — | — | — | — | — |
| 28  | *Neisseria gonorrhoeae* | ATCC 19424 | — | — | — | — | — | — | — |
| 29  | *Neisseria meningitidis* | ATCC 13877 | — | — | — | — | — | — | — |
| 30  | *Listeria monocytogenes* | ATCC 15313 | — | — | — | — | — | — | — |
| 31  | *Lactobacillus acidophilus* | JCK 1132 | — | — | — | — | — | — | — |
| 32  | *Bifidobacterium adolescentis* | JCK 1275 | — | — | — | — | — | — | — |
| 33  | *Fusobacterium nucleatum* | ATCC 25586 | — | — | — | — | — | — | — |
| 34  | *Propionibacterium acnes* | ATCC 6919 | — | — | — | — | — | — | — |
| 35  | *Veillonella atypica* | ATCC 17744 | — | — | — | — | — | — | — |
| 36  | *Pseudomonas aeruginosa* | IFO 12689 | — | — | — | — | — | — | — |
| 37  | *Corynebacterium diphteriae* | JCM 1310 | — | — | — | — | — | — | — |
| 38  | *Peptostreptococcus anaerobius* | ATCC 27337 | — | — | — | — | — | — | — |
| 39  | Human placental DNA | | — | — | — | — | — | — | — |

TABLE 64-continued

|   |   |   | PCR primer combination ||||| 
|---|---|---|---|---|---|---|---|
| No. | Name | | g + k | h + j | h + k | h + l | l + k |
| 1 | Bacillus cereus | ATCC 14579 | - | - | - | - | - |
| 2 | Bacillus subtilis | JCK 1465 | - | - | - | - | - |
| 3 | Staphylococcus epidermidis | JCK 2414 | - | - | - | - | - |
| 4 | Salmonella typhimurius | IFO 12529 | - | - | - | - | - |
| 5 | Salmonella enteritidis | IFO 3163 | - | - | - | - | - |
| 6 | Clostridium perfringens | ATCC 12917 | - | - | - | - | - |
| 7 | Vibrio cholerae | ATCC 25872 | - | - | - | - | - |
| 8 | Vibrio cholerae type ogawa | ATCC 9458 | - | - | - | - | - |
| 9 | Vibrio cholerae type inaba | ATCC 9459 | - | - | - | - | - |
| 10 | Vibrio fluvialis | JCM 3752 | - | - | - | - | - |
| 11 | Campylobacter jejuni | JCM 2013 | - | - | - | - | - |
| 12 | Campylobacter coli | JCM 2529 | - | - | - | - | - |
| 13 | Escherichia coli | JCM 1649 | - | - | - | - | - |
| 14 | Yersinia enterocolitica | ATCC 9610 | - | - | - | - | - |
| 15 | Shigella dysenteriae | ATCC 9361 | - | - | - | - | - |
| 16 | Shigella flexneri | ATCC 29903 | - | - | - | - | - |
| 17 | Shigella sonnei | ATCC 29930 | - | - | - | - | - |
| 18 | Bacteroides fragilis | ATCC 23745 | - | - | - | - | - |
| 19 | Bacteroides vulgatus | JCM 5826 | - | - | - | - | - |
| 20 | Enterococcus iaocalis | JCM 5802 | - | - | - | - | - |
| 21 | Klebsiella pneumoniae | JCM 1652 | - | - | - | - | - |
| 22 | Proteus vulgaris | JCM 1668 | - | - | - | - | - |
| 23 | Citrobacter freundii | ATCC 33123 | - | - | - | - | - |
| 24 | Streptococcus pyogenes | ATCC 12344 | - | - | - | - | - |
| 25 | Streptococcus pneumoniae | ATCC 33400 | - | - | - | - | - |
| 26 | Haemophilus influenzae | ATCC 33391 | - | - | - | - | - |
| 27 | Proteus mirabilis | ATCC 23906 | - | - | - | - | - |
| 28 | Neisseria gonorrhoeae | ATCC 19424 | - | - | - | - | - |
| 29 | Neisseria meningitidis | ATCC 13877 | - | - | - | - | - |
| 30 | Listeria monocytogenes | ATCC 15313 | - | - | - | - | - |
| 31 | Lactobacillus acidophilus | JCK 1132 | - | - | - | - | - |
| 32 | Bifidobacterium adolescentis | JCK 1275 | - | - | - | - | - |
| 33 | Fusobacterium nucleatum | ATCC 25586 | - | - | - | - | - |
| 34 | Propionibacterium acnes | ATCC 6919 | - | - | - | - | - |
| 35 | Veillonella atypica | ATCC 17744 | - | - | - | - | - |
| 36 | Pseudomonas aeruginosa | IFO 12689 | - | - | - | - | - |
| 37 | Corynebacterium diphteriae | JCM 1310 | - | - | - | - | - |
| 38 | Peptostreptococcus anaerobius | ATCC 27337 | - | - | - | - | - |
| 39 | Human placental DNA | | - | - | - | - | - |

|   |   |   | PCR primer combination |||| PCR primer combination |||
|---|---|---|---|---|---|---|---|---|---|
| No. | Name | | m + q | n + q | o + q | o + r | s + z | t + z | u + x |
| 1 | Bacillus cereus | ATCC 14579 | - | - | - | - | - | - | - |
| 2 | Bacillus subtilis | JCK 1465 | - | - | - | - | - | - | - |
| 3 | Staphylococcus epidermidis | JCK 2414 | - | - | - | - | - | - | - |
| 4 | Salmonella typhimurius | IFO 12529 | - | - | - | - | - | - | - |
| 5 | Salmonella enteritidis | IFO 3163 | - | - | - | - | - | - | - |
| 6 | Clostridium perfringens | ATCC 12917 | - | - | - | - | - | - | - |
| 7 | Vibrio cholerae | ATCC 25872 | - | - | - | - | - | - | - |
| 8 | Vibrio cholerae type ogawa | ATCC 9458 | - | - | - | - | - | - | - |
| 9 | Vibrio cholerae type inaba | ATCC 9459 | - | - | - | - | - | - | - |
| 10 | Vibrio fluvialis | JCM 3752 | - | - | - | - | - | - | - |
| 11 | Campylobacter jejuni | JCM 2013 | - | - | - | - | - | - | - |
| 12 | Campylobacter coli | JCM 2529 | - | - | - | - | - | - | - |
| 13 | Escherichia coli | JCM 1649 | - | - | - | - | - | - | - |
| 14 | Yersinia enterocolitica | ATCC 9610 | - | - | - | - | - | - | - |
| 15 | Shigella dysenteriae | ATCC 9361 | - | - | - | - | - | - | - |
| 16 | Shigella flexneri | ATCC 29903 | - | - | - | - | - | - | - |
| 17 | Shigella sonnei | ATCC 29930 | - | - | - | - | - | - | - |
| 18 | Bacteroides fragilis | ATCC 23745 | - | - | - | - | - | - | - |
| 19 | Bacteroides vulgatus | JCM 5826 | - | - | - | - | - | - | - |
| 20 | Enterococcus iaocalis | JCM 5802 | - | - | - | - | - | - | - |
| 21 | Klebsiella pneumoniae | JCM 1652 | - | - | - | - | - | - | - |
| 22 | Proteus vulgaris | JCM 1668 | - | - | - | - | - | - | - |
| 23 | Citrobacter freundii | ATCC 33123 | - | - | - | - | - | - | - |
| 24 | Streptococcus pyogenes | ATCC 12344 | - | - | - | - | - | - | - |

TABLE 64-continued

| | | | | | | | | | |
|---|---|---|---|---|---|---|---|---|---|
| 25 | Streptococcus pneumoniae | ATCC 33400 | − | − | − | − | − | − | − |
| 26 | Haemophilus influenzae | ATCC 33391 | − | − | − | − | − | − | − |
| 27 | Proteus mirabilis | ATCC 23906 | − | − | − | − | − | − | − |
| 28 | Neisseria gonorrhoeae | ATCC 19424 | − | − | − | − | − | − | − |
| 29 | Neisseria meningitidis | ATCC 13877 | − | − | − | − | − | − | − |
| 30 | Listeria monocytogenes | ATCC 15313 | − | − | − | − | − | − | − |
| 31 | Lactobacillus acidophilus | JCK 1132 | − | − | − | − | − | − | − |
| 32 | Bifidobacterium adolescentis | JCK 1275 | − | − | − | − | − | − | − |
| 33 | Fusobacterium nucleatum | ATCC 25586 | − | − | − | − | − | − | − |
| 34 | Propionibacterium acnes | ATCC 6919 | − | − | − | − | − | − | − |
| 35 | Veillonella atypica | ATCC 17744 | − | − | − | − | − | − | − |
| 36 | Pseudomonas aeruginosa | IFO 12689 | − | − | − | − | − | − | − |
| 37 | Corynebacterium diphteriae | JCM 1310 | − | − | − | − | − | − | − |
| 38 | Peptostreptococcus anaerobius | ATCC 27337 | − | − | − | − | − | − | − |
| 39 | Human placental DNA | | − | − | − | − | − | − | − |

TABLE 65

| S. aureus strain No. | RPLA | Primer combination | | | |
|---|---|---|---|---|---|
| | | a + d | a + f | b + c | b + e |
| 69 | A, D | − | − | − | − |
| 83 | A | − | − | − | − |
| FRI-722 | A, D | − | − | − | − |
| 553 | A | − | − | − | − |
| 1 | A, B | − | − | − | − |
| FDA-243 (ATCC14458) | B | − | − | − | − |
| 213 | B | − | − | − | − |
| 505 | B | − | − | − | − |
| 35 | C | − | − | − | − |
| 72 | C | − | − | − | − |
| 361 | C, D | − | − | − | − |
| 595 | C | − | − | − | − |
| 27 | D | − | − | − | − |
| 112 | A, D | − | − | − | − |
| 1151-7NG | D | − | − | − | − |
| 542 | D | − | − | − | − |
| FRI-326 (ATCC27664) | − (E) | + | + | + | + |

TABLE 66

| No. | Name | | Primer combination | | | |
|---|---|---|---|---|---|---|
| | | | a + d | a + f | b + c | b + e |
| 1 | Bacillus cereus | ATCC 14579 | − | − | − | − |
| 2 | Bacillus subtilis | JCM 1465 | − | − | − | − |
| 3 | Staphylococcus aureus | JCM 2413 | − | − | − | − |
| 4 | Staphylococcus epidermidis | JCM 2414 | − | − | − | − |
| 5 | Salmonella typhimurium | IFO 12529 | − | − | − | − |
| 6 | Salmonella enteritidis | IFO 3163 | − | − | − | − |
| 7 | Clostridium perfringens | ATCC 12917 | − | − | − | − |
| 8 | Vibrio cholerae | ATCC 25872 | − | − | − | − |
| 9 | Vibrio cholerae type ogawa | ATCC 9458 | − | − | − | − |
| 10 | Vibrio cholerae type inaba | ATCC 9459 | − | − | − | − |
| 11 | Vibrio fluvialis | JCM 3752 | − | − | − | − |
| 12 | Campylobacter jejuni | JCM 2013 | − | − | − | − |
| 13 | Campylobacter coli | JCM 2529 | − | − | − | − |
| 14 | Escherichia coli | JCM 1649 | − | − | − | − |
| 15 | Yersinia enterocolitica | ATCC 9610 | − | − | − | − |
| 16 | Shigella dysenteriae | ATCC 9361 | − | − | − | − |
| 17 | Shigella flexneri | ATCC 29903 | − | − | − | − |
| 18 | Shigella sonnei | ATCC 29930 | − | − | − | − |
| 19 | Bacteroides fragilis | ATCC 23745 | − | − | − | − |
| 20 | Bacteroides vulgatus | JCM 5326 | − | − | − | − |
| 21 | Enterococcus iaecalis | JCM 5803 | − | − | − | − |
| 22 | Klebsiella pneumoniae | JCM 1662 | − | − | − | − |
| 23 | Proteus vulgaris | JCM 1668 | − | − | − | − |
| 24 | Citrobacter freundii | ATCC 33128 | − | − | − | − |
| 25 | Streptococcus pyogenes | ATCC 12344 | − | − | − | − |
| 26 | Streptococcus pneumoniae | ATCC 33400 | − | − | − | − |
| 27 | Haemophilus influenzae | ATCC 33391 | − | − | − | − |
| 28 | Proteus mirabilis | ATCC 29906 | − | − | − | − |
| 29 | Neisseria gonorrhoeae | ATCC 19424 | − | − | − | − |
| 30 | Neisseria meningitidis | ATCC 13077 | − | − | − | − |
| 31 | Listeria monocytogenes | ATCC 15313 | − | − | − | − |
| 32 | Lactobacillus acidophilus | JCM 1132 | − | − | − | − |

TABLE 66-continued

|  |  |  | Primer combination | | | |
|---|---|---|---|---|---|---|
| No. | Name | | a + d | a + f | b + c | b + e |
| 33 | *Bilidobacterium adolescentis* | JCM 1275 | − | − | − | − |
| 34 | *Fusobacterium nucleatum* | ATCC 25586 | − | − | − | − |
| 35 | *Propionibacterium acnes* | ATCC 6919 | − | − | − | − |
| 36 | *Veillonella atypica* | ATCC 17744 | − | − | − | − |
| 37 | *Pseudomonas aeruginosa* | IFO 12689 | − | − | − | − |
| 38 | *Corynebacterium diphtheriae* | JCM 1310 | − | − | − | − |
| 39 | *Peptostreptococcus anaerobius* | ATCC 27337 | − | − | − | − |
| 40 | Human placental DNA | | − | − | − | − |

We claim:
1. A synthetic oligonucleotide for detecting the trh gene of *Vibrio parahaemolyticus*, consisting of a polynucleotide having a sequence selected from the group consisting of SEQ. I.D. NO.:1, the complement of SEQ. I.D. NO.:1, SEQ. I.D. NO.:2 and the complement of SEQ. I.D. NO.:2.

2. A synthetic oligonucleotide for detecting the trh gene of *Vibrio parahaemolyticus*, consisting of a polynucleotide having a sequence selected from the group consisting of SEQ. I.D. NO.:3, the complement of SEQ. I.D. NO.:3, SEQ..I.D. NO.:4, the complement of SEQ. I.D. NO.:4, SEQ. I.D. NO.:5, the complement of SEQ. I.D. NO.:5, SEQ. I.D. NO.:6 and the complement of SEQ. I.D. NO.:6.

3. A synthetic oligonucleotide for detecting the trh gens of *Vibrio parahaemolyticus*, consisting of a polynucleotide having a sequence selected form the groups consisting of SEQ. I.D. NO.:7, the complement of SEQ. I.D. NO.:7, SEQ. I.D. NO.:8 and the complement of SEQ. I.D. NO.:8.

* * * * *

SEQUENCE LISTING ( 1 ) GENERAL INFORMATION:

( i i i ) NUMBER OF SEQUENCES: 53

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Vibrio parahaemolyticus ( i x ) FEATURE:
        ( A ) NAME/KEY: -
        ( B ) LOCATION: 1..19
        ( D ) OTHER INFORMATION: /label=oligonucleotide
            / note="Identification method S"

( x i ) SEQUENCE DESCRIPTION: SEQ ID NO:1:

GGCTCAAAAT GGTTAAGCG                        1 9

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Vibrio parahaemolyticus ( i x ) FEATURE:
        ( A ) NAME/KEY: -
        ( B ) LOCATION: 1..19
        ( D ) OTHER INFORMATION: /label=oligonucleotide
            / note="Identification method S"

( x i ) SEQUENCE DESCRIPTION: SEQ ID NO:2:

CATTTCCGCT CTCATATGC            19

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Vibrio parahaemolyticus ( i x ) FEATURE:
        ( A ) NAME/KEY: -
        ( B ) LOCATION: 1..20
        ( D ) OTHER INFORMATION: /label=oligonucleotide
            / note="Identification method S"

( x i ) SEQUENCE DESCRIPTION: SEQ ID NO:3:

CCATCTGTCC CTTTTCCTGC            20

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Vibrio parahaemolyticus ( i x ) FEATURE:
        ( A ) NAME/KEY: -
        ( B ) LOCATION: 1..19
        ( D ) OTHER INFORMATION: /label=oligonucleotide
            / note="Identification method S"

( x i ) SEQUENCE DESCRIPTION: SEQ ID NO:4:

CCAAATACAT TTTACTTGG            19

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Vibrio parahaemolyticus ( i x ) FEATURE:
        ( A ) NAME/KEY: -

( B ) LOCATION: 1..20
            ( D ) OTHER INFORMATION: /label=oligonucleotide
                / note="Identification method S"

( x i ) SEQUENCE DESCRIPTION: SEQ ID NO:5:

GGTACTAAAT GGCTGACATC                    20

( 2 ) INFORMATION FOR SEQ ID NO:6:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
            ( A ) ORGANISM: Vibrio parahaemolyticus ( i x ) FEATURE:
            ( A ) NAME/KEY: -
            ( B ) LOCATION: 1..20
            ( D ) OTHER INFORMATION: /label=oligonucleotide
                / note="Identification method S"

( x i ) SEQUENCE DESCRIPTION: SEQ ID NO:6:

CCACTACCAC TCTCATATGC                    20

( 2 ) INFORMATION FOR SEQ ID NO:7:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
            ( A ) ORGANISM: Vibrio parahaemolyticus ( i x ) FEATURE:
            ( A ) NAME/KEY: -
            ( B ) LOCATION: 1..20
            ( D ) OTHER INFORMATION: /label=oligonucleotide
                / note="Identification method S"

( x i ) SEQUENCE DESCRIPTION: SEQ ID NO:7:

GGCTCAAAAT GGTTAAGCGC                    20

( 2 ) INFORMATION FOR SEQ ID NO:8:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( A ) ORGANISM: Vibrio parahaemolyticus ( i x ) FEATURE:
    ( A ) NAME/KEY: -
    ( B ) LOCATION: 1..20
    ( D ) OTHER INFORMATION: /label=oligonucleotide
        / note="Identification method S"

( x i ) SEQUENCE DESCRIPTION: SEQ ID NO:8:

TGGCGTTTCA TCCAAATACG     20

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Eschericia coli H10407

( i x ) FEATURE:
        ( A ) NAME/KEY: -
        ( B ) LOCATION: 1..19
        ( D ) OTHER INFORMATION: /label=oligonucleotide
            / note="Identification method S"

( x i ) SEQUENCE DESCRIPTION: SEQ ID NO:9:

CCCAGATGAA ATAAAACGT     19

( 2 ) INFORMATION FOR SEQ ID NO:10:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Eschericia coli H10407

( i x ) FEATURE:
        ( A ) NAME/KEY: -
        ( B ) LOCATION: 1..19
        ( D ) OTHER INFORMATION: /label=oligonucleotide
            / note="Identification method S"

( x i ) SEQUENCE DESCRIPTION: SEQ ID NO:10:

CCTGAGATAT ATTGTGCTC     19

( 2 ) INFORMATION FOR SEQ ID NO:11:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( A ) ORGANISM: Eschericia coli H10407

( i x ) FEATURE:
    ( A ) NAME/KEY: -
    ( B ) LOCATION: 1..22
    ( D ) OTHER INFORMATION: /label=oligonucleotide
        / note="Identification method S"

( x i ) SEQUENCE DESCRIPTION: SEQ ID NO:11:

ACAAACCGGC TTTGTCAGAT AT          22

( 2 ) INFORMATION FOR SEQ ID NO:12:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( A ) ORGANISM: Eschericia coli H10407

( i x ) FEATURE:
    ( A ) NAME/KEY: -
    ( B ) LOCATION: 1..22
    ( D ) OTHER INFORMATION: /label=oligonucleotide
        / note="Identification method S"

( x i ) SEQUENCE DESCRIPTION: SEQ ID NO:12:

GTTATATATG TCAACCTCTG AC          22

( 2 ) INFORMATION FOR SEQ ID NO:13:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( A ) ORGANISM: Eschericia coli H10407

( i x ) FEATURE:
    ( A ) NAME/KEY: -
    ( B ) LOCATION: 1..21
    ( D ) OTHER INFORMATION: /label=oligonucleotide
        / note="Identification method S"

( x i ) SEQUENCE DESCRIPTION: SEQ ID NO:13:

ACCGGTATTA CAGAAATCTG A          21

( 2 ) INFORMATION FOR SEQ ID NO:14:

( i ) SEQUENCE CHARACTERISTICS:
    ( A ) LENGTH: 24 base pairs ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
            ( A ) ORGANISM: Eschericia coli ( i x ) FEATURE:
            ( A ) NAME/KEY: -
            ( B ) LOCATION: 1..24
            ( D ) OTHER INFORMATION: /label=oligonucleotide
                  / note="Identification method S"

( x i ) SEQUENCE DESCRIPTION: SEQ ID NO:14:

TGTAATTTTC TCTTTTGAAG ACTC                  24

( 2 ) INFORMATION FOR SEQ ID NO:15:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
            ( A ) ORGANISM: Eschericia coli ( i x ) FEATURE:
            ( A ) NAME/KEY: -
            ( B ) LOCATION: 1..22
            ( D ) OTHER INFORMATION: /label=oligonucleotide
                  / note="Identification method S"

( x i ) SEQUENCE DESCRIPTION: SEQ ID NO:15:

ATTACAACAC AGTTCACAGC AG                    22

( 2 ) INFORMATION FOR SEQ ID NO:16:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
            ( A ) ORGANISM: Eschericia coli ( i x ) FEATURE:
            ( A ) NAME/KEY: -
            ( B ) LOCATION: 1..19
            ( D ) OTHER INFORMATION: /label=oligonucleotide
                  / note="Identification method S"

( x i ) SEQUENCE DESCRIPTION: SEQ ID NO:16:

CCTCAGGATG CTAAACCAG                        19

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Eschericia coli ( i x ) FEATURE:
        ( A ) NAME/KEY: -
        ( B ) LOCATION: 1..20
        ( D ) OTHER INFORMATION: /label=oligonucleotide
            / note="Identification method S"

( x i ) SEQUENCE DESCRIPTION: SEQ ID NO:17:

AGGATGCTAA ACCAGTAGAG                    20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Eschericia coli ( i x ) FEATURE:
        ( A ) NAME/KEY: -
        ( B ) LOCATION: 1..20
        ( D ) OTHER INFORMATION: /label=oligonucleotide
            / note="Identification method S"

( x i ) SEQUENCE DESCRIPTION: SEQ ID NO:18:

AGGATGCTAA ACCAGTAGAG                    20

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Eschericia coli ( i x ) FEATURE:
        ( A ) NAME/KEY: -
        ( B ) LOCATION: 1..21
        ( D ) OTHER INFORMATION: /label=oligonucleotide
            / note="Identification method S"

( x i ) SEQUENCE DESCRIPTION: SEQ ID NO:19:

TCTTTCCCCT CTTTTAGTCA G              2 1

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Eschericia coli ( i x ) FEATURE:
        ( A ) NAME/KEY: -
        ( B ) LOCATION: 1..21
        ( D ) OTHER INFORMATION: /label=oligonucleotide
            / note="Identification method S"

( x i ) SEQUENCE DESCRIPTION: SEQ ID NO:20:

GTCAACTGAA TCACTTGACT C              2 1

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Eschericia coli ( i x ) FEATURE:
        ( A ) NAME/KEY: -
        ( B ) LOCATION: 1..21
        ( D ) OTHER INFORMATION: /label=oligonucleotide
            / note="Identification method S"

( x i ) SEQUENCE DESCRIPTION: SEQ ID NO:21:

TCACAGCAGT AAAATGTGTT G              2 1

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Staphylococcus aureus ( i x ) FEATURE:
    ( A ) NAME/KEY: -
    ( B ) LOCATION: 1..20
    ( D ) OTHER INFORMATION: /label=oligonucleotide
        / note="Identification method S"

( x i ) SEQUENCE DESCRIPTION: SEQ ID NO:22:

GTCTGAATTG CAGGGAACAG                20

( 2 ) INFORMATION FOR SEQ ID NO:23:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( A ) ORGANISM: Staphylococcus aureus ( i x ) FEATURE:
    ( A ) NAME/KEY: -
    ( B ) LOCATION: 1..21
    ( D ) OTHER INFORMATION: /label=oligonucleotide
        / note="Identification method S"

( x i ) SEQUENCE DESCRIPTION: SEQ ID NO:23:

CTTTTTTACA GATCATTCGT G             21

( 2 ) INFORMATION FOR SEQ ID NO:24:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( A ) ORGANISM: Staphylococcus aureus ( i x ) FEATURE:
    ( A ) NAME/KEY: -
    ( B ) LOCATION: 1..24
    ( D ) OTHER INFORMATION: /label=oligonucleotide
        / note="Identification method S"

( x i ) SEQUENCE DESCRIPTION: SEQ ID NO:24:

TAGATTTTGA TTCAAAGGAT ATTG         24

( 2 ) INFORMATION FOR SEQ ID NO:25:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO -continued ( i v ) ANTI-SENSE: NO ( v i ) ORIGINAL SOURCE:
        ( A ) ORGANISM: Staphylococcus aureus ( i x ) FEATURE:
        ( A ) NAME/KEY: -
        ( B ) LOCATION: 1..22
        ( D ) OTHER INFORMATION: /label=oligonucleotide
          / note="Identification method S"

( x i ) SEQUENCE DESCRIPTION: SEQ ID NO:25:

CTTATTCGTT TTAACCGTTT CC          22

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Staphylococcus aureus ( i x ) FEATURE:
        ( A ) NAME/KEY: -
        ( B ) LOCATION: 1..20
        ( D ) OTHER INFORMATION: /label=oligonucleotide
          / note="Identification method S"

( x i ) SEQUENCE DESCRIPTION: SEQ ID NO:26:

AACACGATTA ATCCCCTCTG          20

( 2 ) INFORMATION FOR SEQ ID NO:27:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Staphylococcus aureus ( i x ) FEATURE:
        ( A ) NAME/KEY: -
        ( B ) LOCATION: 1..22
        ( D ) OTHER INFORMATION: /label=oligonucleotide
          / note="Identification method S"

( x i ) SEQUENCE DESCRIPTION: SEQ ID NO:27:

TCGTAATTAA CCGAAGGTTC TG          22

( 2 ) INFORMATION FOR SEQ ID NO:28:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (i i) MOLECULE TYPE: DNA (i i i) HYPOTHETICAL: NO (i v) ANTI-SENSE: NO (v i) ORIGINAL SOURCE:
    (A) ORGANISM: Staphylococcus aureus (i x) FEATURE:
    (A) NAME/KEY: -
    (B) LOCATION: 1..24
    (D) OTHER INFORMATION: /label=oligonucleotide
        / note="Identification method S"

(x i) SEQUENCE DESCRIPTION: SEQ ID NO:28:

AAATCTATAG ATCAATTTCT ATAC      24

(2) INFORMATION FOR SEQ ID NO:29:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (i i) MOLECULE TYPE: DNA (i i i) HYPOTHETICAL: NO (i v) ANTI-SENSE: NO (v i) ORIGINAL SOURCE:
    (A) ORGANISM: Staphylococcus aureus (i x) FEATURE:
    (A) NAME/KEY: -
    (B) LOCATION: 1..22
    (D) OTHER INFORMATION: /label=oligonucleotide
        / note="Identification method S"

(x i) SEQUENCE DESCRIPTION: SEQ ID NO:29:

AATTATGATA ATGTTCGAGT CG      22

(2) INFORMATION FOR SEQ ID NO:30:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: DNA (i i i) HYPOTHETICAL: NO (i v) ANTI-SENSE: NO (v i) ORIGINAL SOURCE:
    (A) ORGANISM: Staphylococcus aureus (i x) FEATURE:
    (A) NAME/KEY: -
    (B) LOCATION: 1..21
    (D) OTHER INFORMATION: /label=oligonucleotide
        / note="Identification method S"

(x i) SEQUENCE DESCRIPTION: SEQ ID NO:30:

TTCGCATCAA ACTGACAAAC G      21

(2) INFORMATION FOR SEQ ID NO:31:

( i ) SEQUENCE CHARACTERISTICS:
 ( A ) LENGTH: 21 base pairs
 ( B ) TYPE: nucleic acid
 ( C ) STRANDEDNESS: single
 ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
 ( A ) ORGANISM: Staphylococcus aureus ( i x ) FEATURE:
 ( A ) NAME/KEY: -
 ( B ) LOCATION: 1..21
 ( D ) OTHER INFORMATION: /label=oligonucleotide
  / note="Identification method S"

( x i ) SEQUENCE DESCRIPTION: SEQ ID NO:31:

CATCTTCAAA TACCCGAACA G   21

( 2 ) INFORMATION FOR SEQ ID NO:32:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
 ( A ) ORGANISM: Staphylococcus aureus ( i x ) FEATURE:
 ( A ) NAME/KEY: -
 ( B ) LOCATION: 1..20
 ( D ) OTHER INFORMATION: /label=oligonucleotide
  / note="Identification method S"

( x i ) SEQUENCE DESCRIPTION: SEQ ID NO:32:

CCAAATAGTG ACGAGTTAGG   20

( 2 ) INFORMATION FOR SEQ ID NO:33:

( i ) SEQUENCE CHARACTERISTICS:
 ( A ) LENGTH: 22 base pairs
 ( B ) TYPE: nucleic acid
 ( C ) STRANDEDNESS: single
 ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
 ( A ) ORGANISM: Staphylococcus aureus ( i x ) FEATURE:
 ( A ) NAME/KEY: -
 ( B ) LOCATION: 1..22
 ( D ) OTHER INFORMATION: /label=oligonucleotide
  / note="Identification method S"

( x i ) SEQUENCE DESCRIPTION: SEQ ID NO:33:

TCATACCAAA AGCTATTCTC AT        22

( 2 ) INFORMATION FOR SEQ ID NO:34:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Staphylococcus aureus ( i x ) FEATURE:
        ( A ) NAME/KEY: -
        ( B ) LOCATION: 1..21
        ( D ) OTHER INFORMATION: /label=oligonucleotide
            / note="Identification method S"

( x i ) SEQUENCE DESCRIPTION: SEQ ID NO:34:

TCTGTAGATA AATTTTTGGC A        21

( 2 ) INFORMATION FOR SEQ ID NO:35:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Staphylococcus aureus ( i x ) FEATURE:
        ( A ) NAME/KEY: -
        ( B ) LOCATION: 1..24
        ( D ) OTHER INFORMATION: /label=oligonucleotide
            / note="Identification method S"

( x i ) SEQUENCE DESCRIPTION: SEQ ID NO:35:

AAAATTATGA CAAAGTGAAA ACAG        24

( 2 ) INFORMATION FOR SEQ ID NO:36:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Staphylococcus aureus ( i x ) FEATURE:
        ( A ) NAME/KEY: -
        ( B ) LOCATION: 1..23

-continued ( D ) OTHER INFORMATION: /label=oligonucleotide
                              / note="Identification method S"

( x i ) SEQUENCE DESCRIPTION: SEQ ID NO:36:

ATGGATCAAA  TTACTATGTA  AAC               23

( 2 ) INFORMATION FOR SEQ ID NO:37:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
                ( A ) ORGANISM: Staphylococcus aureus ( i x ) FEATURE:
                ( A ) NAME/KEY: -
                ( B ) LOCATION: 1..20
                ( D ) OTHER INFORMATION: /label=oligonucleotide
                              / note="Identification method S"

( x i ) SEQUENCE DESCRIPTION: SEQ ID NO:37:

GTAGGTAAAG  TTACAGGTGG                    20

( 2 ) INFORMATION FOR SEQ ID NO:38:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
                ( A ) ORGANISM: Staphylococcus aureus ( i x ) FEATURE:
                ( A ) NAME/KEY: -
                ( B ) LOCATION: 1..23
                ( D ) OTHER INFORMATION: /label=oligonucleotide
                              / note="Identification method S"

( x i ) SEQUENCE DESCRIPTION: SEQ ID NO:38:

TATAAGTACA  TTTTGTAAGT  TCC               23

( 2 ) INFORMATION FOR SEQ ID NO:39:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:

(A) ORGANISM: Staphylococcus aureus (ix) FEATURE:
  (A) NAME/KEY: -
  (B) LOCATION: 1..22
  (D) OTHER INFORMATION: /label=oligonucleotide
     / note="Identification method S"

(xi) SEQUENCE DESCRIPTION: SEQ ID NO:39:

CATACCAAAA AGTATTGCCG TT    22

(2) INFORMATION FOR SEQ ID NO:40:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (vi) ORIGINAL SOURCE:
    (A) ORGANISM: Staphylococcus aureus (ix) FEATURE:
    (A) NAME/KEY: -
    (B) LOCATION: 1..23
    (D) OTHER INFORMATION: /label=oligonucleotide
       / note="Identification method S"

(xi) SEQUENCE DESCRIPTION: SEQ ID NO:40:

AAAATCTGAA TTAAGTAGTA CCG    23

(2) INFORMATION FOR SEQ ID NO:41:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (vi) ORIGINAL SOURCE:
    (A) ORGANISM: Staphylococcus aureus (ix) FEATURE:
    (A) NAME/KEY: -
    (B) LOCATION: 1..23
    (D) OTHER INFORMATION: /label=oligonucleotide
       / note="Identification method S"

(xi) SEQUENCE DESCRIPTION: SEQ ID NO:41:

ATAGGAGAAA ATAAAAGTAC AGG    23

(2) INFORMATION FOR SEQ ID NO:42:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (i i i) HYPOTHETICAL: NO (i v) ANTI-SENSE: NO (v i) ORIGINAL SOURCE:
    (A) ORGANISM: Staphylococcus aureus (i x) FEATURE:
    (A) NAME/KEY: -
    (B) LOCATION: 1..21
    (D) OTHER INFORMATION: /label=oligonucleotide
        / note="Identification method S"

(x i) SEQUENCE DESCRIPTION: SEQ ID NO:42:

CTTCAATTCA AAAGAAATGG C    21

(2) INFORMATION FOR SEQ ID NO:43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: NO (v i) ORIGINAL SOURCE:
        (A) ORGANISM: Staphylococcus aureus (i x) FEATURE:
        (A) NAME/KEY: -
        (B) LOCATION: 1..21
        (D) OTHER INFORMATION: /label=oligonucleotide
            / note="Identification method S"

(x i) SEQUENCE DESCRIPTION: SEQ ID NO:43:

TTGTACATAT GGAGGTGTCA C    21

(2) INFORMATION FOR SEQ ID NO:44:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: NO (v i) ORIGINAL SOURCE:
        (A) ORGANISM: Staphylococcus aureus (i x) FEATURE:
        (A) NAME/KEY: -
        (B) LOCATION: 1..23
        (D) OTHER INFORMATION: /label=oligonucleotide
            / note="Identification method S"

(x i) SEQUENCE DESCRIPTION: SEQ ID NO:44:

TTTTAGATTT GAAATGTTGA GCC    23

(2) INFORMATION FOR SEQ ID NO:45:

(i) SEQUENCE CHARACTERISTICS:
        (A) LENGTH: 21 base pairs
        (B) TYPE: nucleic acid (C) STRANDEDNESS: single
(D) TOPOLOGY: linear (i i) MOLECULE TYPE: DNA (i i i) HYPOTHETICAL: NO (i v) ANTI-SENSE: NO (v i) ORIGINAL SOURCE:
　　(A) ORGANISM: Staphylococcus aureus (i x) FEATURE:
　　(A) NAME/KEY: -
　　(B) LOCATION: 1..21
　　(D) OTHER INFORMATION: /label=oligonucleotide
　　　　/ note="Identification method S"

(x i) SEQUENCE DESCRIPTION: SEQ ID NO:45:

TGACACCTCC ATATGTACAA G　　　　21

(2) INFORMATION FOR SEQ ID NO:46:

(i) SEQUENCE CHARACTERISTICS:
　　　　(A) LENGTH: 25 base pairs
　　　　(B) TYPE: nucleic acid
　　　　(C) STRANDEDNESS: single
　　　　(D) TOPOLOGY: linear (i i) MOLECULE TYPE: DNA (i i i) HYPOTHETICAL: NO (i v) ANTI-SENSE: NO (v i) ORIGINAL SOURCE:
　　　　(A) ORGANISM: Staphylococcus aureus (i x) FEATURE:
　　　　(A) NAME/KEY: -
　　　　(B) LOCATION: 1..25
　　　　(D) OTHER INFORMATION: /label=oligonucleotide
　　　　　　/ note="Identification method S"

(x i) SEQUENCE DESCRIPTION: SEQ ID NO:46:

ATTATACAAT TTTAAATCCT TTTGC　　　　25

(2) INFORMATION FOR SEQ ID NO:47:

(i) SEQUENCE CHARACTERISTICS:
　　　　(A) LENGTH: 21 base pairs
　　　　(B) TYPE: nucleic acid
　　　　(C) STRANDEDNESS: single
　　　　(D) TOPOLOGY: linear (i i) MOLECULE TYPE: DNA (i i i) HYPOTHETICAL: NO (i v) ANTI-SENSE: NO (v i) ORIGINAL SOURCE:
　　　　(A) ORGANISM: Staphylococcus aureus (i x) FEATURE:
　　　　(A) NAME/KEY: -
　　　　(B) LOCATION: 1..21
　　　　(D) OTHER INFORMATION: /label=oligonucleotide
　　　　　　/ note="Identification method S"

(x i) SEQUENCE DESCRIPTION: SEQ ID NO:47:

CTGTATTTTT CCTCCGAGAG T　　　　21

( 2 ) INFORMATION FOR SEQ ID NO:48:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Staphylococcus aureus ( i x ) FEATURE:
        ( A ) NAME/KEY: -
        ( B ) LOCATION: 1..24
        ( D ) OTHER INFORMATION: /label=oligonucleotide
            / note="Identification method S"

( x i ) SEQUENCE DESCRIPTION: SEQ ID NO:48:

AAAAGTCTGA ATTACAAAGA AATG        24

( 2 ) INFORMATION FOR SEQ ID NO:49:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Staphylococcus aureus ( i x ) FEATURE:
        ( A ) NAME/KEY: -
        ( B ) LOCATION: 1..21
        ( D ) OTHER INFORMATION: /label=oligonucleotide
            / note="Identification method S"

( x i ) SEQUENCE DESCRIPTION: SEQ ID NO:49:

GGTTTTTTCA CAGGTCATCC A        21

( 2 ) INFORMATION FOR SEQ ID NO:50:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Staphylococcus aureus ( i x ) FEATURE:
        ( A ) NAME/KEY: -
        ( B ) LOCATION: 1..23
        ( D ) OTHER INFORMATION: /label=oligonucleotide
            / note="Identification method S"

( x i ) SEQUENCE DESCRIPTION: SEQ ID NO:50:

GAACAGTTAC TTCTTTTTTG CTT                23

( 2 ) INFORMATION FOR SEQ ID NO:51:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Staphylococcus aureus ( i x ) FEATURE:
        ( A ) NAME/KEY: -
        ( B ) LOCATION: 1..22
        ( D ) OTHER INFORMATION: /label=oligonucleotide
            / note="Identification method S"

( x i ) SEQUENCE DESCRIPTION: SEQ ID NO:51:

CTGTCTGAGT TATATAAACC AA                 22

( 2 ) INFORMATION FOR SEQ ID NO:52:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Staphylococcus aureus ( i x ) FEATURE:
        ( A ) NAME/KEY: -
        ( B ) LOCATION: 1..20
        ( D ) OTHER INFORMATION: /label=oligonucleotide
            / note="Identification method S"

( x i ) SEQUENCE DESCRIPTION: SEQ ID NO:52:

GCACCTTACC GCCAAAGCTG                    20

( 2 ) INFORMATION FOR SEQ ID NO:53:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Staphylococcus aureus ( i x ) FEATURE:

-continued (A) NAME/KEY: -
(B) LOCATION: 1..23
(D) OTHER INFORMATION: /label=oligonucleotide
  / note="Identification method S"

(xi) SEQUENCE DESCRIPTION: SEQ ID NO:53:

AAACAAATCA TAACTTACCG TG   22